US010787656B2

(12) United States Patent
Banerjee et al.

(10) Patent No.: US 10,787,656 B2
(45) Date of Patent: Sep. 29, 2020

(54) VARIANT ALKALINE PROTEASE ENZYME COMPOSITIONS AND METHODS

(71) Applicant: Fornia BioSolutions, Inc., Hayward, CA (US)

(72) Inventors: Goutami Banerjee, Hayward, CA (US); Jie Yang, Foster City, CA (US); Khin Oo, Daly City, CA (US); Xiyun Zhang, San Ramon, CA (US); Eric Lin Hu, Milbrae, CA (US); Imad N. Sawaya, Redwood City, CA (US)

(73) Assignee: Fomia BioSolutions, Inc., Hayward, CA (US)

( * ) Notice: Subject to any disclaimer, the term of this patent is extended or adjusted under 35 U.S.C. 154(b) by 0 days.

(21) Appl. No.: 16/402,144

(22) Filed: May 2, 2019

(65) Prior Publication Data

US 2019/0338222 A1 Nov. 7, 2019

Related U.S. Application Data

(60) Provisional application No. 62/667,038, filed on May 4, 2018.

(51) Int. Cl.

| | |
|---|---|
| ***C12N 9/12*** | (2006.01) |
| ***C12N 1/20*** | (2006.01) |
| ***C12N 15/00*** | (2006.01) |
| ***C12P 21/06*** | (2006.01) |
| ***C12P 21/04*** | (2006.01) |
| ***C07H 21/04*** | (2006.01) |
| ***C11D 3/386*** | (2006.01) |
| ***C12N 9/50*** | (2006.01) |
| ***C11D 11/00*** | (2006.01) |
| ***C11D 3/00*** | (2006.01) |
| ***C12N 9/62*** | (2006.01) |

(52) U.S. Cl.

CPC .............. *C12N 9/50* (2013.01); *C11D 3/0078* (2013.01); *C11D 3/386* (2013.01); *C11D 11/0017* (2013.01); *C11D 11/0023* (2013.01); *C12N 9/62* (2013.01)

(58) Field of Classification Search

None

See application file for complete search history.

(56) References Cited

U.S. PATENT DOCUMENTS

| | | | | |
|---|---|---|---|---|
| 6,376,227 | B1 * | 4/2002 | Takaiwa | C11D 3/386 435/219 |
| 9,567,596 | B2 * | 2/2017 | Landowski | C12P 21/005 |
| 10,240,159 | B2 * | 3/2019 | Landowski | C12P 21/005 |

OTHER PUBLICATIONS

Studer. Residue mutations and their impact on protein structure and function: detecting beneficial and pathogenic changes. Biochem. J. (2013) 449, 581-594.*

Fedorova. ORYZ_NEOFI. UniProtKB Database. 2017.*

Haddar et al., "Two detergent stable alkaline serine-proteases from Bacillus mojavensis A21: Purification, characterization and potential application as a laundry detergent additive", 2009, Bioresource Technology. 100(13):3366-3373.

Ellaiah et al., A Review on Microbial Alkaline Proteases:, 2002, Journal of Scientific & Industrial Research. 61:690-704.

Anwar et al., "Alkaline Proteases: A Review", 1998, Bioresource Technology. 64:175-183.

Saeki et al., "Detergent Alkaline Proteases: Enzymatic Properties, Genes, and Crystal Structures", 2007, Journal of Bioscience and Bioengineering. 103(6): 501-508.

GenBank accession No. AAB07672.1, serine proteinase [Aspergillus fumigatus], retrieved from the Internet on Dec. 11, 2019. https://www.ncbi.nlm.nih.gov/protein/AAB07672.1.

GenBank accession No. AAD47202.1, allergen Asp fl 1 [Aspergillus flavus], retrieved from the Internet on Dec. 10, 2019. https://www.ncbi.nlm.nih.gov/protein/AAD47202.1.

GenBank accession No. AAT85626.1, alkaline protease, partial [Aspergillus viridinutans], retrieved from the Internet on Dec. 18, 2019. https://www.ncbi.nlm.nih.gov/protein/AAT85626.1.

GenBank accession No. AAT85627.1, alkaline protease, partial [Aspergillus viridinutans], retrieved from the Internet on Dec. 18, 2019. https://www.ncbi.nlm.nih.gov/protein/AAT85627.1.

GenBank accession No. CAA75804.1, alkaline protease, partial [Aspergillus fumigatus], retrieved from the Internet on Dec. 16, 2019. https://www.ncbi.nlm.nih.gov/protein/CAA75804.1.

GenBank accession No. CAA75806.1, alkaline protease, partial [Aspergillus fumigatus], retrieved from the Internet on Dec. 16, 2019. https://www.ncbi.nlm.nih.gov/protein/CAA75806.1.

GenBank accession No. GA083403.1, alkaline protease 1 [Aspergillus udagawae], retrieved from the Internet on Dec. 16, 2019. https://www.ncbi.nlm.nih.gov/protein/GAO83403.1.

GenBank accession No. GAQ08309.1, alkaline protease 1 [Aspergillus lentulus], retrieved from the Internet on Dec. 10, 2019. https://www.ncbi.nlm.nih.gov/protein/GAQ08309.1.

GenBank accession No. KJK65194.1, Peptidase S8 family domain in ProteinaseK-like protein [Aspergillus parasiticus Su-1], retrieved from the Internet on Dec. 10, 2019. https://www.ncbi.nlm.nih.gov/protein/ KJK65194.1.

GenBank accession No. OXN19152.1, hypothetical protein CFD26_02594 [Aspergillus turcosus], retrieved from the Internet on Dec. 18, 2019. https://www.ncbi.nlm.nih.gov/protein/OXN19152.1?report=genpept Record removed. This genomic sequence record was removed because it has been superseded by a new assembly of the genome.

GenBank accession No. OXN40493.1, hypothetical protein CDV55_00141 [Aspergillus turcosus], retrieved from the Internet on Dec. 18, 2019. https://www.ncbi.nlm.nih.gov/protein/OXN19152.1?report=genpept Record removed. This genomic sequence record was removed because it has been superseded by a new assembly of the genome.

GenBank accession No. OXS05387.1, hypothetical protein CDV56_08311 [Aspergillus thermomutatus], retrieved from the Internet on Dec. 16, 2019. https://www.ncbi.nlm.nih.gov/protein/OXS05387.1?report=genpept Record removed. This genomic sequence record was removed because it has been superseded by a new assembly of the genome.

(Continued)

*Primary Examiner* — Yong D Pak

(74) *Attorney, Agent, or Firm* — Morgan, Lewis & Bockius LLP

(57) ABSTRACT

The invention is directed to novel alkaline proteases.

9 Claims, 30 Drawing Sheets

Specification includes a Sequence Listing.

(56) References Cited

OTHER PUBLICATIONS

GenBank accession No. PIG88895.1, oryzin [Aspergillus arachidicola], retrieved from the Internet on Dec. 11, 2019. https://www.ncbi.nlm.nih.gov/protein/PIG88895.1.
GenBank accession No. PKX92603.1, alkaline serine protease Alp1 [Aspergillus novofumigatus IBT 16806], retrieved from the Internet on Dec. 18, 2019. https://www.ncbi.nlm.nih.gov/protein/PKX92603.1.
GenBank accession No. PRF: 1410167A, alkaline protease, retrieved from the Internet on Dec. 11, 2019. https://www.ncbi.nlm.nih.gov/protein/226068.
GenBank accession number: PRF: 1905286A, extracellular alkaline protease, retrieved from the Internet on Dec. 11, 2019. https://www.ncbi.nlm.nih.gov/protein/384177.
NCBI Reference Sequence: XP_001266852.1, alkaline serine protease Alp1 [Aspergillus fischeri NRRL 181], retrieved from the Internet on Dec. 10, 2019. https://www.ncbi.nlm.nih.gov/protein/119500190.
NCBI Reference Sequence: XP_015409892.1, oryzin [Aspergillus nomius NRRL 13137], retrieved from the Internet on Dec. 11, 2019. https://www.ncbi.nlm.nih.gov/protein/XP_015409892.1.
NCBI Reference Sequence: XP_022392829.1, oryzin [Aspergillus bombycis], retrieved from the Internet on Dec. 11, 2019. https://www.ncbi.nlm.nih.gov/protein/XP_022392829.1.

* cited by examiner

FIGURE 3

Pre region (signal peptide)
*Pro region*
Mature region

| | | | | | |
|---|---|---|---|---|---|
| | 1 | | | | 50 |
| Ao.AP | **MQSIKRTLLL** | **LGAILPAVLG** | **A*PVQETRRAA*** | ***EKLPGKYIVT*** | ***FKPGIDEAKI*** |
| Nf.AP | **MLSIKRTLLL** | **LGAVLPAVFG** | **A*PVQETRRAA*** | ***QKIPGKYIVT*** | ***FKPGTDTATI*** |
| | 51 | | | | 100 |
| Ao.AP | ***QEHTTWATNI*** | ***HQRSLERRGA*** | ***TGGDLPVGIE*** | ***RNYKINKFAA*** | ***YAGSFDDATI*** |
| Nf.AP | ***ESHTLWATDL*** | ***HKRNLERRDT*** | ***TSGEPPVGIE*** | ***KSYKIKDFAA*** | ***YAGSFDDATI*** |
| | 101 | | | | 150 |
| Ao.AP | ***EEIRKNEDVA*** | ***YVEEDQIYYL*** | ***D***GLTTQKSAP | WGLGSISHKG | QQSTDYIYDT |
| Nf.AP | ***EEIRKRGDVA*** | ***HVEEDQIWYL*** | ***D***ALTTQKGAP | WGLGSISHKG | QASTDYIYDT |
| | 151 | | | | 200 |
| Ao.AP | SAGEGTYAYV | VDSGVNVDHE | EFEGRASKAY | NAAGGQHVDS | IGHGTHVSGT |
| Nf.AP | SAGAGTYAYV | VDSGINVNHV | EFESRASLAY | NAAGGSHVDS | IGHGTHVAGT |
| | 201 | | | | 250 |
| Ao.AP | IAGKTYGIAK | KASILSVKVF | QGESSSTSVI | LDGFNWAAND | IVSKKRTSKA |
| Nf.AP | IGGKTYGVAK | KTNLLSVKVF | QGESSSTSII | LDGFNWAVND | IVSKGRTKKA |
| | 251 | | | | 300 |
| Ao.AP | AINMSLGGGY | SKAFNDAVEN | AFEQGVLSVV | AAGNENSDAG | QTSPASAPDA |
| Nf.AP | AINMSLGGGY | SYAFNNAVEN | AFDEGVLSVV | AAGNENSDAS | NTSPASAPNA |
| | 301 | | | | 350 |
| Ao.AP | ITVAAIQKSN | NRASFSNFGK | VVDVFAPGQD | ILSAWIGSSS | ATNTISGTSM |
| Nf.AP | LTVAAINKSN | ARASFSNYGS | VVDIFAPGQD | ILSAWIGSTT | ATNTISGTSM |
| | 351 | | | | 400 |
| Ao.AP | ATPHIVGLSL | YLAALENLDG | PAAVTKRIKE | LATKDVVKDV | KGSPNLLAYN |
| Nf.AP | ATPHIVGLSV | YLMGLENLSG | PAAVTARIKE | LATNGVVTNV | KGSPNKLAYN |
| | 401 | | | | |
| Ao.AP | GNA | | | | |
| Nf.AP | GNA | | | | |

FIGURE 4

| Colony Tracking Number | High pH Tolerance Improvement | Thermostability Improvement | AA Mutations w.r.t. G1P (WT of Nf. AP) | Alias |
|---|---|---|---|---|
| | PF* at pH11.3, 37°C, 3hrs | PF* at pH11.0, 40°C, 3hrs | | |
| CL00037296 | 1.00 | 1.00 | | G1P |
| CL00052543 | 3.63 | 7.00 | K18R/A58G/N246G | G1V2 |
| CL00052570 | 4.34 | 4.20 | K18R/I234V | G1V3 |
| CL00052579 | 2.13 | 4.30 | K18R/A21G/S53G/A58G/K275L | |
| CL00052582 | 2.83 | 3.35 | K18R/S53G/A130V/I234V | G1V4 |
| CL00052631 | 3.41 | 3.54 | K18R/A58G | G1V1 |
| CL00052644 | 0.99 | 2.21 | K18R/T91A/I234V/N246G/K275L | |
| CL00052649 | 1.62 | 5.10 | K18R/A21G/A58G/I234V | |
| CL00052662 | 2.29 | 4.89 | K18R/S53G | |
| CL00052663 | 0.14 | 2.37 | K18R/A21G | |
| CL00052690 | 1.98 | 5.88 | K18R | |
| CL00052706 | 1.91 | 3.51 | K18R/A21G/I234V/N246G | |
| CL00052720 | 1.65 | 2.38 | K18R/S53G/A58G/I234V | |
| CL00052745 | 0.68 | 2.37 | K18R/S53G/T91A | |
| CL00052757 | 1.45 | 2.12 | K18R/A58G/I234V/K275L | |
| CL00052795 | 1.66 | 2.00 | K18R/I234V/K275L | |
| CL00052806 | 0.53 | 1.25 | A21G/S53G/K275L | |
| CL00052809 | 1.95 | 3.53 | K18R/A58G/K275L | |
| CL00052822 | 1.22 | 2.98 | K18R/A21G/A58G | |
| CL00052844 | 1.07 | 1.51 | K18R/D24H/S53G/A58G/A130V | |
| CL00052861 | 1.03 | 1.42 | K18R/S53G/A130V/K275L | |
| CL00052875 | 1.18 | 2.97 | K18R/S53G/T91A/I234V/K275L | |

FIGURE 5

| Colony Tracking Number | Activity Improvement | Thermostability Improvement | AA Mutations w.r.t. G1P (WT of Ao. AP) | Alias |
|---|---|---|---|---|
| | PF* at pH11.3, 37°C, 3hrs | PF* at pH11.0, 40°C, 3hrs | | |
| CL00037275 | 1.00 | 1.00 | | G1P |
| CL00052050 | 0.00 | 1.30 | Q21G/S77A/V203I | |
| CL00052064 | 1.32 | 1.68 | K18R/I87V | |
| CL00052070 | 1.33 | 1.83 | I87V/F197Y/V203I/I234V | |
| CL00052082 | 0.78 | 1.21 | A58G | |
| CL00052174 | 2.27 | 3.84 | K18R/Q21G/A58G/I87V/F197Y | G1V2 |
| CL00052220 | 1.01 | 0.96 | S77A/A117V/I234V | |
| CL00052236 | 3.64 | 0.00 | K18R/A117V | |
| CL00052304 | 1.40 | 1.50 | Q21G/A58G/I87V | |
| CL00052312 | 6.02 | 0.00 | I87V/A117V | |
| CL00052338 | 1.13 | 1.55 | I87V/F197Y | |
| CL00052357 | 1.23 | 2.10 | K18R/Q21G/I87V | |
| CL00052358 | 0.00 | 1.94 | I87V | |
| CL00052373 | 0.00 | 2.91 | K18R/I234V | |
| CL00052383 | 2.14 | 0.00 | S77A/I87V/A117V | |
| CL00052388 | 1.27 | 1.50 | K18R/Q21G/V203I/I234V | |
| CL00052412 | 1.39 | 1.99 | K18R/S77A/A183G | G1V1 |
| CL00052418 | 1.21 | 1.26 | S77A | |
| CL00052440 | 1.22 | 1.31 | K18R | |
| CL00052441 | 0.68 | 1.01 | Q21G/V203I | |
| CL00052473 | 1.08 | 1.56 | K18R/F197Y | |
| CL00052515 | 0.00 | 1.77 | K18R/I87V/F197Y/V203I | |
| CL00052530 | 3.23 | 1.40 | A117V | |

FIGURE 6

| Position | Wild type residue in Nf.AP | Particular variants | Wild type residue in Ao.AP | Particular variants | Common beneficial AA |
|---|---|---|---|---|---|
| 18 | K | R | K | R | R |
| 21 | A | G | Q | G | G |
| 24 | D | H | D | | |
| 53 | S | G | G | | G |
| 58 | A | G | A | G | G |
| 77 | A | | S | A | A |
| 87 | V | | I | V | V |
| 91 | T | A | A | | A |
| 117 | V | | A | V | V |
| 130 | A | V | | | |
| 183 | | | A | G | |
| 197 | Y | | F | Y | Y |
| 203 | I | | V | I | I |
| 234 | I | V | I | V | V |
| 246 | N | G | | | |
| 275 | K | L | L | | L |

FIGURE 7

| Accession # | %Sequence Identity to Nf.Ap |
|---|---|
| AAB07672.1 | 99.6 |
| PRF:1905286A | 99.6 |
| XP_001266852.1 | 95.4 |
| GAQ08309.1 | 95.0 |
| CAA75804.1 | 94.7 |
| PKX92603.1 | 95.0 |
| GAO83403.1 | 94.0 |
| OXS05387.1 | 93.6 |
| CAA75806.1 | 92.5 |
| AAT85626.1 | 93.4 |
| OXN40493.1 | 90.1 |
| AAT85627.1 | 93.0 |
| OXN19152.1 | 89.7 |
| Ao.Ap | 84.0 |

FIGURE 8

| Accession # | %Sequence Identity to Ao.Ap |
|---|---|
| PRF:1410167A | 99.6 |
| AAD47202.1 | 99.6 |
| KJK65194.1 | 97.5 |
| PIG88895.1 | 97.2 |
| XP_022392829.1 | 94.3 |
| XP_015409892.1 | 92.6 |
| Nf.Ap | 84 |

FIGURE 9A

>CL00037296 Nf.AP (G1P) (SEQ ID NO:1)

ALTTQKGAPWGLGSISHKGQASTDYIYDTSAGAGTYAYVVDSGINVNHVEFESRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052543 (SEQ ID NO:5)

ALTTQKGAPWGLGSISHRGQASTDYIYDTSAGAGTYAYVVDSGINVNHVEFESRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLEGLSGPAAVTARIKELATNGVVTNVKGSPNKLAYNG
NA

>CL00052570 (SEQ ID NO:3)

ALTTQKGAPWGLGSISHRGQASTDYIYDTSAGAGTYAYVVDSGINVNHVEFESRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNKLAYNG
NA

>CL00052579 (SEQ ID NO:9)

ALTTQKGAPWGLGSISHRGQGSTDYIYDTSAGAGTYAYVVDSGINVNHVEFEGRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNLLAYNG
NA

>CL00052582(SEQ ID NO:6)

ALTTQKGAPWGLGSISHRGQASTDYIYDTSAGAGTYAYVVDSGINVNHVEFEGRASLAYNAAGGSHVDSI
GHGTHVAGTIGGKTYGVAKKTNLLSVKVFQGESSSTSIILDGFNWAVNDIVSKGRTKKAVINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNKLAYNG
NA

>CL00052631(SEQ ID NO:7)

ALTTQKGAPWGLGSISHRGQASTDYIYDTSAGAGTYAYVVDSGINVNHVEFESRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

FIGURE 9B

>CL00052644 (SEQ ID NO:10)

ALTTQKGAPWGLGSISHRGQASTDYIYDTSAGAGTYAYVVDSGINVNHVEFESRASLAYNAAGGSHVDSI
GHGTHVAGTIGGKTYGVAKKANLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLEGLSGPAAVTARIKELATNGVVTNVKGSPNLLAYNG
NA

>CL00052649 (SEQ ID NO:11)

ALTTQKGAPWGLGSISHRGQGSTDYIYDTSAGAGTYAYVVDSGINVNHVEFESRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNKLAYNG
NA

>CL00052662 (SEQ ID NO:12)

ALTTQKGAPWGLGSISHRGQASTDYIYDTSAGAGTYAYVVDSGINVNHVEFEGRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052663 (SEQ ID NO:13)

ALTTQKGAPWGLGSISHRGQGSTDYIYDTSAGAGTYAYVVDSGINVNHVEFESRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052690 (SEQ ID NO:14)

ALTTQKGAPWGLGSISHRGQASTDYIYDTSAGAGTYAYVVDSGINVNHVEFESRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052706 (SEQ ID NO:15)

ALTTQKGAPWGLGSISHRGQGSTDYIYDTSAGAGTYAYVVDSGINVNHVEFESRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLEGLSGPAAVTARIKELATNGVVTNVKGSPNKLAYNG
NA

FIGURE 9C

>CL00052720 (SEQ ID NO:16)

ALTTQKGAPWGLGSISHRGQASTDYIYDTSAGAGTYAYVVDSGINVNHVEFEGRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNKLAYNG
NA

>CL00052745 (SEQ ID NO:17)

ALTTQKGAPWGLGSISHRGQASTDYIYDTSAGAGTYAYVVDSGINVNHVEFEGRASLAYNAAGGSHVDSI
GHGTHVAGTIGGKTYGVAKKANLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052757 (SEQ ID NO:18)

ALTTQKGAPWGLGSISHRGQASTDYIYDTSAGAGTYAYVVDSGINVNHVEFESRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNLLAYNG
NA

>CL00052795 (SEQ ID NO:19)

ALTTQKGAPWGLGSISHRGQASTDYIYDTSAGAGTYAYVVDSGINVNHVEFESRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNLLAYNG
NA

>CL00052806 (SEQ ID NO:20)

ALTTQKGAPWGLGSISHKGQGSTDYIYDTSAGAGTYAYVVDSGINVNHVEFEGRASLAYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNLLAYNG
NA

>CL00052809 (SEQ ID NO:21)

ALTTQKGAPWGLGSISHRGQASTDYIYDTSAGAGTYAYVVDSGINVNHVEFESRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNLLAYNG
NA

FIGURE 9D

>CL00052822 (SEQ ID NO:22)

ALTTQKGAPWGLGSISHRGQGSTDYIYDTSAGAGTYAYVVDSGINVNHVEFESRASLGYNAAGGSHVDSI
GHGTHVAGTIGGKTYGVAKKTNLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052844 (SEQ ID NO:23)

ALTTQKGAPWGLGSISHRGQASTHYIYDTSAGAGTYAYVVDSGINVNHVEFEGRASLGYNAAGGSHVDSI
GHGTHVAGTIGGKTYGVAKKTNLLSVKVFQGESSSTSIILDGFNWAVNDIVSKGRTKKAVINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNKLAYNG
NA

>CL00052861 (SEQ ID NO:24)

ALTTQKGAPWGLGSISHRGQASTDYIYDTSAGAGTYAYVVDSGINVNHVEFEGRASLAYNAAGGSHVDSI
GHGTHVAGTIGGKTYGVAKKTNLLSVKVFQGESSSTSIILDGFNWAVNDIVSKGRTKKAVINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHIVGLSVYLMGLENLSGPAAVTARIKELATNGVVTNVKGSPNLLAYNG
NA

>CL00052875 (SEQ ID NO:25)

ALTTQKGAPWGLGSISHRGQASTDYIYDTSAGAGTYAYVVDSGINVNHVEFEGRASLAYNAAGGSHVDSI
GHGTHVAGTIGGKTYGVAKKANLLSVKVFQGESSSTSIILDGFNWAVNDIVSKGRTKKAAINMSLGGGYS
YAFNNAVENAFDEGVLSVVAAGNENSDASNTSPASAPNALTVAAINKSNARASFSNYGSVVDIFAPGQDI
LSAWIGSTTATNTISGTSMATPHVVGLSVYLMGLENLSGPAAVTARIKELATNGVVTNVKGSPNLLAYNG
NA

FIGURE 10A

>CL00037275 Ao.AP (G1P)(SEQ ID NO:2)

GLTTQKSAPWGLGSISHKGQQSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052050 (SEQ ID NO:26)

GLTTQKSAPWGLGSISHKGQGSTDYIYDTSAGEGTYAYVVDSGVNVDHEEFEGRASKAYNAAGGQHVDSI
GHGTHVAGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDIFAPGQDI
LSAWIGSSSATNTISGTSMATPHIVGLSLYLAALENLDGPAAVTKRIKELATKDVVKDVKGSPNLLAYNG
NA

>CL00052064 (SEQ ID NO:27)

GLTTQKSAPWGLGSISHRGQQSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052070 (SEQ ID NO:28)

GLTTQKSAPWGLGSISHKGQQSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNYGKVVDIFAPGQDI
LSAWIGSSSATNTISGTSMATPHVVGLSLYLAALENLDGPAAVTKRIKELATKDVVKDVKGSPNLLAYNG
NA

>CL00052082 (SEQ ID NO:29)

GLTTQKSAPWGLGSISHKGQQSTDYIYDTSAGEGTYAYVVDSGVNVDHEEFEGRASKGYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052174 (SEQ ID NO:4)

GLTTQKSAPWGLGSISHRGQGSTDYIYDTSAGEGTYAYVVDSGVNVDHEEFEGRASKGYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNYGKVVDVFAPGQDI
LSAWIGSSSATNTISGTSMATPHIVGLSLYLAALENLDGPAAVTKRIKELATKDVVKDVKGSPNLLAYNG
NA

FIGURE 10B

>CL00052220 (SEQ ID NO:30)

GLTTQKSAPWGLGSISHKGQQSTDYIYDTSAGEGTYAYVVDSGVNVDHEEFEGRASKAYNAAGGQHVDSI
GHGTHVAGTIAGKTYGIAKKASILSVKVFQGESSSTSVILDGFNWAVNDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHVVGLSLYLAALENLDGPAAVTKRIKELATKDVVKDVKGSPNLLAYNG
NA

>CL00052236 (SEQ ID NO:31)

GLTTQKSAPWGLGSISHRGQQSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAVNDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052304 (SEQ ID NO:32)

GLTTQKSAPWGLGSISHKGQGSTDYIYDTSAGEGTYAYVVDSGVNVDHEEFEGRASKGYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052312 (SEQ ID NO:33)

GLTTQKSAPWGLGSISHKGQQSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAVNDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052338 (SEQ ID NO:34)

GLTTQKSAPWGLGSISHKGQQSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNYGKVVDVFAPGQDI
LSAWIGSSSATNTISGTSMATPHIVGLSLYLAALENLDGPAAVTKRIKELATKDVVKDVKGSPNLLAYNG
NA

>CL00052357 (SEQ ID NO:35)

GLTTQKSAPWGLGSISHRGQGSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

FIGURE 10C

>CL00052358 (SEQ ID NO:36)

GLTTQKSAPWGLGSISHKGQQSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052373 (SEQ ID NO:37)

GLTTQKSAPWGLGSISHRGQQSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHVVGLSLYLAALENLDGPAAVTKRIKELATKDVVKDVKGSPNLLAYNG
NA

>CL00052383 (SEQ ID NO:38)

GLTTQKSAPWGLGSISHKGQQSTDYIYDTSAGEGTYAYVVDSGVNVDHEEFEGRASKAYNAAGGQHVDSI
GHGTHVAGTIAGKTYGVAKKASILSVKVFQGESSSTSVILDGFNWAVNDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052388 (SEQ ID NO:39)

GLTTQKSAPWGLGSISHRGQGSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDIFAPGQDI
LSAWIGSSSATNTISGTSMATPHVVGLSLYLAALENLDGPAAVTKRIKELATKDVVKDVKGSPNLLAYNG
NA

>CL00052412(SEQ ID NO:8)

GLTTQKSAPWGLGSISHRGQQSTDYIYDTSAGEGTYAYVVDSGVNVDHEEFEGRASKAYNAAGGQHVDSI
GHGTHVAGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVGAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052418 (SEQ ID NO:40)

GLTTQKSAPWGLGSISHKGQQSTDYIYDTSAGEGTYAYVVDSGVNVDHEEFEGRASKAYNAAGGQHVDSI
GHGTHVAGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

FIGURE 10D

>CL00052440 (SEQ ID NO:41)

GLTTQKSAPWGLGSISHRGQQSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

>CL00052441 (SEQ ID NO:42)

GLTTQKSAPWGLGSISHKGQGSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNFGKVVDIFAPGQDI
LSAWIGSSSATNTISGTSMATPHIVGLSLYLAALENLDGPAAVTKRIKELATKDVVKDVKGSPNLLAYNG
NA

>CL00052473 (SEQ ID NO:43)

GLTTQKSAPWGLGSISHRGQQSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNYGKVVDVFAPGQDI
LSAWIGSSSATNTISGTSMATPHIVGLSLYLAALENLDGPAAVTKRIKELATKDVVKDVKGSPNLLAYNG
NA

>CL00052515 (SEQ ID NO:44)

GLTTQKSAPWGLGSISHRGQQSTDYIYDTSAGEGTYAYVVDSGVNVDHEEFEGRASKAYNAAGGQHVDSI
GHGTHVSGTIAGKTYGVAKKASILSVKVFQGESSSTSVILDGFNWAANDIVSKKRTSKAAINMSLGGGYS
KAFNDAVENAFEQGVLSVVAAGNENSDAGQTSPASAPDAITVAAIQKSNNRASFSNYGKVVDIFAPGQDI
LSAWIGSSSATNTISGTSMATPHIVGLSLYLAALENLDGPAAVTKRIKELATKDVVKDVKGSPNLLAYNG
NA

>CL00052530 (SEQ ID NO:45)

GLTTQKSAPWGLGSISHKGQQSTDYIYDTSAGEGTYAYVVDSGVNVDHEEFEGRASKAYNAAGGQHVDSI
GHGTHVSGTIAGKTYGIAKKASILSVKVFQGESSSTSVILDGFNWAVNDIVSKKRTSKAAINMSLGGGYS
KAFNDAVENAFEQGVLSVVAAGNENSDAGQTSPASAPDAITVAAIQKSNNRASFSNFGKVVDVFAPGQDI
LSAWIGSSSATNTISGTSMATPHIVGLSLYLAALENLDGPAAVTKRIKELATKDVVKDVKGSPNLLAYNG
NA

FIGURE 11A

>CL00037296 Nf.AP (G1P) (SEQ ID NO:46)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHKG
QASTDYIYDTSAGAGTYAYVVDSGINVNHVEFESRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

>CL00052543 (SEQ ID NO:47)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLEGLSGPAAVTARIKELATNGVVTNVKGSPNKLAYNGNA

>CL00052570 (SEQ ID NO:48)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNKLAYNGNA

>CL00052579 (SEQ ID NO:49)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QGSTDYIYDTSAGAGTYAYVVDSGINVNHVEFEGRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNLLAYNGNA

>CL00052582 (SEQ ID NO:50)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFEGRASLAYNAAGGSHVDSIGHGTHVAGTIGGKTYGVAK
KTNLLSVKVFQGESSSTSIILDGFNWAVNDIVSKGRTKKAVINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNKLAYNGNA

FIGURE 11B

>CL00052631 (SEQ ID NO:51)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

>CL00052644 (SEQ ID NO:52)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLAYNAAGGSHVDSIGHGTHVAGTIGGKTYGVAK
KANLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLEGLSGPAAVTARIKELATNGVVTNVKGSPNLLAYNGNA

>CL00052649 (SEQ ID NO:53)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QGSTDYIYDTSAGAGTYAYVVDSGINVNHVEFESRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNKLAYNGNA

>CL00052662 (SEQ ID NO:54)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFEGRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

>CL00052663 (SEQ ID NO:55)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QGSTDYIYDTSAGAGTYAYVVDSGINVNHVEFESRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

FIGURE 11C

>CL00052690 (SEQ ID NO:56)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

>CL00052706 (SEQ ID NO:57)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QGSTDYIYDTSAGAGTYAYVVDSGINVNHVEFESRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLEGLSGPAAVTARIKELATNGVVTNVKGSPNKLAYNGNA

>CL00052720 (SEQ ID NO:58)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFEGRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNKLAYNGNA

>CL00052745 (SEQ ID NO:59)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFEGRASLAYNAAGGSHVDSIGHGTHVAGTIGGKTYGVAK
KANLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

>CL00052757 (SEQ ID NO:60)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNLLAYNGNA

FIGURE 11D

>CL00052795 (SEQ ID NO:61)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNLLAYNGNA

>CL00052806 (SEQ ID NO:62)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHKG
QGSTDYIYDTSAGAGTYAYVVDSGINVNHVEFEGRASLAYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNLLAYNGNA

>CL00052809 (SEQ ID NO:63)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFESRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNLLAYNGNA

>CL00052822 (SEQ ID NO:64)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QGSTDYIYDTSAGAGTYAYVVDSGINVNHVEFESRASLGYNAAGGSHVDSIGHGTHVAGTIGGKTYGVAK
KTNLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

>CL00052844 (SEQ ID NO:65)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTHYIYDTSAGAGTYAYVVDSGINVNHVEFEGRASLGYNAAGGSHVDSIGHGTHVAGTIGGKTYGVAK
KTNLLSVKVFQGESSSTSIILDGFNWAVNDIVSKGRTKKAVINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNKLAYNGNA

FIGURE 11E

>CL00052861 (SEQ ID NO:66)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFEGRASLAYNAAGGSHVDSIGHGTHVAGTIGGKTYGVAK
KTNLLSVKVFQGESSSTSIILDGFNWAVNDIVSKGRTKKAVINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHIVGLSVYLMGLENLSGPAAVTARIKELATNGVVTNVKGSPNLLAYNGNA

>CL00052875 (SEQ ID NO:67)

MLSIKRTLLLLGAVLPAVFGAPVQETRRAAQKIPGKYIVTFKPGTDTATIESHTLWATDLHKRNLERRDT
TSGEPPVGIEKSYKIKDFAAYAGSFDDATIEEIRKRGDVAHVEEDQIWYLDALTTQKGAPWGLGSISHRG
QASTDYIYDTSAGAGTYAYVVDSGINVNHVEFEGRASLAYNAAGGSHVDSIGHGTHVAGTIGGKTYGVAK
KANLLSVKVFQGESSSTSIILDGFNWAVNDIVSKGRTKKAAINMSLGGGYSYAFNNAVENAFDEGVLSVV
AAGNENSDASNTSPASAPNALTVAAINKSNARASFSNYGSVVDIFAPGQDILSAWIGSTTATNTISGTSM
ATPHVVGLSVYLMGLENLSGPAAVTARIKELATNGVVTNVKGSPNLLAYNGNA

FIGURE 12A

>CL00037275 Ao.AP (G1P) (SEQ ID NO:68)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052050 (SEQ ID NO:69)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QGSTDYIYDTSAGEGTYAYVVDSGVNVDHEEFEGRASKAYNAAGGQHVDSIGHGTHVAGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDIFAPGQDILSAWIGSSSATNTISGTSM
ATPHIVGLSLYLAALENLDGPAAVTKRIKELATKDVVKDVKGSPNLLAYNGNA

>CL00052064 (SEQ ID NO:70)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052070 (SEQ ID NO:71)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNYGKVVDIFAPGQDILSAWIGSSSATNTISGTSM
ATPHVVGLSLYLAALENLDGPAAVTKRIKELATKDVVKDVKGSPNLLAYNGNA

>CL00052082 (SEQ ID NO:72)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKGYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

FIGURE 12B

>CL00052174 (SEQ ID NO:73)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QGSTDYIYDTSAGEGTYAYVVDSGVNVDHEEFEGRASKGYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNYGKVVDVFAPGQDILSAWIGSSSATNTISGTSM
ATPHIVGLSLYLAALENLDGPAAVTKRIKELATKDVVKDVKGSPNLLAYNGNA

>CL00052220 (SEQ ID NO:74)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVAGTIAGKTYGIAK
KASILSVKVFQGESSSTSVILDGFNWAVNDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHVVGLSLYLAALENLDGPAAVTKRIKELATKDVVKDVKGSPNLLAYNGNA

>CL00052236 (SEQ ID NO:75)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAVNDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052304 (SEQ ID NO:76)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QGSTDYIYDTSAGEGTYAYVVDSGVNVDHEEFEGRASKGYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052312 (SEQ ID NO:77)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAVNDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

FIGURE 12C

>CL00052338 (SEQ ID NO:78)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNYGKVVDVFAPGQDILSAWIGSSSATNTISGTSM
ATPHIVGLSLYLAALENLDGPAAVTKRIKELATKDVVKDVKGSPNLLAYNGNA

>CL00052357 (SEQ ID NO:79)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QGSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052358 (SEQ ID NO:80)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052373 (SEQ ID NO:81)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHVVGLSLYLAALENLDGPAAVTKRIKELATKDVVKDVKGSPNLLAYNGNA

>CL00052383 (SEQ ID NO:82)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVAGTIAGKTYGVAK
KASILSVKVFQGESSSTSVILDGFNWAVNDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

FIGURE 12D

>CL00052388 (SEQ ID NO:83)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QGSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDIFAPGQDILSAWIGSSSATNTISGTSM
ATPHVVGLSLYLAALENLDGPAAVTKRIKELATKDVVKDVKGSPNLLAYNGNA

>CL00052412 (SEQ ID NO:84)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVAGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVGAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052418 (SEQ ID NO:85)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVAGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052440 (SEQ ID NO:86)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

>CL00052441 (SEQ ID NO:87)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QGSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNFGKVVDIFAPGQDILSAWIGSSSATNTISGTSM
ATPHIVGLSLYLAALENLDGPAAVTKRIKELATKDVVKDVKGSPNLLAYNGNA

FIGURE 12E

>CL00052473 (SEQ ID NO:88)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNYGKVVDVFAPGQDILSAWIGSSSATNTISGTSM
ATPHIVGLSLYLAALENLDGPAAVTKRIKELATKDVVKDVKGSPNLLAYNGNA

>CL00052515 (SEQ ID NO:89)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHRG
QQSTDYIYDTSAGEGTYAYVVDSGVNVDHEEFEGRASKAYNAAGGQHVDSIGHGTHVSGTIAGKTYGVAK
KASILSVKVFQGESSSTSVILDGFNWAANDIVSKKRTSKAAINMSLGGGYSKAFNDAVENAFEQGVLSVV
AAGNENSDAGQTSPASAPDAITVAAIQKSNNRASFSNYGKVVDIFAPGQDILSAWIGSSSATNTISGTSM
ATPHIVGLSLYLAALENLDGPAAVTKRIKELATKDVVKDVKGSPNLLAYNGNA

>CL00052530 (SEQ ID NO:90)

MQSIKRTLLLLGAILPAVLGAPVQETRRAAEKLPGKYIVTFKPGIDEAKIQEHTTWATNIHQRSLERRGA
TGGDLPVGIERNYKINKFAAYAGSFDDATIEEIRKNEDVAYVEEDQIYYLDGLTTQKSAPWGLGSISHKG
QQSTDYIYDTSAGEGTYAYVVDSGVNVDHEEFEGRASKAYNAAGGQHVDSIGHGTHVSGTIAGKTYGIAK
KASILSVKVFQGESSSTSVILDGFNWAVNDIVSKKRTSKAAINMSLGGGYSKAFNDAVENAFEQGVLSVV
AAGNENSDAGQTSPASAPDAITVAAIQKSNNRASFSNFGKVVDVFAPGQDILSAWIGSSSATNTISGTSM
ATPHIVGLSLYLAALENLDGPAAVTKRIKELATKDVVKDVKGSPNLLAYNGNA

SEQUENCE LISTING

```
<160> NUMBER OF SEQ ID NOS: 180

<210> SEQ ID NO 1
<211> LENGTH: 282
<212> TYPE: PRT
<213> ORGANISM: Artificial Sequence
<220> FEATURE:
<223> OTHER INFORMATION: Alkaline Protease (CL00037296 Nf.AP) (G1P)

<400> SEQUENCE: 1

Ala Leu Thr Thr Gln Lys Gly Ala Pro Trp Gly Leu Gly Ser Ile Ser
1               5                   10                  15

His Lys Gly Gln Ala Ser Thr Asp Tyr Ile Tyr Asp Thr Ser Ala Gly
            20                  25                  30
```

```
Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 2
<211> LENGTH: 282
<212> TYPE: PRT
<213> ORGANISM: Artificial Sequence
<220> FEATURE:
<223> OTHER INFORMATION: Alkaline Protease (CL00037275 Ao.AP) (G1P)

<400> SEQUENCE: 2

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110
```

```
Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 3
<211> LENGTH: 282
<212> TYPE: PRT
<213> ORGANISM: Artificial Sequence
<220> FEATURE:
<223> OTHER INFORMATION: Synthetic Alkaline Protease (CL00052570)

<400> SEQUENCE: 3

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190
```

```
Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 4
<211> LENGTH: 282
<212> TYPE: PRT
<213> ORGANISM: Artificial Sequence
<220> FEATURE:
<223> OTHER INFORMATION: Synthetic Alkaline Protease (CL00052174)

<400> SEQUENCE: 4

Gly Leu Thr Thr Gln Lys Ser Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Gly Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Tyr Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270
```

```
Pro Asn Leu Leu Ala Tyr Asn Gly Asn Ala
        275                 280


<210> SEQ ID NO 5
<211> LENGTH: 282
<212> TYPE: PRT
<213> ORGANISM: Artificial Sequence
<220> FEATURE:
<223> OTHER INFORMATION: Synthetic Alkaline Protease (CL00052543)

<400> SEQUENCE: 5

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Gly Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 6
<211> LENGTH: 282
<212> TYPE: PRT
<213> ORGANISM: Artificial Sequence
<220> FEATURE:
<223> OTHER INFORMATION: Synthetic Alkaline Protease (CL00052582)

<400> SEQUENCE: 6

Ala Leu Thr Thr Gln Lys Gly Ala Pro Trp Gly Leu Gly Ser Ile Ser
1               5                   10                  15
```

```
His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Val Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 7
<211> LENGTH: 282
<212> TYPE: PRT
<213> ORGANISM: Artificial Sequence
<220> FEATURE:
<223> OTHER INFORMATION: Synthetic Alkaline Protease (CL00052631)

<400> SEQUENCE: 7

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95
```

```
Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 8
<211> LENGTH: 282
<212> TYPE: PRT
<213> ORGANISM: Artificial Sequence
<220> FEATURE:
<223> OTHER INFORMATION: Synthetic Alkaline Protease (CL00052412)

<400> SEQUENCE: 8

Gly Leu Thr Thr Gln Lys Ser Ala Pro Trp Gly Leu Gly Ser Ile Ser
1               5                   10                  15

His Arg Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ala Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175
```

```
Pro Asp Ala Ile Thr Val Gly Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 9
<211> LENGTH: 282
<212> TYPE: PRT
<213> ORGANISM: Artificial Sequence
<220> FEATURE:
<223> OTHER INFORMATION: Synthetic Alkaline Protease (CL00052579)

<400> SEQUENCE: 9

Ala Leu Thr Thr Gln Lys Gly Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255
```

```
Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280
```

<210> SEQ ID NO 10
<211> LENGTH: 282
<212> TYPE: PRT
<213> ORGANISM: Artificial Sequence
<220> FEATURE:
<223> OTHER INFORMATION: Synthetic Alkaline Protease (CL00052644)

<400> SEQUENCE: 10

```
Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Ala Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Gly Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280
```

<210> SEQ ID NO 11
<211> LENGTH: 282
<212> TYPE: PRT
<213> ORGANISM: Artificial Sequence
<220> FEATURE:
<223> OTHER INFORMATION: Synthetic Alkaline Protease (CL00052649)

<400> SEQUENCE: 11

```
Ala Leu Thr Thr Gln Lys Gly Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280
```

<210> SEQ ID NO 12
<211> LENGTH: 282
<212> TYPE: PRT
<213> ORGANISM: Artificial Sequence
<220> FEATURE:
<223> OTHER INFORMATION: Synthetic Alkaline Protease (CL00052662)

<400> SEQUENCE: 12

```
Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Ala Tyr Asn Ala Ala Gly Gly
    50                  55                  60

Ser His Val Asp Ser Ile Gly His Gly Thr His Val Ala Gly Thr Ile
```

```
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 13
<211> LENGTH: 282
<212> TYPE: PRT
<213> ORGANISM: Artificial Sequence
<220> FEATURE:
<223> OTHER INFORMATION: Synthetic Alkaline Protease (CL00052663)

<400> SEQUENCE: 13

Ala Leu Thr Thr Gln Lys Gly Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
```

```
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 14
<211> LENGTH: 282
<212> TYPE: PRT
<213> ORGANISM: Artificial Sequence
<220> FEATURE:
<223> OTHER INFORMATION: Synthetic Alkaline Protease (CL00052690)

<400> SEQUENCE: 14

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
```

```
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 15
<211> LENGTH: 282
<212> TYPE: PRT
<213> ORGANISM: Artificial Sequence
<220> FEATURE:
<223> OTHER INFORMATION: Synthetic Alkaline Protease (CL00052706)

<400> SEQUENCE: 15

Ala Leu Thr Thr Gln Lys Gly Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Gly Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 16
<211> LENGTH: 282
<212> TYPE: PRT
```

```
<213> ORGANISM: Artificial Sequence
<220> FEATURE:
<223> OTHER INFORMATION: Synthetic Alkaline Protease (CL00052720)

<400> SEQUENCE: 16

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 17
<211> LENGTH: 282
<212> TYPE: PRT
<213> ORGANISM: Artificial Sequence
<220> FEATURE:
<223> OTHER INFORMATION: Synthetic Alkaline Protease (CL00052745)

<400> SEQUENCE: 17

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45
```

```
Val Glu Phe Glu Gly Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Ala Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 18
<211> LENGTH: 282
<212> TYPE: PRT
<213> ORGANISM: Artificial Sequence
<220> FEATURE:
<223> OTHER INFORMATION: Synthetic Alkaline Protease (CL00052757)

<400> SEQUENCE: 18

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125
```

```
Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280


<210> SEQ ID NO 19
<211> LENGTH: 282
<212> TYPE: PRT
<213> ORGANISM: Artificial Sequence
<220> FEATURE:
<223> OTHER INFORMATION: Synthetic Alkaline Protease (CL00052795)

<400> SEQUENCE: 19

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205
```

```
Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280


<210> SEQ ID NO 20
<211> LENGTH: 282
<212> TYPE: PRT
<213> ORGANISM: Artificial Sequence
<220> FEATURE:
<223> OTHER INFORMATION: Synthetic Alkaline Protease (CL00052806)

<400> SEQUENCE: 20

Ala Leu Thr Thr Gln Lys Gly Ala Pro Trp Gly Leu Gly Ser Ile Ser
1               5                   10                  15

His Lys Gly Gln Gly Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280
```

<210> SEQ ID NO 21
<211> LENGTH: 282
<212> TYPE: PRT
<213> ORGANISM: Artificial Sequence
<220> FEATURE:
<223> OTHER INFORMATION: Synthetic Alkaline Protease (CL00052809)

<400> SEQUENCE: 21

```
Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Ser Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280
```

<210> SEQ ID NO 22
<211> LENGTH: 282
<212> TYPE: PRT
<213> ORGANISM: Artificial Sequence
<220> FEATURE:
<223> OTHER INFORMATION: Synthetic Alkaline Protease (CL00052822)

<400> SEQUENCE: 22

```
Ala Leu Thr Thr Gln Lys Gly Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30
```

```
Ala Gly Thr Tyr Ala Tyr Val Val Asp Ser Gly Ile Asn Val Asn His
        35                  40                  45

Val Glu Phe Glu Ser Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 23
<211> LENGTH: 282
<212> TYPE: PRT
<213> ORGANISM: Artificial Sequence
<220> FEATURE:
<223> OTHER INFORMATION: Synthetic Alkaline Protease (CL00052844)

<400> SEQUENCE: 23

Ala Leu Thr Thr Gln Lys Gly Ala Pro Trp Gly Leu Gly Ser Ile Ser
1               5                   10                  15

His Arg Gly Gln Ala Ser Thr His Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Gly Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110
```

```
Phe Asn Trp Ala Val Asn Asp Ile Val Ser Lys Gly Arg Thr Lys Lys
        115                 120                 125

Ala Val Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Lys Leu Ala Tyr Asn Gly Asn Ala
        275                 280


<210> SEQ ID NO 24
<211> LENGTH: 282
<212> TYPE: PRT
<213> ORGANISM: Artificial Sequence
<220> FEATURE:
<223> OTHER INFORMATION: Synthetic Alkaline Protease (CL00052861)

<400> SEQUENCE: 24

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Thr Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Val Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190
```

```
Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Ile Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270

Pro Asn Leu Leu Ala Tyr Asn Gly Asn Ala
        275                 280


<210> SEQ ID NO 25
<211> LENGTH: 282
<212> TYPE: PRT
<213> ORGANISM: Artificial Sequence
<220> FEATURE:
<223> OTHER INFORMATION: Synthetic Alkaline Protease (CL00052875)

<400> SEQUENCE: 25

Ala Leu Thr Thr Gln Lys Gly Ala Pro Trp Gly Leu Gly Ser Ile Ser
1               5                   10                  15

His Arg Gly Gln Ala Ser Thr Asp Tyr Ile Tyr Asp Thr Ser Ala Gly
            20                  25                  30

Ala Gly Thr Tyr Ala Tyr Val Val Asp Ser Gly Ile Asn Val Asn His
        35                  40                  45

Val Glu Phe Glu Gly Arg Ala Ser Leu Ala Tyr Asn Ala Ala Gly Gly
    50                  55                  60

Ser His Val Asp Ser Ile Gly His Gly Thr His Val Ala Gly Thr Ile
65                  70                  75                  80

Gly Gly Lys Thr Tyr Gly Val Ala Lys Lys Ala Asn Leu Leu Ser Val
                85                  90                  95

Lys Val Phe Gln Gly Glu Ser Ser Ser Thr Ser Ile Ile Leu Asp Gly
            100                 105                 110

Phe Asn Trp Ala Val Asn Asp Ile Val Ser Lys Gly Arg Thr Lys Lys
        115                 120                 125

Ala Ala Ile Asn Met Ser Leu Gly Gly Gly Tyr Ser Tyr Ala Phe Asn
    130                 135                 140

Asn Ala Val Glu Asn Ala Phe Asp Glu Gly Val Leu Ser Val Val Ala
145                 150                 155                 160

Ala Gly Asn Glu Asn Ser Asp Ala Ser Asn Thr Ser Pro Ala Ser Ala
                165                 170                 175

Pro Asn Ala Leu Thr Val Ala Ala Ile Asn Lys Ser Asn Ala Arg Ala
            180                 185                 190

Ser Phe Ser Asn Tyr Gly Ser Val Val Asp Ile Phe Ala Pro Gly Gln
        195                 200                 205

Asp Ile Leu Ser Ala Trp Ile Gly Ser Thr Thr Ala Thr Asn Thr Ile
    210                 215                 220

Ser Gly Thr Ser Met Ala Thr Pro His Val Val Gly Leu Ser Val Tyr
225                 230                 235                 240

Leu Met Gly Leu Glu Asn Leu Ser Gly Pro Ala Ala Val Thr Ala Arg
                245                 250                 255

Ile Lys Glu Leu Ala Thr Asn Gly Val Val Thr Asn Val Lys Gly Ser
            260                 265                 270
```

```
Pro Asn Leu Leu Ala Tyr Asn Gly Asn Ala
        275                 280


<210> SEQ ID NO 26
<211> LENGTH: 282
<212> TYPE: PRT
<213> ORGANISM: Artificial Sequence
<220> FEATURE:
<223> OTHER INFORMATION: Synthetic Alkaline Protease (CL00052050)

<400> SEQUENCE: 26

Gly Leu Thr Thr Gln Lys Ser Ala Pro Trp Gly Leu Gly Ser Ile Ser
1               5                   10                  15

His Lys Gly Gln Gly Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ala Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Ile Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 27
<211> LENGTH: 282
<212> TYPE: PRT
<213> ORGANISM: Artificial Sequence
<220> FEATURE:
<223> OTHER INFORMATION: Synthetic Alkaline Protease (CL00052064)

<400> SEQUENCE: 27

Gly Leu Thr Thr Gln Lys Ser Ala Pro Trp Gly Leu Gly Ser Ile Ser
```

```
1               5                   10                  15

His Arg Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 28
<211> LENGTH: 282
<212> TYPE: PRT
<213> ORGANISM: Artificial Sequence
<220> FEATURE:
<223> OTHER INFORMATION: Synthetic Alkaline Protease (CL00052070)

<400> SEQUENCE: 28

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
```

```
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Tyr Gly Lys Val Val Asp Ile Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Val Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 29
<211> LENGTH: 282
<212> TYPE: PRT
<213> ORGANISM: Artificial Sequence
<220> FEATURE:
<223> OTHER INFORMATION: Synthetic Alkaline Protease (CL00052082)

<400> SEQUENCE: 29

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Gly Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
```

```
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 30
<211> LENGTH: 282
<212> TYPE: PRT
<213> ORGANISM: Artificial Sequence
<220> FEATURE:
<223> OTHER INFORMATION: Synthetic Alkaline Protease (CL00052220)

<400> SEQUENCE: 30

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ala Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Val Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Val Val Gly Leu Ser Leu Tyr
225                 230                 235                 240

Leu Ala Ala Leu Glu Asn Leu Asp Gly Pro Ala Ala Val Thr Lys Arg
```

```
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 31
<211> LENGTH: 282
<212> TYPE: PRT
<213> ORGANISM: Artificial Sequence
<220> FEATURE:
<223> OTHER INFORMATION: Synthetic Alkaline Protease (CL00052236)

<400> SEQUENCE: 31

Gly Leu Thr Thr Gln Lys Ser Ala Pro Trp Gly Leu Gly Ser Ile Ser
1               5                   10                  15

His Arg Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Val Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 32
<211> LENGTH: 282
<212> TYPE: PRT
<213> ORGANISM: Artificial Sequence
<220> FEATURE:
<223> OTHER INFORMATION: Synthetic Alkaline Protease (CL00052304)
```

<400> SEQUENCE: 32

```
Gly Leu Thr Thr Gln Lys Ser Ala Pro Trp Gly Leu Gly Ser Ile Ser
1               5                   10                  15

His Lys Gly Gln Gly Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Gly Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280
```

<210> SEQ ID NO 33
<211> LENGTH: 282
<212> TYPE: PRT
<213> ORGANISM: Artificial Sequence
<220> FEATURE:
<223> OTHER INFORMATION: Synthetic Alkaline Protease (CL00052312)

<400> SEQUENCE: 33

```
Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60
```

```
Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Val Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280
```

```
<210> SEQ ID NO 34
<211> LENGTH: 282
<212> TYPE: PRT
<213> ORGANISM: Artificial Sequence
<220> FEATURE:
<223> OTHER INFORMATION: Synthetic Alkaline Protease (CL00052338)

<400> SEQUENCE: 34

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140
```

```
Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Tyr Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 35
<211> LENGTH: 282
<212> TYPE: PRT
<213> ORGANISM: Artificial Sequence
<220> FEATURE:
<223> OTHER INFORMATION: Synthetic Alkaline Protease (CL00052357)

<400> SEQUENCE: 35

Gly Leu Thr Thr Gln Lys Ser Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220
```

```
Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 36
<211> LENGTH: 282
<212> TYPE: PRT
<213> ORGANISM: Artificial Sequence
<220> FEATURE:
<223> OTHER INFORMATION: Synthetic Alkaline Protease (CL00052358)

<400> SEQUENCE: 36

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 37
<211> LENGTH: 282
```

```
<212> TYPE: PRT
<213> ORGANISM: Artificial Sequence
<220> FEATURE:
<223> OTHER INFORMATION: Synthetic Alkaline Protease (CL00052373)

<400> SEQUENCE: 37

Gly Leu Thr Thr Gln Lys Ser Ala Pro Trp Gly Leu Gly Ser Ile Ser
1               5                   10                  15

His Arg Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Val Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 38
<211> LENGTH: 282
<212> TYPE: PRT
<213> ORGANISM: Artificial Sequence
<220> FEATURE:
<223> OTHER INFORMATION: Synthetic Alkaline Protease (CL00052383)

<400> SEQUENCE: 38

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45
```

```
Glu Glu Phe Glu Gly Arg Ala Ser Lys Ala Tyr Asn Ala Ala Gly Gly
    50                  55                  60

Gln His Val Asp Ser Ile Gly His Gly Thr His Val Ala Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Val Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280
```

<210> SEQ ID NO 39
<211> LENGTH: 282
<212> TYPE: PRT
<213> ORGANISM: Artificial Sequence
<220> FEATURE:
<223> OTHER INFORMATION: Synthetic Alkaline Protease (CL00052388)

<400> SEQUENCE: 39

```
Gly Leu Thr Thr Gln Lys Ser Ala Pro Trp Gly Leu Gly Ser Ile Ser
1               5                   10                  15

His Arg Gly Gln Gly Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125
```

```
Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Ile Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Val Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 40
<211> LENGTH: 282
<212> TYPE: PRT
<213> ORGANISM: Artificial Sequence
<220> FEATURE:
<223> OTHER INFORMATION: Synthetic Alkaline Protease (CL00052418)

<400> SEQUENCE: 40

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ala Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205
```

```
Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 41
<211> LENGTH: 282
<212> TYPE: PRT
<213> ORGANISM: Artificial Sequence
<220> FEATURE:
<223> OTHER INFORMATION: Synthetic Alkaline Protease (CL00052440)

<400> SEQUENCE: 41

Gly Leu Thr Thr Gln Lys Ser Ala Pro Trp Gly Leu Gly Ser Ile Ser
1               5                   10                  15

His Arg Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280
```

<210> SEQ ID NO 42
<211> LENGTH: 282
<212> TYPE: PRT
<213> ORGANISM: Artificial Sequence
<220> FEATURE:
<223> OTHER INFORMATION: Synthetic Alkaline Protease (CL00052441)

<400> SEQUENCE: 42

```
Gly Leu Thr Thr Gln Lys Ser Ala Pro Trp Gly Leu Gly Ser Ile Ser
1               5                   10                  15

His Lys Gly Gln Gly Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Phe Gly Lys Val Val Asp Ile Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280
```

<210> SEQ ID NO 43
<211> LENGTH: 282
<212> TYPE: PRT
<213> ORGANISM: Artificial Sequence
<220> FEATURE:
<223> OTHER INFORMATION: Synthetic Alkaline Protease (CL00052473)

<400> SEQUENCE: 43

```
Gly Leu Thr Thr Gln Lys Ser Ala Pro Trp Gly Leu Gly Ser Ile Ser
1               5                   10                  15

His Arg Gly Gln Gln Ser Thr Asp Tyr Ile Tyr Asp Thr Ser Ala Gly
```

```
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Tyr Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 44
<211> LENGTH: 282
<212> TYPE: PRT
<213> ORGANISM: Artificial Sequence
<220> FEATURE:
<223> OTHER INFORMATION: Synthetic Alkaline Protease (CL00052515)

<400> SEQUENCE: 44

Gly Leu Thr Thr Gln Lys Ser Ala Pro Trp Gly Leu Gly Ser Ile Ser
1               5                   10                  15

His Arg Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Val Ala Lys Lys Ala Ser Ile Leu Ser Val
                85                  90                  95

Lys Val Phe Gln Gly Glu Ser Ser Ser Thr Ser Val Ile Leu Asp Gly
```

```
            100                 105                 110

Phe Asn Trp Ala Ala Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
            180                 185                 190

Ser Phe Ser Asn Tyr Gly Lys Val Val Asp Ile Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 45
<211> LENGTH: 282
<212> TYPE: PRT
<213> ORGANISM: Artificial Sequence
<220> FEATURE:
<223> OTHER INFORMATION: Synthetic Alkaline Protease (CL00052530)

<400> SEQUENCE: 45

Gly Leu Thr Thr Gln Lys Ser Ala Pro Trp Gly Leu Gly Ser Ile Ser
1               5                   10                  15

His Lys Gly Gln Gln Ser Thr Asp Tyr Ile Tyr Asp Thr Ser Ala Gly
            20                  25                  30

Glu Gly Thr Tyr Ala Tyr Val Val Asp Ser Gly Val Asn Val Asp His
        35                  40                  45

Glu Glu Phe Glu Gly Arg Ala Ser Lys Ala Tyr Asn Ala Ala Gly Gly
    50                  55                  60

Gln His Val Asp Ser Ile Gly His Gly Thr His Val Ser Gly Thr Ile
65                  70                  75                  80

Ala Gly Lys Thr Tyr Gly Ile Ala Lys Lys Ala Ser Ile Leu Ser Val
                85                  90                  95

Lys Val Phe Gln Gly Glu Ser Ser Ser Thr Ser Val Ile Leu Asp Gly
            100                 105                 110

Phe Asn Trp Ala Val Asn Asp Ile Val Ser Lys Lys Arg Thr Ser Lys
        115                 120                 125

Ala Ala Ile Asn Met Ser Leu Gly Gly Gly Tyr Ser Lys Ala Phe Asn
    130                 135                 140

Asp Ala Val Glu Asn Ala Phe Glu Gln Gly Val Leu Ser Val Val Ala
145                 150                 155                 160

Ala Gly Asn Glu Asn Ser Asp Ala Gly Gln Thr Ser Pro Ala Ser Ala
                165                 170                 175

Pro Asp Ala Ile Thr Val Ala Ala Ile Gln Lys Ser Asn Asn Arg Ala
```

```
            180                 185                 190

Ser Phe Ser Asn Phe Gly Lys Val Val Asp Val Phe Ala Pro Gly Gln
        195                 200                 205

Asp Ile Leu Ser Ala Trp Ile Gly Ser Ser Ser Ala Thr Asn Thr Ile
    210                 215                 220

Ser Gly Thr Ser Met Ala Thr Pro His Ile Val Gly Leu Ser Leu Tyr
225                 230                 235                 240

Leu Ala Ala Leu Glu Asn Leu Asp Gly Pro Ala Ala Val Thr Lys Arg
                245                 250                 255

Ile Lys Glu Leu Ala Thr Lys Asp Val Val Lys Asp Val Lys Gly Ser
            260                 265                 270

Pro Asn Leu Leu Ala Tyr Asn Gly Asn Ala
        275                 280


<210> SEQ ID NO 46
<211> LENGTH: 403
<212> TYPE: PRT
<213> ORGANISM: Artificial Sequence
<220> FEATURE:
<223> OTHER INFORMATION: Alkaline Protease (CL00037296 Nf.AP) (G1P)

<400> SEQUENCE: 46

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Lys Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
```

```
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 47
<211> LENGTH: 403
<212> TYPE: PRT
<213> ORGANISM: Artificial Sequence
<220> FEATURE:
<223> OTHER INFORMATION: Synthetic Alkaline Protease (CL00052543)

<400> SEQUENCE: 47

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220
```

```
Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Gly Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 48
<211> LENGTH: 403
<212> TYPE: PRT
<213> ORGANISM: Artificial Sequence
<220> FEATURE:
<223> OTHER INFORMATION: Synthetic Alkaline Protease (CL00052570)

<400> SEQUENCE: 48

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175
```

```
Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 49
<211> LENGTH: 403
<212> TYPE: PRT
<213> ORGANISM: Artificial Sequence
<220> FEATURE:
<223> OTHER INFORMATION: Synthetic Alkaline Protease (CL00052579)

<400> SEQUENCE: 49

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Gly Ser Thr
```

```
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala


<210> SEQ ID NO 50
<211> LENGTH: 403
<212> TYPE: PRT
<213> ORGANISM: Artificial Sequence
<220> FEATURE:
<223> OTHER INFORMATION: Synthetic Alkaline Protease (CL00052582)

<400> SEQUENCE: 50

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95
```

```
Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Val Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 51
<211> LENGTH: 403
<212> TYPE: PRT
<213> ORGANISM: Artificial Sequence
<220> FEATURE:
<223> OTHER INFORMATION: Synthetic Alkaline Protease (CL00052631)

<400> SEQUENCE: 51

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45
```

```
Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala
```

<210> SEQ ID NO 52
<211> LENGTH: 403
<212> TYPE: PRT
<213> ORGANISM: Artificial Sequence
<220> FEATURE:
<223> OTHER INFORMATION: Synthetic Alkaline Protease (CL00052644)

<400> SEQUENCE: 52

```
Met Leu Ser Ile Lys Arg Thr Leu Leu Leu Leu Gly Ala Val Leu Pro
```

```
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Ala Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Gly Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala
```

<210> SEQ ID NO 53
<211> LENGTH: 403

<212> TYPE: PRT
<213> ORGANISM: Artificial Sequence
<220> FEATURE:
<223> OTHER INFORMATION: Synthetic Alkaline Protease (CL00052649)

<400> SEQUENCE: 53

```
Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Gly Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380
```

```
Gly Val Val Thr Asn Val Lys Gly Ser Pro Asn Lys Leu Ala Tyr Asn
385                 390                 395                 400

Gly Asn Ala


<210> SEQ ID NO 54
<211> LENGTH: 403
<212> TYPE: PRT
<213> ORGANISM: Artificial Sequence
<220> FEATURE:
<223> OTHER INFORMATION: Synthetic Alkaline Protease (CL00052662)

<400> SEQUENCE: 54

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
```

```
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 55
<211> LENGTH: 403
<212> TYPE: PRT
<213> ORGANISM: Artificial Sequence
<220> FEATURE:
<223> OTHER INFORMATION: Synthetic Alkaline Protease (CL00052663)

<400> SEQUENCE: 55

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Gly Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300
```

```
Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 56
<211> LENGTH: 403
<212> TYPE: PRT
<213> ORGANISM: Artificial Sequence
<220> FEATURE:
<223> OTHER INFORMATION: Synthetic Alkaline Protease (CL00052690)

<400> SEQUENCE: 56

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255
```

```
Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 57
<211> LENGTH: 403
<212> TYPE: PRT
<213> ORGANISM: Artificial Sequence
<220> FEATURE:
<223> OTHER INFORMATION: Synthetic Alkaline Protease (CL00052706)

<400> SEQUENCE: 57

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Gly Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
```

```
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Gly Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 58
<211> LENGTH: 403
<212> TYPE: PRT
<213> ORGANISM: Artificial Sequence
<220> FEATURE:
<223> OTHER INFORMATION: Synthetic Alkaline Protease (CL00052720)

<400> SEQUENCE: 58

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175
```

```
Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 59
<211> LENGTH: 403
<212> TYPE: PRT
<213> ORGANISM: Artificial Sequence
<220> FEATURE:
<223> OTHER INFORMATION: Synthetic Alkaline Protease (CL00052745)

<400> SEQUENCE: 59

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125
```

```
Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Ala Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 60
<211> LENGTH: 403
<212> TYPE: PRT
<213> ORGANISM: Artificial Sequence
<220> FEATURE:
<223> OTHER INFORMATION: Synthetic Alkaline Protease (CL00052757)

<400> SEQUENCE: 60

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
```

```
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala


<210> SEQ ID NO 61
<211> LENGTH: 403
<212> TYPE: PRT
<213> ORGANISM: Artificial Sequence
<220> FEATURE:
<223> OTHER INFORMATION: Synthetic Alkaline Protease (CL00052795)

<400> SEQUENCE: 61

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45
```

```
Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala
```

<210> SEQ ID NO 62
<211> LENGTH: 403
<212> TYPE: PRT
<213> ORGANISM: Artificial Sequence
<220> FEATURE:
<223> OTHER INFORMATION: Synthetic Alkaline Protease (CL00052806)

<400> SEQUENCE: 62

```
Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Lys Gly Gln Gly Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala
```

<210> SEQ ID NO 63

<211> LENGTH: 403
<212> TYPE: PRT
<213> ORGANISM: Artificial Sequence
<220> FEATURE:
<223> OTHER INFORMATION: Synthetic Alkaline Protease (CL00052809)

<400> SEQUENCE: 63

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Ser Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385 390 395 400

Gly Asn Ala

<210> SEQ ID NO 64
<211> LENGTH: 403
<212> TYPE: PRT
<213> ORGANISM: Artificial Sequence
<220> FEATURE:
<223> OTHER INFORMATION: Synthetic Alkaline Protease (CL00052822)

<400> SEQUENCE: 64

Met Leu Ser Ile Lys Arg Thr Leu Leu Leu Leu Gly Ala Val Leu Pro
1 5 10 15

Ala Val Phe Gly Ala Pro Val Gln Glu Thr Arg Arg Ala Ala Gln Lys
20 25 30

Ile Pro Gly Lys Tyr Ile Val Thr Phe Lys Pro Gly Thr Asp Thr Ala
35 40 45

Thr Ile Glu Ser His Thr Leu Trp Ala Thr Asp Leu His Lys Arg Asn
50 55 60

Leu Glu Arg Arg Asp Thr Thr Ser Gly Glu Pro Pro Val Gly Ile Glu
65 70 75 80

Lys Ser Tyr Lys Ile Lys Asp Phe Ala Ala Tyr Ala Gly Ser Phe Asp
85 90 95

Asp Ala Thr Ile Glu Glu Ile Arg Lys Arg Gly Asp Val Ala His Val
100 105 110

Glu Glu Asp Gln Ile Trp Tyr Leu Asp Ala Leu Thr Thr Gln Lys Gly
115 120 125

Ala Pro Trp Gly Leu Gly Ser Ile Ser His Arg Gly Gln Gly Ser Thr
130 135 140

Asp Tyr Ile Tyr Asp Thr Ser Ala Gly Ala Gly Thr Tyr Ala Tyr Val
145 150 155 160

Val Asp Ser Gly Ile Asn Val Asn His Val Glu Phe Glu Ser Arg Ala
165 170 175

Ser Leu Gly Tyr Asn Ala Ala Gly Gly Ser His Val Asp Ser Ile Gly
180 185 190

His Gly Thr His Val Ala Gly Thr Ile Gly Gly Lys Thr Tyr Gly Val
195 200 205

Ala Lys Lys Thr Asn Leu Leu Ser Val Lys Val Phe Gln Gly Glu Ser
210 215 220

Ser Ser Thr Ser Ile Ile Leu Asp Gly Phe Asn Trp Ala Val Asn Asp
225 230 235 240

Ile Val Ser Lys Gly Arg Thr Lys Lys Ala Ala Ile Asn Met Ser Leu
245 250 255

Gly Gly Gly Tyr Ser Tyr Ala Phe Asn Asn Ala Val Glu Asn Ala Phe
260 265 270

Asp Glu Gly Val Leu Ser Val Val Ala Ala Gly Asn Glu Asn Ser Asp
275 280 285

Ala Ser Asn Thr Ser Pro Ala Ser Ala Pro Asn Ala Leu Thr Val Ala
290 295 300

Ala Ile Asn Lys Ser Asn Ala Arg Ala Ser Phe Ser Asn Tyr Gly Ser
305 310 315 320

Val Val Asp Ile Phe Ala Pro Gly Gln Asp Ile Leu Ser Ala Trp Ile
325 330 335

```
Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 65
<211> LENGTH: 403
<212> TYPE: PRT
<213> ORGANISM: Artificial Sequence
<220> FEATURE:
<223> OTHER INFORMATION: Synthetic Alkaline Protease (CL00052844)

<400> SEQUENCE: 65

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

His Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Gly Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Val Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
```

```
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Lys Leu Ala Tyr Asn
385                 390                 395                 400

Gly Asn Ala


<210> SEQ ID NO 66
<211> LENGTH: 403
<212> TYPE: PRT
<213> ORGANISM: Artificial Sequence
<220> FEATURE:
<223> OTHER INFORMATION: Synthetic Alkaline Protease (CL00052861)

<400> SEQUENCE: 66

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205

Ala Lys Lys Thr Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Val Ile Asn Met Ser Leu
                245                 250                 255
```

```
Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Ile Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala


<210> SEQ ID NO 67
<211> LENGTH: 403
<212> TYPE: PRT
<213> ORGANISM: Artificial Sequence
<220> FEATURE:
<223> OTHER INFORMATION: Synthetic Alkaline Protease (CL00052875)

<400> SEQUENCE: 67

Met Leu Ser Ile Lys Arg Thr Leu Leu Leu Leu Gly Ala Val Leu Pro
1               5                   10                  15

Ala Val Phe Gly Ala Pro Val Gln Glu Thr Arg Arg Ala Ala Gln Lys
            20                  25                  30

Ile Pro Gly Lys Tyr Ile Val Thr Phe Lys Pro Gly Thr Asp Thr Ala
        35                  40                  45

Thr Ile Glu Ser His Thr Leu Trp Ala Thr Asp Leu His Lys Arg Asn
    50                  55                  60

Leu Glu Arg Arg Asp Thr Thr Ser Gly Glu Pro Pro Val Gly Ile Glu
65                  70                  75                  80

Lys Ser Tyr Lys Ile Lys Asp Phe Ala Ala Tyr Ala Gly Ser Phe Asp
                85                  90                  95

Asp Ala Thr Ile Glu Glu Ile Arg Lys Arg Gly Asp Val Ala His Val
            100                 105                 110

Glu Glu Asp Gln Ile Trp Tyr Leu Asp Ala Leu Thr Thr Gln Lys Gly
        115                 120                 125

Ala Pro Trp Gly Leu Gly Ser Ile Ser His Arg Gly Gln Ala Ser Thr
    130                 135                 140

Asp Tyr Ile Tyr Asp Thr Ser Ala Gly Ala Gly Thr Tyr Ala Tyr Val
145                 150                 155                 160

Val Asp Ser Gly Ile Asn Val Asn His Val Glu Phe Glu Gly Arg Ala
                165                 170                 175

Ser Leu Ala Tyr Asn Ala Ala Gly Gly Ser His Val Asp Ser Ile Gly
            180                 185                 190

His Gly Thr His Val Ala Gly Thr Ile Gly Gly Lys Thr Tyr Gly Val
        195                 200                 205
```

```
Ala Lys Lys Ala Asn Leu Leu Ser Val Lys Val Phe Gln Gly Glu Ser
    210                 215                 220

Ser Ser Thr Ser Ile Ile Leu Asp Gly Phe Asn Trp Ala Val Asn Asp
225                 230                 235                 240

Ile Val Ser Lys Gly Arg Thr Lys Lys Ala Ala Ile Asn Met Ser Leu
                245                 250                 255

Gly Gly Gly Tyr Ser Tyr Ala Phe Asn Asn Ala Val Glu Asn Ala Phe
            260                 265                 270

Asp Glu Gly Val Leu Ser Val Val Ala Ala Gly Asn Glu Asn Ser Asp
        275                 280                 285

Ala Ser Asn Thr Ser Pro Ala Ser Ala Pro Asn Ala Leu Thr Val Ala
    290                 295                 300

Ala Ile Asn Lys Ser Asn Ala Arg Ala Ser Phe Ser Asn Tyr Gly Ser
305                 310                 315                 320

Val Val Asp Ile Phe Ala Pro Gly Gln Asp Ile Leu Ser Ala Trp Ile
                325                 330                 335

Gly Ser Thr Thr Ala Thr Asn Thr Ile Ser Gly Thr Ser Met Ala Thr
            340                 345                 350

Pro His Val Val Gly Leu Ser Val Tyr Leu Met Gly Leu Glu Asn Leu
        355                 360                 365

Ser Gly Pro Ala Ala Val Thr Ala Arg Ile Lys Glu Leu Ala Thr Asn
    370                 375                 380

Gly Val Val Thr Asn Val Lys Gly Ser Pro Asn Leu Leu Ala Tyr Asn
385                 390                 395                 400

Gly Asn Ala


<210> SEQ ID NO 68
<211> LENGTH: 403
<212> TYPE: PRT
<213> ORGANISM: Artificial Sequence
<220> FEATURE:
<223> OTHER INFORMATION: Alkaline Protease (CL00037275 Ao.AP) (G1P)

<400> SEQUENCE: 68

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
```

```
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 69
<211> LENGTH: 403
<212> TYPE: PRT
<213> ORGANISM: Artificial Sequence
<220> FEATURE:
<223> OTHER INFORMATION: Synthetic Alkaline Protease (CL00052050)

<400> SEQUENCE: 69

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125
```

```
Ala Pro Trp Gly Leu Gly Ser Ile Ser His Lys Gly Gln Gly Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ala Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Ile Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

<210> SEQ ID NO 70
<211> LENGTH: 403
<212> TYPE: PRT
<213> ORGANISM: Artificial Sequence
<220> FEATURE:
<223> OTHER INFORMATION: Synthetic Alkaline Protease (CL00052064)

<400> SEQUENCE: 70

```
Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80
```

```
Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 71
<211> LENGTH: 403
<212> TYPE: PRT
<213> ORGANISM: Artificial Sequence
<220> FEATURE:
<223> OTHER INFORMATION: Synthetic Alkaline Protease (CL00052070)

<400> SEQUENCE: 71

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
```

```
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

<210> SEQ ID NO 72
<211> LENGTH: 403
<212> TYPE: PRT
<213> ORGANISM: Artificial Sequence
<220> FEATURE:
<223> OTHER INFORMATION: Synthetic Alkaline Protease (CL00052082)

<400> SEQUENCE: 72

```
Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Gly Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

```
<210> SEQ ID NO 73
<211> LENGTH: 403
<212> TYPE: PRT
<213> ORGANISM: Artificial Sequence
<220> FEATURE:
<223> OTHER INFORMATION: Synthetic Alkaline Protease (CL00052174)

<400> SEQUENCE: 73

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gly Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Gly Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Tyr Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
```

```
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 74
<211> LENGTH: 403
<212> TYPE: PRT
<213> ORGANISM: Artificial Sequence
<220> FEATURE:
<223> OTHER INFORMATION: Synthetic Alkaline Protease (CL00052220)

<400> SEQUENCE: 74

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ala Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Val Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335
```

```
Gly Ser Ser Ser Ala Thr Asn Thr Ile Ser Gly Thr Ser Met Ala Thr
            340                 345                 350

Pro His Val Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 75
<211> LENGTH: 403
<212> TYPE: PRT
<213> ORGANISM: Artificial Sequence
<220> FEATURE:
<223> OTHER INFORMATION: Synthetic Alkaline Protease (CL00052236)

<400> SEQUENCE: 75

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Val Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285
```

```
Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 76
<211> LENGTH: 403
<212> TYPE: PRT
<213> ORGANISM: Artificial Sequence
<220> FEATURE:
<223> OTHER INFORMATION: Synthetic Alkaline Protease (CL00052304)

<400> SEQUENCE: 76

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gly Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Gly Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
```

```
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 77
<211> LENGTH: 403
<212> TYPE: PRT
<213> ORGANISM: Artificial Sequence
<220> FEATURE:
<223> OTHER INFORMATION: Synthetic Alkaline Protease (CL00052312)

<400> SEQUENCE: 77

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205
```

```
Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Val Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 78
<211> LENGTH: 403
<212> TYPE: PRT
<213> ORGANISM: Artificial Sequence
<220> FEATURE:
<223> OTHER INFORMATION: Synthetic Alkaline Protease (CL00052338)

<400> SEQUENCE: 78

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160
```

```
Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Tyr Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 79
<211> LENGTH: 403
<212> TYPE: PRT
<213> ORGANISM: Artificial Sequence
<220> FEATURE:
<223> OTHER INFORMATION: Synthetic Alkaline Protease (CL00052357)

<400> SEQUENCE: 79

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
```

```
        115                 120                 125

Ala Pro Trp Gly Leu Gly Ser Ile Ser His Arg Gly Gln Gly Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 80
<211> LENGTH: 403
<212> TYPE: PRT
<213> ORGANISM: Artificial Sequence
<220> FEATURE:
<223> OTHER INFORMATION: Synthetic Alkaline Protease (CL00052358)

<400> SEQUENCE: 80

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80
```

```
Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

<210> SEQ ID NO 81
<211> LENGTH: 403
<212> TYPE: PRT
<213> ORGANISM: Artificial Sequence
<220> FEATURE:
<223> OTHER INFORMATION: Synthetic Alkaline Protease (CL00052373)

<400> SEQUENCE: 81

```
Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30
```

```
Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Val Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 82
<211> LENGTH: 403
<212> TYPE: PRT
<213> ORGANISM: Artificial Sequence
<220> FEATURE:
<223> OTHER INFORMATION: Synthetic Alkaline Protease (CL00052383)
```

<400> SEQUENCE: 82

```
Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ala Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Val Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

```
<210> SEQ ID NO 83
<211> LENGTH: 403
<212> TYPE: PRT
<213> ORGANISM: Artificial Sequence
<220> FEATURE:
<223> OTHER INFORMATION: Synthetic Alkaline Protease (CL00052388)

<400> SEQUENCE: 83

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gly Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Ile Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Val Val Gly Leu Ser Leu Tyr Leu Ala Ala Leu Glu Asn Leu
        355                 360                 365
```

```
Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 84
<211> LENGTH: 403
<212> TYPE: PRT
<213> ORGANISM: Artificial Sequence
<220> FEATURE:
<223> OTHER INFORMATION: Synthetic Alkaline Protease (CL00052412)

<400> SEQUENCE: 84

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ala Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Gly
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
```

```
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 85
<211> LENGTH: 403
<212> TYPE: PRT
<213> ORGANISM: Artificial Sequence
<220> FEATURE:
<223> OTHER INFORMATION: Synthetic Alkaline Protease (CL00052418)

<400> SEQUENCE: 85

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ala Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285
```

```
Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 86
<211> LENGTH: 403
<212> TYPE: PRT
<213> ORGANISM: Artificial Sequence
<220> FEATURE:
<223> OTHER INFORMATION: Synthetic Alkaline Protease (CL00052440)

<400> SEQUENCE: 86

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240
```

```
Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 87
<211> LENGTH: 403
<212> TYPE: PRT
<213> ORGANISM: Artificial Sequence
<220> FEATURE:
<223> OTHER INFORMATION: Synthetic Alkaline Protease (CL00052441)

<400> SEQUENCE: 87

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gly Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
```

```
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Ile Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 88
<211> LENGTH: 403
<212> TYPE: PRT
<213> ORGANISM: Artificial Sequence
<220> FEATURE:
<223> OTHER INFORMATION: Synthetic Alkaline Protease (CL00052473)

<400> SEQUENCE: 88

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160
```

```
Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Tyr Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

<210> SEQ ID NO 89
<211> LENGTH: 403
<212> TYPE: PRT
<213> ORGANISM: Artificial Sequence
<220> FEATURE:
<223> OTHER INFORMATION: Synthetic Alkaline Protease (CL00052515)

<400> SEQUENCE: 89

```
Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110
```

```
Glu Glu Asp Gln Ile Tyr Tyr Leu Asp Gly Leu Thr Thr Gln Lys Ser
        115                 120                 125

Ala Pro Trp Gly Leu Gly Ser Ile Ser His Arg Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Val
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Ala Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Tyr Gly Lys
305                 310                 315                 320

Val Val Asp Ile Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala


<210> SEQ ID NO 90
<211> LENGTH: 403
<212> TYPE: PRT
<213> ORGANISM: Artificial Sequence
<220> FEATURE:
<223> OTHER INFORMATION: Synthetic Alkaline Protease (CL00052530)

<400> SEQUENCE: 90

Met Gln Ser Ile Lys Arg Thr Leu Leu Leu Leu Gly Ala Ile Leu Pro
1               5                   10                  15

Ala Val Leu Gly Ala Pro Val Gln Glu Thr Arg Arg Ala Ala Glu Lys
            20                  25                  30

Leu Pro Gly Lys Tyr Ile Val Thr Phe Lys Pro Gly Ile Asp Glu Ala
        35                  40                  45

Lys Ile Gln Glu His Thr Thr Trp Ala Thr Asn Ile His Gln Arg Ser
    50                  55                  60

Leu Glu Arg Arg Gly Ala Thr Gly Gly Asp Leu Pro Val Gly Ile Glu
```

```
65                  70                  75                  80

Arg Asn Tyr Lys Ile Asn Lys Phe Ala Ala Tyr Ala Gly Ser Phe Asp
                85                  90                  95

Asp Ala Thr Ile Glu Glu Ile Arg Lys Asn Glu Asp Val Ala Tyr Val
            100                 105                 110

Glu Glu Asp Gln Ile Tyr Tyr Leu Asp Gly Leu Thr Thr Gln Lys Ser
        115                 120                 125

Ala Pro Trp Gly Leu Gly Ser Ile Ser His Lys Gly Gln Gln Ser Thr
    130                 135                 140

Asp Tyr Ile Tyr Asp Thr Ser Ala Gly Glu Gly Thr Tyr Ala Tyr Val
145                 150                 155                 160

Val Asp Ser Gly Val Asn Val Asp His Glu Glu Phe Glu Gly Arg Ala
                165                 170                 175

Ser Lys Ala Tyr Asn Ala Ala Gly Gly Gln His Val Asp Ser Ile Gly
            180                 185                 190

His Gly Thr His Val Ser Gly Thr Ile Ala Gly Lys Thr Tyr Gly Ile
        195                 200                 205

Ala Lys Lys Ala Ser Ile Leu Ser Val Lys Val Phe Gln Gly Glu Ser
    210                 215                 220

Ser Ser Thr Ser Val Ile Leu Asp Gly Phe Asn Trp Ala Val Asn Asp
225                 230                 235                 240

Ile Val Ser Lys Lys Arg Thr Ser Lys Ala Ala Ile Asn Met Ser Leu
                245                 250                 255

Gly Gly Gly Tyr Ser Lys Ala Phe Asn Asp Ala Val Glu Asn Ala Phe
            260                 265                 270

Glu Gln Gly Val Leu Ser Val Val Ala Ala Gly Asn Glu Asn Ser Asp
        275                 280                 285

Ala Gly Gln Thr Ser Pro Ala Ser Ala Pro Asp Ala Ile Thr Val Ala
    290                 295                 300

Ala Ile Gln Lys Ser Asn Asn Arg Ala Ser Phe Ser Asn Phe Gly Lys
305                 310                 315                 320

Val Val Asp Val Phe Ala Pro Gly Gln Asp Ile Leu Ser Ala Trp Ile
                325                 330                 335

Gly Ser Ser Ser Ala Thr Asn Thr Ile Ser Gly Thr Ser Met Ala Thr
            340                 345                 350

Pro His Ile Val Gly Leu Ser Leu Tyr Leu Ala Ala Leu Glu Asn Leu
        355                 360                 365

Asp Gly Pro Ala Ala Val Thr Lys Arg Ile Lys Glu Leu Ala Thr Lys
    370                 375                 380

Asp Val Val Lys Asp Val Lys Gly Ser Pro Asn Leu Leu Ala Tyr Asn
385                 390                 395                 400

Gly Asn Ala
```

<210> SEQ ID NO 91
<211> LENGTH: 846
<212> TYPE: DNA
<213> ORGANISM: Artificial Sequence
<220> FEATURE:
<223> OTHER INFORMATION: Alkaline Protease (CL00037296 Nf.AP) (G1P)

<400> SEQUENCE: 91

```
gccttgacca ctcaaaaggg cgccccatgg ggcctgggca gcatttccca caagggacaa     60

gcaagcaccg actacatcta cgacaccagc gctggcgcag gcacctatgc ctacgttgtc    120

gacagtggca tcaatgtcaa ccacgtcgag ttcgagagcc gcgcatcgct ggcatacaac    180
```

gccgctggtg gcagccatgt tgacagcatc ggccacggaa cgcacgttgc tggaaccatt 240
ggcggcaaga cctacggagt ggccaagaag accaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420
tatgccttca acaacgctgt tgagaacgct ttcgatgaag gtgtcctttc tgtcgtcgct 480
gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcaca ttgttggcct atccgtgtac 720
ttgatgggtc ttgagaacct ctctggccct gctgcagtga ccgctcgcat caaggagctg 780
gccaccaatg gtgttgttac caacgttaag ggcagcccca acaagcttgc ctacaatggc 840
aatgct 846

<210> SEQ ID NO 92
<211> LENGTH: 846
<212> TYPE: DNA
<213> ORGANISM: Artificial Sequence
<220> FEATURE:
<223> OTHER INFORMATION: Synthetic Alkaline Protease (CL00052543)

<400> SEQUENCE: 92
gccttgacca ctcaaaaggg cgccccatgg ggcctgggca gcatttccca cagaggacaa 60
gcaagcaccg actacatcta cgacaccagc gctggcgcag gcacctatgc ctacgttgtc 120
gacagtggca tcaatgtcaa ccacgtcgag ttcgagagcc gcgcatcgct gggttacaac 180
gccgctggtg gcagccatgt tgacagcatc ggccacggaa cgcacgttgc tggaaccatt 240
ggcggcaaga cctacggagt ggccaagaag accaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420
tatgccttca acaacgctgt tgagaacgct ttcgatgaag gtgtcctttc tgtcgtcgct 480
gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcaca ttgttggcct atccgtgtac 720
ttgatgggtc ttgagggtct ctctggccct gctgcagtga ccgctcgcat caaggagctg 780
gccaccaatg gtgttgttac caacgttaag ggcagcccca acaagcttgc ctacaatggc 840
aatgct 846

<210> SEQ ID NO 93
<211> LENGTH: 846
<212> TYPE: PRT
<213> ORGANISM: Artificial Sequence
<220> FEATURE:
<223> OTHER INFORMATION: Synthetic Alkaline Protease (CL00052570)

<400> SEQUENCE: 93

Gly Cys Cys Thr Thr Gly Ala Cys Cys Ala Cys Thr Cys Ala Ala Ala
1 5 10 15

Ala Gly Gly Gly Cys Gly Cys Cys Cys Cys Ala Thr Gly Gly Gly Gly

```
            20                  25                  30

Cys Cys Thr Gly Gly Gly Cys Ala Gly Cys Ala Thr Thr Thr Cys Cys
        35                  40                  45

Cys Ala Cys Ala Gly Ala Gly Gly Ala Cys Ala Ala Gly Cys Ala Ala
    50                  55                  60

Gly Cys Ala Cys Cys Gly Ala Cys Thr Ala Cys Ala Thr Cys Thr Ala
65                  70                  75                  80

Cys Gly Ala Cys Ala Cys Cys Ala Gly Cys Gly Cys Thr Gly Gly Cys
                85                  90                  95

Gly Cys Ala Gly Gly Cys Ala Cys Cys Thr Ala Thr Gly Cys Cys Thr
            100                 105                 110

Ala Cys Gly Thr Thr Gly Thr Cys Gly Ala Cys Ala Gly Thr Gly Gly
        115                 120                 125

Cys Ala Thr Cys Ala Ala Thr Gly Thr Cys Ala Ala Cys Cys Ala Cys
    130                 135                 140

Gly Thr Cys Gly Ala Gly Thr Thr Cys Gly Ala Gly Ala Gly Cys Cys
145                 150                 155                 160

Gly Cys Gly Cys Ala Thr Cys Gly Cys Thr Gly Gly Cys Ala Thr Ala
                165                 170                 175

Cys Ala Ala Cys Gly Cys Cys Gly Cys Thr Gly Gly Thr Gly Gly Cys
            180                 185                 190

Ala Gly Cys Cys Ala Thr Gly Thr Thr Gly Ala Cys Ala Gly Cys Ala
        195                 200                 205

Thr Cys Gly Gly Cys Cys Ala Cys Gly Gly Ala Ala Cys Gly Cys Ala
    210                 215                 220

Cys Gly Thr Thr Gly Cys Thr Gly Gly Ala Ala Cys Cys Ala Thr Thr
225                 230                 235                 240

Gly Gly Cys Gly Gly Cys Ala Ala Gly Ala Cys Cys Thr Ala Cys Gly
                245                 250                 255

Gly Ala Gly Thr Gly Gly Cys Cys Ala Ala Gly Ala Ala Gly Ala Cys
            260                 265                 270

Cys Ala Ala Cys Cys Thr Thr Cys Thr Gly Thr Cys Cys Gly Thr Cys
        275                 280                 285

Ala Ala Gly Gly Thr Cys Thr Thr Cys Cys Ala Gly Gly Gly Cys Gly
    290                 295                 300

Ala Gly Thr Cys Cys Thr Cys Thr Ala Gly Cys Ala Cys Cys Thr Cys
305                 310                 315                 320

Cys Ala Thr Cys Ala Thr Cys Cys Thr Thr Gly Ala Cys Gly Gly Cys
                325                 330                 335

Thr Thr Cys Ala Ala Cys Thr Gly Gly Gly Cys Thr Gly Thr Cys Ala
            340                 345                 350

Ala Thr Gly Ala Cys Ala Thr Thr Gly Thr Gly Ala Gly Cys Ala Ala
        355                 360                 365

Gly Gly Gly Thr Cys Gly Thr Ala Cys Thr Ala Ala Gly Ala Ala Gly
    370                 375                 380

Gly Cys Thr Gly Cys Gly Ala Thr Cys Ala Ala Cys Ala Thr Gly Ala
385                 390                 395                 400

Gly Cys Cys Thr Thr Gly Gly Thr Gly Gly Thr Gly Gly Thr Thr Ala
                405                 410                 415

Cys Thr Cys Thr Thr Ala Thr Gly Cys Cys Thr Thr Cys Ala Ala Cys
            420                 425                 430

Ala Ala Cys Gly Cys Thr Gly Thr Thr Gly Ala Gly Ala Ala Cys Gly
        435                 440                 445
```

```
Cys Thr Thr Thr Cys Gly Ala Thr Gly Ala Ala Gly Gly Thr Gly Thr
    450                 455                 460

Cys Cys Thr Thr Thr Cys Thr Gly Thr Cys Gly Thr Cys Gly Cys Thr
465                 470                 475                 480

Gly Cys Thr Gly Gly Ala Ala Ala Cys Gly Ala Gly Ala Ala Cys Ala
                485                 490                 495

Gly Thr Gly Ala Thr Gly Cys Cys Thr Cys Ala Ala Ala Thr Ala Cys
            500                 505                 510

Cys Ala Gly Cys Cys Cys Thr Gly Cys Thr Thr Cys Cys Gly Cys Thr
        515                 520                 525

Cys Cys Thr Ala Ala Cys Gly Cys Thr Thr Thr Gly Ala Cys Gly Gly
    530                 535                 540

Thr Thr Gly Cys Thr Gly Cys Gly Ala Thr Cys Ala Ala Cys Ala Ala
545                 550                 555                 560

Gly Ala Gly Cys Ala Ala Cys Gly Cys Cys Cys Gly Cys Gly Cys Cys
                565                 570                 575

Thr Cys Cys Thr Thr Cys Thr Cys Cys Ala Ala Cys Thr Ala Thr Gly
            580                 585                 590

Gly Thr Thr Cys Cys Gly Thr Thr Gly Thr Cys Gly Ala Cys Ala Thr
        595                 600                 605

Cys Thr Thr Cys Gly Cys Thr Cys Cys Cys Gly Gly Thr Cys Ala Gly
    610                 615                 620

Gly Ala Thr Ala Thr Cys Cys Thr Thr Thr Cys Gly Gly Cys Cys Thr
625                 630                 635                 640

Gly Gly Ala Thr Thr Gly Gly Cys Thr Cys Cys Ala Cys Cys Ala Cys
                645                 650                 655

Thr Gly Cys Cys Ala Cys Cys Ala Ala Cys Ala Cys Cys Ala Thr Cys
            660                 665                 670

Thr Cys Cys Gly Gly Thr Ala Cys Thr Thr Cys Cys Ala Thr Gly Gly
        675                 680                 685

Cys Cys Ala Cys Cys Cys Cys Thr Cys Ala Cys Gly Thr Cys Gly Thr
    690                 695                 700

Thr Gly Gly Cys Cys Thr Ala Thr Cys Cys Gly Thr Gly Thr Ala Cys
705                 710                 715                 720

Thr Thr Gly Ala Thr Gly Gly Gly Thr Cys Thr Thr Gly Ala Gly Ala
                725                 730                 735

Ala Cys Cys Thr Cys Thr Cys Thr Gly Gly Cys Cys Cys Thr Gly Cys
            740                 745                 750

Thr Gly Cys Ala Gly Thr Gly Ala Cys Cys Gly Cys Thr Cys Gly Cys
        755                 760                 765

Ala Thr Cys Ala Ala Gly Gly Ala Gly Cys Thr Gly Gly Cys Cys Ala
    770                 775                 780

Cys Cys Ala Ala Thr Gly Gly Thr Gly Thr Thr Gly Thr Thr Ala Cys
785                 790                 795                 800

Cys Ala Ala Cys Gly Thr Thr Ala Ala Gly Gly Gly Cys Ala Gly Cys
                805                 810                 815

Cys Cys Cys Ala Ala Cys Ala Ala Gly Cys Thr Thr Gly Cys Cys Thr
            820                 825                 830

Ala Cys Ala Ala Thr Gly Gly Cys Ala Ala Thr Gly Cys Thr
        835                 840                 845
```

<210> SEQ ID NO 94
<211> LENGTH: 846

<212> TYPE: DNA
<213> ORGANISM: Artificial Sequence
<220> FEATURE:
<223> OTHER INFORMATION: Synthetic Alkaline Protease (CL00052579)

<400> SEQUENCE: 94

```
gccttgacca ctcaaaaggg cgccccatgg ggcctgggca gcatttccca cagaggacaa     60

ggtagcaccg actacatcta cgacaccagc gctggcgcag gcacctatgc ctacgttgtc    120

gacagtggca tcaatgtcaa ccacgtcgag ttcgagggtc gcgcatcgct gggttacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acttgcttgc ctacaatggc    840

aatgct                                                               846
```

<210> SEQ ID NO 95
<211> LENGTH: 846
<212> TYPE: PRT
<213> ORGANISM: Artificial Sequence
<220> FEATURE:
<223> OTHER INFORMATION: Synthetic Alkaline Protease (CL00052582)

<400> SEQUENCE: 95

```
Gly Cys Cys Thr Thr Gly Ala Cys Cys Ala Cys Thr Cys Ala Ala Ala
1               5                   10                  15

Ala Gly Gly Gly Cys Gly Cys Cys Cys Cys Ala Thr Gly Gly Gly Gly
            20                  25                  30

Cys Cys Thr Gly Gly Gly Cys Ala Gly Cys Ala Thr Thr Thr Cys Cys
        35                  40                  45

Cys Ala Cys Ala Gly Ala Gly Gly Ala Cys Ala Ala Gly Cys Ala Ala
    50                  55                  60

Gly Cys Ala Cys Cys Gly Ala Cys Thr Ala Cys Ala Thr Cys Thr Ala
65                  70                  75                  80

Cys Gly Ala Cys Ala Cys Cys Ala Gly Cys Gly Cys Thr Gly Gly Cys
                85                  90                  95

Gly Cys Ala Gly Gly Cys Ala Cys Cys Thr Ala Thr Gly Cys Cys Thr
            100                 105                 110

Ala Cys Gly Thr Thr Gly Thr Cys Gly Ala Cys Ala Gly Thr Gly Gly
        115                 120                 125

Cys Ala Thr Cys Ala Ala Thr Gly Thr Cys Ala Ala Cys Cys Ala Cys
    130                 135                 140

Gly Thr Cys Gly Ala Gly Thr Thr Cys Gly Ala Gly Gly Gly Thr Cys
145                 150                 155                 160

Gly Cys Gly Cys Ala Thr Cys Gly Cys Thr Gly Gly Cys Ala Thr Ala
                165                 170                 175
```

```
Cys Ala Ala Cys Gly Cys Cys Gly Cys Thr Gly Gly Thr Gly Gly Cys
            180                 185                 190

Ala Gly Cys Cys Ala Thr Gly Thr Thr Gly Ala Cys Ala Gly Cys Ala
        195                 200                 205

Thr Cys Gly Gly Cys Cys Ala Cys Gly Gly Ala Ala Cys Gly Cys Ala
    210                 215                 220

Cys Gly Thr Thr Gly Cys Thr Gly Gly Ala Ala Cys Cys Ala Thr Thr
225                 230                 235                 240

Gly Gly Cys Gly Gly Cys Ala Ala Gly Ala Cys Cys Thr Ala Cys Gly
                245                 250                 255

Gly Ala Gly Thr Gly Gly Cys Cys Ala Ala Gly Ala Ala Gly Ala Cys
            260                 265                 270

Cys Ala Ala Cys Cys Thr Thr Cys Thr Gly Thr Cys Cys Gly Thr Cys
        275                 280                 285

Ala Ala Gly Gly Thr Cys Thr Thr Cys Cys Ala Gly Gly Gly Cys Gly
    290                 295                 300

Ala Gly Thr Cys Cys Thr Cys Thr Ala Gly Cys Ala Cys Cys Thr Cys
305                 310                 315                 320

Cys Ala Thr Cys Ala Thr Cys Cys Thr Thr Gly Ala Cys Gly Gly Cys
                325                 330                 335

Thr Thr Cys Ala Ala Cys Thr Gly Gly Gly Cys Thr Gly Thr Cys Ala
            340                 345                 350

Ala Thr Gly Ala Cys Ala Thr Thr Gly Thr Gly Ala Gly Cys Ala Ala
        355                 360                 365

Gly Gly Gly Thr Cys Gly Thr Ala Cys Thr Ala Ala Gly Ala Ala Gly
    370                 375                 380

Gly Cys Thr Gly Thr Cys Ala Thr Cys Ala Ala Cys Ala Thr Gly Ala
385                 390                 395                 400

Gly Cys Cys Thr Thr Gly Gly Thr Gly Gly Thr Gly Gly Thr Thr Ala
                405                 410                 415

Cys Thr Cys Thr Thr Ala Thr Gly Cys Cys Thr Thr Cys Ala Ala Cys
            420                 425                 430

Ala Ala Cys Gly Cys Thr Gly Thr Thr Gly Ala Gly Ala Ala Cys Gly
        435                 440                 445

Cys Thr Thr Thr Cys Gly Ala Thr Gly Ala Ala Gly Gly Thr Gly Thr
    450                 455                 460

Cys Cys Thr Thr Thr Cys Thr Gly Thr Cys Gly Thr Cys Gly Cys Thr
465                 470                 475                 480

Gly Cys Thr Gly Gly Ala Ala Ala Cys Gly Ala Gly Ala Ala Cys Ala
                485                 490                 495

Gly Thr Gly Ala Thr Gly Cys Cys Thr Cys Ala Ala Ala Thr Ala Cys
            500                 505                 510

Cys Ala Gly Cys Cys Cys Thr Gly Cys Thr Thr Cys Cys Gly Cys Thr
        515                 520                 525

Cys Cys Thr Ala Ala Cys Gly Cys Thr Thr Thr Gly Ala Cys Gly Gly
    530                 535                 540

Thr Thr Gly Cys Thr Gly Cys Gly Ala Thr Cys Ala Ala Cys Ala Ala
545                 550                 555                 560

Gly Ala Gly Cys Ala Ala Cys Gly Cys Cys Cys Gly Cys Gly Cys Cys
                565                 570                 575

Thr Cys Cys Thr Thr Cys Thr Cys Cys Ala Ala Cys Thr Ala Thr Gly
            580                 585                 590
```

```
Gly Thr Thr Cys Cys Gly Thr Thr Gly Thr Cys Gly Ala Cys Ala Thr
        595                 600                 605

Cys Thr Thr Cys Gly Cys Thr Cys Cys Cys Gly Gly Thr Cys Ala Gly
    610                 615                 620

Gly Ala Thr Ala Thr Cys Cys Thr Thr Thr Cys Gly Gly Cys Cys Thr
625                 630                 635                 640

Gly Gly Ala Thr Thr Gly Gly Cys Thr Cys Cys Ala Cys Cys Ala Cys
                645                 650                 655

Thr Gly Cys Cys Ala Cys Cys Ala Ala Cys Ala Cys Cys Ala Thr Cys
            660                 665                 670

Thr Cys Cys Gly Gly Thr Ala Cys Thr Thr Cys Cys Ala Thr Gly Gly
        675                 680                 685

Cys Cys Ala Cys Cys Cys Cys Thr Cys Ala Cys Gly Thr Cys Gly Thr
    690                 695                 700

Thr Gly Gly Cys Cys Thr Ala Thr Cys Cys Gly Thr Gly Thr Ala Cys
705                 710                 715                 720

Thr Thr Gly Ala Thr Gly Gly Gly Thr Cys Thr Thr Gly Ala Gly Ala
                725                 730                 735

Ala Cys Cys Thr Cys Thr Cys Thr Gly Gly Cys Cys Cys Thr Gly Cys
            740                 745                 750

Thr Gly Cys Ala Gly Thr Gly Ala Cys Cys Gly Cys Thr Cys Gly Cys
        755                 760                 765

Ala Thr Cys Ala Ala Gly Gly Ala Gly Cys Thr Gly Gly Cys Cys Ala
    770                 775                 780

Cys Cys Ala Ala Thr Gly Gly Thr Gly Thr Thr Gly Thr Thr Ala Cys
785                 790                 795                 800

Cys Ala Ala Cys Gly Thr Thr Ala Ala Gly Gly Gly Cys Ala Gly Cys
                805                 810                 815

Cys Cys Cys Ala Ala Cys Ala Ala Gly Cys Thr Thr Gly Cys Cys Thr
            820                 825                 830

Ala Cys Ala Ala Thr Gly Gly Cys Ala Ala Thr Gly Cys Thr
        835                 840                 845
```

<210> SEQ ID NO 96
<211> LENGTH: 846
<212> TYPE: DNA
<213> ORGANISM: Artificial Sequence
<220> FEATURE:
<223> OTHER INFORMATION: Synthetic Alkaline Protease (CL00052631)

<400> SEQUENCE: 96

```
gccttgacca ctcaaaaggg cgccccatgg ggcctgggca gcatttccca cagaggacaa     60

gcaagcaccg actacatcta cgacaccagc gctggcgcag gcacctatgc ctacgttgtc    120

gacagtggca tcaatgtcaa ccacgtcgag ttcgagagcc gcgcatcgct gggttacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660
```

```
accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                               846
```

<210> SEQ ID NO 97
<211> LENGTH: 846
<212> TYPE: DNA
<213> ORGANISM: Artificial Sequence
<220> FEATURE:
<223> OTHER INFORMATION: CL00052644CL00052644)

<400> SEQUENCE: 97

```
gccttgacca ctcaaaaggg cgccccatgg ggcctgggca gcatttccca cagaggacaa     60

gcaagcaccg actacatcta cgacaccagc gctggcgcag gcacctatgc ctacgttgtc    120

gacagtggca tcaatgtcaa ccacgtcgag ttcgagagcc gcgcatcgct ggcatacaac    180

gccgctggtg gcagccatgt tgacagcatc ggccacggaa cgcacgttgc tggaaccatt    240

ggcggcaaga cctacggagt ggccaagaag gctaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcacg tcgttggcct atccgtgtac    720

ttgatgggtc ttgagggtct ctctggccct gctgcagtga ccgctcgcat caaggagctg    780

gccaccaatg gtgttgttac caacgttaag ggcagcccca acttgcttgc ctacaatggc    840

aatgct                                                               846
```

<210> SEQ ID NO 98
<211> LENGTH: 846
<212> TYPE: DNA
<213> ORGANISM: Artificial Sequence
<220> FEATURE:
<223> OTHER INFORMATION: Synthetic Alkaline Protease (CL00052649)

<400> SEQUENCE: 98

```
gccttgacca ctcaaaaggg cgccccatgg ggcctgggca gcatttccca cagaggacaa     60

ggtagcaccg actacatcta cgacaccagc gctggcgcag gcacctatgc ctacgttgtc    120

gacagtggca tcaatgtcaa ccacgtcgag ttcgagagcc gcgcatcgct gggttacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600
```

```
gtcgacatct tcgctcccgg tcaggatatc ctttcggcct ggattggctc caccactgcc    660

accaacacca tctccggtac ttccatggcc acccctcacg tcgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                                846
```

```
<210> SEQ ID NO 99
<211> LENGTH: 846
<212> TYPE: DNA
<213> ORGANISM: Artificial Sequence
<220> FEATURE:
<223> OTHER INFORMATION: Synthetic Alkaline Protease (CL00052662)

<400> SEQUENCE: 99

gccttgacca ctcaaaaggg cgccccatgg ggcctgggca gcatttccca cagaggacaa     60

gcaagcaccg actacatcta cgacaccagc gctggcgcag gcacctatgc ctacgttgtc    120

gacagtggca tcaatgtcaa ccacgtcgag ttcgagggtc gcgcatcgct ggcatacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                                846
```

```
<210> SEQ ID NO 100
<211> LENGTH: 846
<212> TYPE: DNA
<213> ORGANISM: Artificial Sequence
<220> FEATURE:
<223> OTHER INFORMATION: Synthetic Alkaline Protease (CL00052663)

<400> SEQUENCE: 100

gccttgacca ctcaaaaggg cgccccatgg ggcctgggca gcatttccca cagaggacaa     60

ggtagcaccg actacatcta cgacaccagc gctggcgcag gcacctatgc ctacgttgtc    120

gacagtggca tcaatgtcaa ccacgtcgag ttcgagagcc gcgcatcgct ggcatacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600
```

```
gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                               846
```

<210> SEQ ID NO 101
<211> LENGTH: 846
<212> TYPE: DNA
<213> ORGANISM: Artificial Sequence
<220> FEATURE:
<223> OTHER INFORMATION: Synthetic Alkaline Protease (CL00052690)

<400> SEQUENCE: 101

```
gccttgacca ctcaaaaggg cgccccatgg ggcctgggca gcatttccca cagaggacaa     60

gcaagcaccg actacatcta cgacaccagc gctggcgcag gcacctatgc ctacgttgtc    120

gacagtggca tcaatgtcaa ccacgtcgag ttcgagagcc gcgcatcgct ggcatacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                               846
```

<210> SEQ ID NO 102
<211> LENGTH: 846
<212> TYPE: DNA
<213> ORGANISM: Artificial Sequence
<220> FEATURE:
<223> OTHER INFORMATION: Synthetic Alkaline Protease (CL00052706)

<400> SEQUENCE: 102

```
gccttgacca ctcaaaaggg cgccccatgg ggcctgggca gcatttccca cagaggacaa     60

ggtagcaccg actacatcta cgacaccagc gctggcgcag gcacctatgc ctacgttgtc    120

gacagtggca tcaatgtcaa ccacgtcgag ttcgagagcc gcgcatcgct ggcatacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540
```

acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcacg tcgttggcct atccgtgtac 720
ttgatgggtc ttgagggtct ctctggccct gctgcagtga ccgctcgcat caaggagctg 780
gccaccaatg gtgttgttac caacgttaag ggcagcccca acaagcttgc ctacaatggc 840
aatgct 846

<210> SEQ ID NO 103
<211> LENGTH: 846
<212> TYPE: DNA
<213> ORGANISM: Artificial Sequence
<220> FEATURE:
<223> OTHER INFORMATION: Synthetic Alkaline Protease (CL00052720)

<400> SEQUENCE: 103
gccttgacca ctcaaaaggg cgccccatgg ggcctgggca gcatttccca cagaggacaa 60
gcaagcaccg actacatcta cgacaccagc gctggcgcag gcacctatgc ctacgttgtc 120
gacagtggca tcaatgtcaa ccacgtcgag ttcgagggcc gcgcatcgct gggttacaac 180
gccgctggtg gcagccatgt tgacagcatc ggccacggaa cgcacgttgc tggaaccatt 240
ggcggcaaga cctacggagt ggccaagaag accaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420
tatgccttca acaacgctgt tgagaacgct ttcgatgaag gtgtcctttc tgtcgtcgct 480
gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcacg tcgttggcct atccgtgtac 720
ttgatgggtc ttgagaacct ctctggccct gctgcagtga ccgctcgcat caaggagctg 780
gccaccaatg gtgttgttac caacgttaag ggcagcccca acaagcttgc ctacaatggc 840
aatgct 846

<210> SEQ ID NO 104
<211> LENGTH: 846
<212> TYPE: DNA
<213> ORGANISM: Artificial Sequence
<220> FEATURE:
<223> OTHER INFORMATION: Synthetic Alkaline Protease (CL00052745)

<400> SEQUENCE: 104
gccttgacca ctcaaaaggg cgccccatgg ggcctgggca gcatttccca cagaggacaa 60
gcaagcaccg actacatcta cgacaccagc gctggcgcag gcacctatgc ctacgttgtc 120
gacagtggca tcaatgtcaa ccacgtcgag ttcgagggtc gcgcatcgct ggcatacaac 180
gccgctggtg gcagccatgt tgacagcatc ggccacggaa cgcacgttgc tggaaccatt 240
ggcggcaaga cctacggagt ggccaagaag gctaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420
tatgccttca acaacgctgt tgagaacgct ttcgatgaag gtgtcctttc tgtcgtcgct 480
gctggaaacg agaacagtga tgcctcaaat accagccctg cttccgctcc taacgctttg 540

```
acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                                846
```

<210> SEQ ID NO 105
<211> LENGTH: 846
<212> TYPE: DNA
<213> ORGANISM: Artificial Sequence
<220> FEATURE:
<223> OTHER INFORMATION: Synthetic Alkaline Protease (CL00052757)

<400> SEQUENCE: 105

```
gccttgacca ctcaaaaggg cgccccatgg ggcctgggca gcatttccca cagaggacaa     60

gcaagcaccg actacatcta cgacaccagc gctggcgcag gcacctatgc ctacgttgtc    120

gacagtggca tcaatgtcaa ccacgtcgag ttcgagagcc gcgcatcgct gggttacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcacg tcgttggcct atccgtgtac    720

ttgatgggtc ttgagaacct ctctggccct gctgcagtga ccgctcgcat caaggagctg    780

gccaccaatg gtgttgttac caacgttaag ggcagcccca acttgcttgc ctacaatggc    840

aatgct                                                                846
```

<210> SEQ ID NO 106
<211> LENGTH: 846
<212> TYPE: DNA
<213> ORGANISM: Artificial Sequence
<220> FEATURE:
<223> OTHER INFORMATION: Synthetic Alkaline Protease (CL00052795)

<400> SEQUENCE: 106

```
gccttgacca ctcaaaaggg cgccccatgg ggcctgggca gcatttccca cagaggacaa     60

gcaagcaccg actacatcta cgacaccagc gctggcgcag gcacctatgc ctacgttgtc    120

gacagtggca tcaatgtcaa ccacgtcgag ttcgagagcc gcgcatcgct ggcatacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480
```

gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcacg tcgttggcct atccgtgtac 720
ttgatgggtc ttgagaacct ctctggccct gctgcagtga ccgctcgcat caaggagctg 780
gccaccaatg gtgttgttac caacgttaag ggcagcccca acttgcttgc ctacaatggc 840
aatgct 846

<210> SEQ ID NO 107
<211> LENGTH: 846
<212> TYPE: DNA
<213> ORGANISM: Artificial Sequence
<220> FEATURE:
<223> OTHER INFORMATION: Synthetic Alkaline Protease (CL00052806)

<400> SEQUENCE: 107
gccttgacca ctcaaaaggg cgccccatgg ggcctgggca gcatttccca caagggacaa 60
ggaagcaccg actacatcta cgacaccagc gctggcgcag gcacctatgc ctacgttgtc 120
gacagtggca tcaatgtcaa ccacgtcgag ttcgagggtc gcgcatcgct ggcatacaac 180
gccgctggtg gcagccatgt tgacagcatc ggccacggaa cgcacgttgc tggaaccatt 240
ggcggcaaga cctacggagt ggccaagaag accaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420
tatgccttca acaacgctgt tgagaacgct ttcgatgaag gtgtcctttc tgtcgtcgct 480
gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcaca ttgttggcct atccgtgtac 720
ttgatgggtc ttgagaacct ctctggccct gctgcagtga ccgctcgcat caaggagctg 780
gccaccaatg gtgttgttac caacgttaag ggcagcccca acttgcttgc ctacaatggc 840
aatgct 846

<210> SEQ ID NO 108
<211> LENGTH: 846
<212> TYPE: DNA
<213> ORGANISM: Artificial Sequence
<220> FEATURE:
<223> OTHER INFORMATION: Synthetic Alkaline Protease (CL00052809)

<400> SEQUENCE: 108
gccttgacca ctcaaaaggg cgccccatgg ggcctgggca gcatttccca cagaggacaa 60
gcaagcaccg actacatcta cgacaccagc gctggcgcag gcacctatgc ctacgttgtc 120
gacagtggca tcaatgtcaa ccacgtcgag ttcgagagcc gcgcatcgct gggttacaac 180
gccgctggtg gcagccatgt tgacagcatc ggccacggaa cgcacgttgc tggaaccatt 240
ggcggcaaga cctacggagt ggccaagaag accaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420
tatgccttca acaacgctgt tgagaacgct ttcgatgaag gtgtcctttc tgtcgtcgct 480

```
gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acttgcttgc ctacaatggc    840

aatgct                                                               846
```

```
<210> SEQ ID NO 109
<211> LENGTH: 846
<212> TYPE: DNA
<213> ORGANISM: Artificial Sequence
<220> FEATURE:
<223> OTHER INFORMATION: Synthetic Alkaline Protease (CL00052822)

<400> SEQUENCE: 109

gccttgacca ctcaaaaggg cgccccatgg ggcctgggca gcatttccca cagaggacaa     60

ggtagcaccg actacatcta cgacaccagc gctggcgcag gcacctatgc ctacgttgtc    120

gacagtggca tcaatgtcaa ccacgtcgag ttcgagagcc gcgcatcgct gggttacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgcg atcaacatga gccttggtgg tggttactct    420

tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcaca ttgttggcct atccgtgtac    720

ttgatgggtc ttgagaacct ctctggccct gctgcagtga ccgctcgcat caaggagctg    780

gccaccaatg gtgttgttac caacgttaag ggcagcccca acaagcttgc ctacaatggc    840

aatgct                                                               846
```

```
<210> SEQ ID NO 110
<211> LENGTH: 846
<212> TYPE: DNA
<213> ORGANISM: Artificial Sequence
<220> FEATURE:
<223> OTHER INFORMATION: Synthetic Alkaline Protease (CL00052844)

<400> SEQUENCE: 110

gccttgacca ctcaaaaggg cgccccatgg ggcctgggca gcatttccca cagaggacaa     60

gcaagcaccc actacatcta cgacaccagc gctggcgcag gcacctatgc ctacgttgtc    120

gacagtggca tcaatgtcaa ccacgtcgag ttcgagggtc gcgcatcgct gggttacaac    180

gccgctggtg gcagccatgt tgacagcatc ggccacggaa cgcacgttgc tggaaccatt    240

ggcggcaaga cctacggagt ggccaagaag accaaccttc tgtccgtcaa ggtcttccag    300

ggcgagtcct ctagcacctc catcatcctt gacggcttca actgggctgt caatgacatt    360

gtgagcaagg gtcgtactaa gaaggctgtc atcaacatga gccttggtgg tggttactct    420
```

tatgccttca acaacgctgt tgagaacgct ttcgatgaag gtgtcctttc tgtcgtcgct 480
gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcaca ttgttggcct atccgtgtac 720
ttgatgggtc ttgagaacct ctctggccct gctgcagtga ccgctcgcat caaggagctg 780
gccaccaatg gtgttgttac caacgttaag ggcagcccca acaagcttgc ctacaatggc 840
aatgct 846

<210> SEQ ID NO 111
<211> LENGTH: 846
<212> TYPE: DNA
<213> ORGANISM: Artificial Sequence
<220> FEATURE:
<223> OTHER INFORMATION: Synthetic Alkaline Protease (CL00052861)

<400> SEQUENCE: 111
gccttgacca ctcaaaaggg cgccccatgg ggcctgggca gcatttccca cagaggacaa 60
gcaagcaccg actacatcta cgacaccagc gctggcgcag gcacctatgc ctacgttgtc 120
gacagtggca tcaatgtcaa ccacgtcgag ttcgagggtc gcgcatcgct ggcatacaac 180
gccgctggtg gcagccatgt tgacagcatc ggccacggaa cgcacgttgc tggaaccatt 240
ggcggcaaga cctacggagt ggccaagaag accaaccttc tgtccgtcaa ggtcttccag 300
ggcgagtcct ctagcacctc catcatcctt gacggcttca actgggctgt caatgacatt 360
gtgagcaagg gtcgtactaa gaaggctgtc atcaacatga gccttggtgg tggttactct 420
tatgccttca acaacgctgt tgagaacgct ttcgatgaag gtgtcctttc tgtcgtcgct 480
gctggaaacg agaacagtga tgcctcaaat accagccctg cttccgctcc taacgctttg 540
acggttgctg cgatcaacaa gagcaacgcc cgcgcctcct tctccaacta tggttccgtt 600
gtcgacatct tcgctcccgg tcaggatatc ctttcggcct ggattggctc caccactgcc 660
accaacacca tctccggtac ttccatggcc acccctcaca ttgttggcct atccgtgtac 720
ttgatgggtc ttgagaacct ctctggccct gctgcagtga ccgctcgcat caaggagctg 780
gccaccaatg gtgttgttac caacgttaag ggcagcccca acttgcttgc ctacaatggc 840
aatgct 846

<210> SEQ ID NO 112
<211> LENGTH: 846
<212> TYPE: DNA
<213> ORGANISM: Artificial Sequence
<220> FEATURE:
<223> OTHER INFORMATION: Synthetic Alkaline Protease (CL00052875)

<400> SEQUENCE: 112
gccttgacca ctcaaaaggg cgccccatgg ggcctgggca gcatttccca cagaggacaa 60
gcaagcaccg actacatcta cgacaccagc gctggcgcag gcacctatgc ctacgttgtc 120
gacagtggca tcaatgtcaa ccacgtcgag ttcgagggtc gcgcatcgct ggcatacaac 180
gccgctggtg gcagccatgt tgacagcatc ggccacggaa cgcacgttgc tggaaccatt 240
ggcggcaaga cctacggagt ggccaagaag gctaaccttc tgtccgtcaa ggtcttccag 300
ggcgagtcct ctagcacctc catcatcctt gacggcttca actgggctgt caatgacatt 360
gtgagcaagg gtcgtactaa gaaggctgcg atcaacatga gccttggtgg tggttactct 420

```
tatgccttca acaacgctgt tgagaacgct ttcgatgaag gtgtcctttc tgtcgtcgct    480

gctggaaacg agaacagtga tgcctcaaat accagccctg cttccgctcc taacgctttg    540

acggttgctg cgatcaacaa gagcaacgcc cgcgcctcct tctccaacta tggttccgtt    600

gtcgacatct tcgctcccgg tcaggatatc ctttcggcct ggattggctc caccactgcc    660

accaacacca tctccggtac ttccatggcc acccctcacg tcgttggcct atccgtgtac    720

ttgatgggtc ttgagaacct ctctggccct gctgcagtga ccgctcgcat caaggagctg    780

gccaccaatg gtgttgttac caacgttaag ggcagcccca acttgcttgc ctacaatggc    840

aatgct                                                                846
```

<210> SEQ ID NO 113
<211> LENGTH: 846
<212> TYPE: DNA
<213> ORGANISM: Artificial Sequence
<220> FEATURE:
<223> OTHER INFORMATION: Alkaline Protease (CL00037275 Ao.AP) (G1P)

<400> SEQUENCE: 113

```
ggcctgacta cccagaagag tgcccccctgg ggtctgggca gcatttccca caagggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                                846
```

<210> SEQ ID NO 114
<211> LENGTH: 846
<212> TYPE: DNA
<213> ORGANISM: Artificial Sequence
<220> FEATURE:
<223> OTHER INFORMATION: Synthetic Alkaline Protease (CL00052050)

<400> SEQUENCE: 114

```
ggcctgacta cccagaagag tgcccccctgg ggtctgggca gcatttccca caagggccag     60

ggtagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgttgc tggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360
```

gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacatct tcgctcccgg tcaagatatc ctttctgcct ggattggctc ttcctctgcc 660
accaacacca tctctggaac ctccatggct actccccaca ttgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 115
<211> LENGTH: 846
<212> TYPE: DNA
<213> ORGANISM: Artificial Sequence
<220> FEATURE:
<223> OTHER INFORMATION: Synthetic Alkaline Protease (CL00052064)

<400> SEQUENCE: 115
ggcctgacta cccagaagag tgccccctgg ggtctgggca gcatttccca cagaggccag 60
cagagcaccg actacatcta cgacactagt gccggcgagg gcacctatgc ctacgtggtg 120
gatagcggtg tcaatgtcga ccatgaggag ttcgagggcc gcgccagcaa ggcctacaac 180
gctgccggtg gtcagcatgt ggacagcatt ggccatggca cccacgtttc cggcaccatt 240
gctggcaaga cttatggtgt cgccaagaag gccagcatcc tttcggtcaa agttttccag 300
ggtgaatcga gcagcacttc cgtcattctt gacggcttca actgggctgc caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacgtct tcgctcccgg tcaagatatc ctttctgcct ggattggctc ttcctctgcc 660
accaacacca tctctggaac ctccatggct actccccaca ttgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 116
<211> LENGTH: 846
<212> TYPE: DNA
<213> ORGANISM: Artificial Sequence
<220> FEATURE:
<223> OTHER INFORMATION: Synthetic Alkaline Protease (CL00052070)

<400> SEQUENCE: 116
ggcctgacta cccagaagag tgccccctgg ggtctgggca gcatttccca caagggccag 60
cagagcaccg actacatcta cgacactagt gccggcgagg gcacctatgc ctacgtggtg 120
gatagcggtg tcaatgtcga ccatgaggag ttcgagggcc gcgccagcaa ggcctacaac 180
gctgccggtg gtcagcatgt ggacagcatt ggccatggca cccacgtttc cggcaccatt 240
gctggcaaga cttatggtgt cgccaagaag gccagcatcc tttcggtcaa agttttccag 300
ggtgaatcga gcagcacttc cgtcattctt gacggcttca actgggctgc caacgacatt 360

```
gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaacta cggcaaggtc    600

gttgacatct tcgctcccgg tcaagatatc ctttctgcct ggattggctc ttcctctgcc    660

accaacacca tctctggaac ctccatggct actccccacg tcgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

<210> SEQ ID NO 117
<211> LENGTH: 846
<212> TYPE: DNA
<213> ORGANISM: Artificial Sequence
<220> FEATURE:
<223> OTHER INFORMATION: Synthetic Alkaline Protease (CL00052082)

<400> SEQUENCE: 117

```
ggcctgacta cccagaagag tgccccctgg ggtctgggca gcatttccca caagggccag     60

cagagcaccg actacatcta cgacactagt gccggcgagg gcacctatgc ctacgtggtg    120

gatagcggtg tcaatgtcga ccatgaggag ttcgagggcc gcgccagcaa gggttacaac    180

gctgccggtg gtcagcatgt ggacagcatt ggccatggca cccacgtttc cggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

<210> SEQ ID NO 118
<211> LENGTH: 846
<212> TYPE: DNA
<213> ORGANISM: Artificial Sequence
<220> FEATURE:
<223> OTHER INFORMATION: Synthetic Alkaline Protease (CL00052174)

<400> SEQUENCE: 118

```
ggcctgacta cccagaagag tgccccctgg ggtctgggca gcatttccca cagaggccag     60

ggtagcaccg actacatcta cgacactagt gccggcgagg gcacctatgc ctacgtggtg    120

gatagcggtg tcaatgtcga ccatgaggag ttcgagggcc gcgccagcaa gggttacaac    180

gctgccggtg gtcagcatgt ggacagcatt ggccatggca cccacgtttc cggcaccatt    240

gctggcaaga cttatggtgt cgccaagaag gccagcatcc tttcggtcaa agttttccag    300
```

ggtgaatcga gcagcacttc cgtcattctt gacggcttca actgggctgc caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaacta cggcaaggtc 600
gttgacgtct tcgctcccgg tcaagatatc ctttctgcct ggattggctc ttcctctgcc 660
accaacacca tctctggaac ctccatggct actccccaca ttgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 119
<211> LENGTH: 846
<212> TYPE: DNA
<213> ORGANISM: Artificial Sequence
<220> FEATURE:
<223> OTHER INFORMATION: Synthetic Alkaline Protease (CL00052220)

<400> SEQUENCE: 119
ggcctgacta cccagaagag tgccccctgg ggtctgggca gcatttccca caagggccag 60
cagagcaccg actacatcta cgacactagt gccggcgagg gcacctatgc ctacgtggtg 120
gatagcggtg tcaatgtcga ccatgaggag ttcgagggcc gcgccagcaa ggcctacaac 180
gctgccggtg gtcagcatgt ggacagcatt ggccatggca cccacgttgc tggcaccatt 240
gctggcaaga cttatggtat cgccaagaag gccagcatcc tttcggtcaa agttttccag 300
ggtgaatcga gcagcacttc cgtcattctt gacggcttca actgggctgt caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacgtct tcgctcccgg tcaagatatc ctttctgcct ggattggctc ttcctctgcc 660
accaacacca tctctggaac ctccatggct actccccacg tcgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 120
<211> LENGTH: 846
<212> TYPE: DNA
<213> ORGANISM: Artificial Sequence
<220> FEATURE:
<223> OTHER INFORMATION: Synthetic Alkaline Protease (CL00052236)

<400> SEQUENCE: 120
ggcctgacta cccagaagag tgccccctgg ggtctgggca gcatttccca cagaggccag 60
cagagcaccg actacatcta cgacactagt gccggcgagg gcacctatgc ctacgtggtg 120
gatagcggtg tcaatgtcga ccatgaggag ttcgagggcc gcgccagcaa ggcctacaac 180
gctgccggtg gtcagcatgt ggacagcatt ggccatggca cccacgtttc cggcaccatt 240
gctggcaaga cttatggtat cgccaagaag gccagcatcc tttcggtcaa agttttccag 300

```
ggtgaatcga gcagcacttc cgtcattctt gacggcttca actgggctgt caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

<210> SEQ ID NO 121
<211> LENGTH: 846
<212> TYPE: DNA
<213> ORGANISM: Artificial Sequence
<220> FEATURE:
<223> OTHER INFORMATION: Synthetic Alkaline Protease (CL00052304)

<400> SEQUENCE: 121

```
ggcctgacta cccagaagag tgccccctgg ggtctgggca gcatttccca caagggccag     60

ggtagcaccg actacatcta cgacactagt gccggcgagg gcacctatgc ctacgtggtg    120

gatagcggtg tcaatgtcga ccatgaggag ttcgagggcc gcgccagcaa gggttacaac    180

gctgccggtg gtcagcatgt ggacagcatt ggccatggca cccacgtttc cggcaccatt    240

gctggcaaga cttatggtgt cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

<210> SEQ ID NO 122
<211> LENGTH: 846
<212> TYPE: DNA
<213> ORGANISM: Artificial Sequence
<220> FEATURE:
<223> OTHER INFORMATION: Synthetic Alkaline Protease (CL00052312)

<400> SEQUENCE: 122

```
ggcctgacta cccagaagag tgccccctgg ggtctgggca gcatttccca caagggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240
```

```
gctggcaaga cttatggtgt cgccaagaag gccagcatcc tttcggtcaa agttttccag    300

ggtgaatcga gcagcacttc cgtcattctt gacggcttca actgggctgt caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

```
<210> SEQ ID NO 123
<211> LENGTH: 846
<212> TYPE: DNA
<213> ORGANISM: Artificial Sequence
<220> FEATURE:
<223> OTHER INFORMATION: Synthetic Alkaline Protease (CL00052338)

<400> SEQUENCE: 123

ggcctgacta cccagaagag tgccccctgg ggtctgggca gcatttccca caagggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtgt cgccaagaag gccagcatcc tttcggtcaa agtttttccag   300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaacta cggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846

<210> SEQ ID NO 124
<211> LENGTH: 846
<212> TYPE: DNA
<213> ORGANISM: Artificial Sequence
<220> FEATURE:
<223> OTHER INFORMATION: Synthetic Alkaline Protease (CL00052357)

<400> SEQUENCE: 124

ggcctgacta cccagaagag tgccccctgg ggtctgggca gcatttccca cagaggccag     60

ggtagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240
```

```
gctggcaaga cttatggtgt cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

<210> SEQ ID NO 125
<211> LENGTH: 846
<212> TYPE: DNA
<213> ORGANISM: Artificial Sequence
<220> FEATURE:
<223> OTHER INFORMATION: Synthetic Alkaline Protease (CL00052358)

<400> SEQUENCE: 125

```
ggcctgacta cccagaagag tgccccctgg ggtctgggca gcatttccca caagggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtgt cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

<210> SEQ ID NO 126
<211> LENGTH: 846
<212> TYPE: DNA
<213> ORGANISM: Artificial Sequence
<220> FEATURE:
<223> OTHER INFORMATION: Synthetic Alkaline Protease (CL00052373)

<400> SEQUENCE: 126

```
ggcctgacta cccagaagag tgccccctgg ggtctgggca gcatttccca cagaggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180
```

gctgccggtg gtcagcatgt ggacagcatt ggccatggca cccacgtttc cggcaccatt 240
gctggcaaga cttatggtat cgccaagaag gccagcatcc tttcggtcaa agttttccag 300
ggtgaatcga gcagcacttc cgtcattctt gacggcttca actgggctgc caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacgtct tcgctcccgg tcaagatatc ctttctgcct ggattggctc ttcctctgcc 660
accaacacca tctctggaac ctccatggct actccccacg tcgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 127
<211> LENGTH: 846
<212> TYPE: DNA
<213> ORGANISM: Artificial Sequence
<220> FEATURE:
<223> OTHER INFORMATION: Synthetic Alkaline Protease (CL00052383)

<400> SEQUENCE: 127
ggcctgacta cccagaagag tgccccctgg ggtctgggca gcatttccca caagggccag 60
cagagcaccg actacatcta cgacactagt gccggcgagg gcacctatgc ctacgtggtg 120
gatagcggtg tcaatgtcga ccatgaggag ttcgagggcc gcgccagcaa ggcctacaac 180
gctgccggtg gtcagcatgt ggacagcatt ggccatggca cccacgttgc tggcaccatt 240
gctggcaaga cttatggtgt cgccaagaag gccagcatcc tttcggtcaa agttttccag 300
ggtgaatcga gcagcacttc cgtcattctt gacggcttca actgggctgt caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacgtct tcgctcccgg tcaagatatc ctttctgcct ggattggctc ttcctctgcc 660
accaacacca tctctggaac ctccatggct actccccaca ttgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 128
<211> LENGTH: 846
<212> TYPE: DNA
<213> ORGANISM: Artificial Sequence
<220> FEATURE:
<223> OTHER INFORMATION: Synthetic Alkaline Protease (CL00052388)

<400> SEQUENCE: 128
ggcctgacta cccagaagag tgccccctgg ggtctgggca gcatttccca cagaggccag 60
ggtagcaccg actacatcta cgacactagt gccggcgagg gcacctatgc ctacgtggtg 120
gatagcggtg tcaatgtcga ccatgaggag ttcgagggcc gcgccagcaa ggcctacaac 180

```
gctgccggtg gtcagcatgt ggacagcatt ggccatggca cccacgtttc cggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacatct tcgctcccgg tcaagatatc ctttctgcct ggattggctc ttcctctgcc    660

accaacacca tctctggaac ctccatggct actccccacg tcgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

```
<210> SEQ ID NO 129
<211> LENGTH: 846
<212> TYPE: DNA
<213> ORGANISM: Artificial Sequence
<220> FEATURE:
<223> OTHER INFORMATION: Synthetic Alkaline Protease (CL00052412)

<400> SEQUENCE: 129

ggcctgacta cccagaagag tgccccctgg ggtctgggca gcatttccca cagaggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgttgc tggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttggtg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

```
<210> SEQ ID NO 130
<211> LENGTH: 846
<212> TYPE: DNA
<213> ORGANISM: Artificial Sequence
<220> FEATURE:
<223> OTHER INFORMATION: Synthetic Alkaline Protease (CL00052418)

<400> SEQUENCE: 130

ggcctgacta cccagaagag tgccccctgg ggtctgggca gcatttccca caagggccag     60

cagagcaccg actacatcta cgacactagt gccggcgagg gcacctatgc ctacgtggtg    120
```

gatagcggtg tcaatgtcga ccatgaggag ttcgagggcc gcgccagcaa ggcctacaac 180
gctgccggtg gtcagcatgt ggacagcatt ggccatggca cccacgttgc tggcaccatt 240
gctggcaaga cttatggtat cgccaagaag gccagcatcc tttcggtcaa agttttccag 300
ggtgaatcga gcagcacttc cgtcattctt gacggcttca actgggctgc caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacgtct tcgctcccgg tcaagatatc ctttctgcct ggattggctc ttcctctgcc 660
accaacacca tctctggaac ctccatggct actccccaca ttgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 131
<211> LENGTH: 846
<212> TYPE: DNA
<213> ORGANISM: Artificial Sequence
<220> FEATURE:
<223> OTHER INFORMATION: Synthetic Alkaline Protease (CL00052440)

<400> SEQUENCE: 131
ggcctgacta cccagaagag tgccccctgg ggtctgggca gcatttccca cagaggccag 60
cagagcaccg actacatcta cgacactagt gccggcgagg gcacctatgc ctacgtggtg 120
gatagcggtg tcaatgtcga ccatgaggag ttcgagggcc gcgccagcaa ggcctacaac 180
gctgccggtg gtcagcatgt ggacagcatt ggccatggca cccacgtttc cggcaccatt 240
gctggcaaga cttatggtat cgccaagaag gccagcatcc tttcggtcaa agttttccag 300
ggtgaatcga gcagcacttc cgtcattctt gacggcttca actgggctgc caacgacatt 360
gttagcaaga agcgtaccag caaggctgca atcaacatga gcttgggcgg tggctactct 420
aaggctttca acgatgcggt cgagaacgca ttcgagcagg gtgttctctc ggttgtcgct 480
gccggtaacg agaactctga tgccggccaa accagccctg cctctgcccc tgatgccatc 540
actgttgccg ctatccagaa gagcaacaac cgcgccagtt tctccaactt tggcaaggtc 600
gttgacgtct tcgctcccgg tcaagatatc ctttctgcct ggattggctc ttcctctgcc 660
accaacacca tctctggaac ctccatggct actccccaca ttgtcggcct gtccctctac 720
ctcgctgccc ttgagaacct cgatggcccc gctgccgtga ccaagcgcat caaggagttg 780
gccaccaagg acgtcgtcaa ggatgttaag ggcagcccta acctgcttgc ctacaacggt 840
aacgct 846

<210> SEQ ID NO 132
<211> LENGTH: 846
<212> TYPE: DNA
<213> ORGANISM: Artificial Sequence
<220> FEATURE:
<223> OTHER INFORMATION: Synthetic Alkaline Protease (CL00052441)

<400> SEQUENCE: 132
ggcctgacta cccagaagag tgccccctgg ggtctgggca gcatttccca caagggccag 60
ggtagcaccg actacatcta cgacactagt gccggcgagg gcacctatgc ctacgtggtg 120

```
gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacatct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

```
<210> SEQ ID NO 133
<211> LENGTH: 846
<212> TYPE: DNA
<213> ORGANISM: Artificial Sequence
<220> FEATURE:
<223> OTHER INFORMATION: Synthetic Alkaline Protease (CL00052473)

<400> SEQUENCE: 133

ggcctgacta cccagaagag tgccccctgg ggtctgggca gcatttccca cagaggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtat cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaacta cggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846

<210> SEQ ID NO 134
<211> LENGTH: 846
<212> TYPE: DNA
<213> ORGANISM: Artificial Sequence
<220> FEATURE:
<223> OTHER INFORMATION: Synthetic Alkaline Protease (CL00052515)

<400> SEQUENCE: 134

ggcctgacta cccagaagag tgccccctgg ggtctgggca gcatttccca cagaggccag     60
```

```
cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtgt cgccaagaag gccagcatcc tttcggtcaa agttttccag    300

ggtgaatcga gcagcacttc cgtcattctt gacggcttca actgggctgc caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaacta cggcaaggtc    600

gttgacatct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

```
<210> SEQ ID NO 135
<211> LENGTH: 846
<212> TYPE: DNA
<213> ORGANISM: Artificial Sequence
<220> FEATURE:
<223> OTHER INFORMATION: Synthetic Alkaline Protease (CL00052530)

<400> SEQUENCE: 135

ggcctgacta cccagaagag tgccccctgg ggtctgggca gcatttccca caagggccag     60

cagagcaccg actacatcta cgacactagt gccggcgagg gcacctatgc ctacgtggtg    120

gatagcggtg tcaatgtcga ccatgaggag ttcgagggcc gcgccagcaa ggcctacaac    180

gctgccggtg gtcagcatgt ggacagcatt ggccatggca cccacgtttc cggcaccatt    240

gctggcaaga cttatggtat cgccaagaag gccagcatcc tttcggtcaa agttttccag    300

ggtgaatcga gcagcacttc cgtcattctt gacggcttca actgggctgt caacgacatt    360

gttagcaaga agcgtaccag caaggctgca atcaacatga gcttgggcgg tggctactct    420

aaggctttca acgatgcggt cgagaacgca ttcgagcagg gtgttctctc ggttgtcgct    480

gccggtaacg agaactctga tgccggccaa accagccctg cctctgcccc tgatgccatc    540

actgttgccg ctatccagaa gagcaacaac cgcgccagtt tctccaactt tggcaaggtc    600

gttgacgtct tcgctcccgg tcaagatatc ctttctgcct ggattggctc ttcctctgcc    660

accaacacca tctctggaac ctccatggct actccccaca ttgtcggcct gtccctctac    720

ctcgctgccc ttgagaacct cgatggcccc gctgccgtga ccaagcgcat caaggagttg    780

gccaccaagg acgtcgtcaa ggatgttaag ggcagcccta acctgcttgc ctacaacggt    840

aacgct                                                               846
```

```
<210> SEQ ID NO 136
<211> LENGTH: 1209
<212> TYPE: DNA
<213> ORGANISM: Artificial Sequence
<220> FEATURE:
<223> OTHER INFORMATION: Alkaline Protease (CL00037296 Nf.AP) (G1P)

<400> SEQUENCE: 136

atgctttcta tcaaacgcac tttgctgctc cttggagctg tcctgccagc cgtctttggc     60
```

gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacaaggga 420
caagcaagca ccgactacat ctacgacacc agcgctggcg caggcaccta tgcctacgtt 480
gtcgacagtg gcatcaatgt caaccacgtc gagttcgaga gccgcgcatc gctggcatac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acattgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 137
<211> LENGTH: 1209
<212> TYPE: DNA
<213> ORGANISM: Artificial Sequence
<220> FEATURE:
<223> OTHER INFORMATION: Synthetic Alkaline Protease (CL00052543)

<400> SEQUENCE: 137
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgaga gccgcgcatc gctgggttac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acattgttgg cctatccgtg 1080
tacttgatgg gtcttgaggg tctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 138
<211> LENGTH: 1209
<212> TYPE: DNA
<213> ORGANISM: Artificial Sequence
<220> FEATURE:
<223> OTHER INFORMATION: Synthetic Alkaline Protease (CL00052570)

<400> SEQUENCE: 138
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgaga gccgcgcatc gctggcatac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acgtcgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 139
<211> LENGTH: 1209
<212> TYPE: DNA
<213> ORGANISM: Artificial Sequence
<220> FEATURE:
<223> OTHER INFORMATION: Synthetic Alkaline Protease (CL00052579)

<400> SEQUENCE: 139
atgctttcta tcaaacgcac tttgctgctc cttggagctg tcctgccagc cgtctttggc 60
gcgcctgtcc aggaaactcg tcgtgctgct caaaagattc ctggcaagta catcgtgacc 120

```
ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caaggtagca ccgactacat ctacgacacc agcgctggcg caggcaccta tgcctacgtt    480

gtcgacagtg gcatcaatgt caaccacgtc gagttcgagg gtcgcgcatc gctgggttac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacttgct tgcctacaat   1200

ggcaatgct                                                           1209
```

<210> SEQ ID NO 140
<211> LENGTH: 1209
<212> TYPE: DNA
<213> ORGANISM: Artificial Sequence
<220> FEATURE:
<223> OTHER INFORMATION: Synthetic Alkaline Protease (CL00052582)

<400> SEQUENCE: 140

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgagg gtcgcgcatc gctggcatac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gtcatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900
```

```
ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acgtcgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacaagct tgcctacaat   1200

ggcaatgct                                                           1209
```

<210> SEQ ID NO 141
<211> LENGTH: 1209
<212> TYPE: DNA
<213> ORGANISM: Artificial Sequence
<220> FEATURE:
<223> OTHER INFORMATION: Synthetic Alkaline Protease (CL00052631)

<400> SEQUENCE: 141

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgaga gccgcgcatc gctgggttac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacaagct tgcctacaat   1200

ggcaatgct                                                           1209
```

<210> SEQ ID NO 142
<211> LENGTH: 1209
<212> TYPE: DNA
<213> ORGANISM: Artificial Sequence
<220> FEATURE:
<223> OTHER INFORMATION: Synthetic Alkaline Protease (CL00052644)

<400> SEQUENCE: 142

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180
```

```
cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgaga gccgcgcatc gctggcatac    540

aacgccgctg gtggcagcca tgttgacagc atcggccacg gaacgcacgt tgctggaacc    600

attggcggca agacctacgg agtggccaag aaggctaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acgtcgttgg cctatccgtg   1080

tacttgatgg gtcttgaggg tctctctggc cctgctgcag tgaccgctcg catcaaggag   1140

ctggccacca atggtgttgt taccaacgtt aagggcagcc ccaacttgct tgcctacaat   1200

ggcaatgct                                                           1209
```

```
<210> SEQ ID NO 143
<211> LENGTH: 1209
<212> TYPE: DNA
<213> ORGANISM: Artificial Sequence
<220> FEATURE:
<223> OTHER INFORMATION: Synthetic Alkaline Protease (CL00052649)

<400> SEQUENCE: 143
```

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caaggtagca ccgactacat ctacgacacc agcgctggcg caggcaccta tgcctacgtt    480

gtcgacagtg gcatcaatgt caaccacgtc gagttcgaga gccgcgcatc gctgggttac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960
```

gttgtcgaca tcttcgctcc cggtcaggat atcctttcgg cctggattgg ctccaccact 1020
gccaccaaca ccatctccgg tacttccatg gccacccctc acgtcgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 144
<211> LENGTH: 1209
<212> TYPE: DNA
<213> ORGANISM: Artificial Sequence
<220> FEATURE:
<223> OTHER INFORMATION: Synthetic Alkaline Protease (CL00052662)

<400> SEQUENCE: 144
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgagg gtcgcgcatc gctggcatac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acattgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 145
<211> LENGTH: 1209
<212> TYPE: DNA
<213> ORGANISM: Artificial Sequence
<220> FEATURE:
<223> OTHER INFORMATION: Synthetic Alkaline Protease (CL00052663)

<400> SEQUENCE: 145
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240

```
aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caaggtagca ccgactacat ctacgacacc agcgctggcg caggcaccta tgcctacgtt    480

gtcgacagtg gcatcaatgt caaccacgtc gagttcgaga gccgcgcatc gctggcatac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacaagct tgcctacaat   1200

ggcaatgct                                                           1209
```

<210> SEQ ID NO 146
<211> LENGTH: 1209
<212> TYPE: DNA
<213> ORGANISM: Artificial Sequence
<220> FEATURE:
<223> OTHER INFORMATION: Synthetic Alkaline Protease (CL00052690)

<400> SEQUENCE: 146

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgaga gccgcgcatc gctggcatac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020
```

gccaccaaca ccatctccgg tacttccatg gccacccctc acattgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 147
<211> LENGTH: 1209
<212> TYPE: DNA
<213> ORGANISM: Artificial Sequence
<220> FEATURE:
<223> OTHER INFORMATION: Synthetic Alkaline Protease (CL00052706)

<400> SEQUENCE: 147
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caaggtagca ccgactacat ctacgacacc agcgctggcg caggcaccta tgcctacgtt 480
gtcgacagtg gcatcaatgt caaccacgtc gagttcgaga gccgcgcatc gctggcatac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acgtcgttgg cctatccgtg 1080
tacttgatgg gtcttgaggg tctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 148
<211> LENGTH: 1209
<212> TYPE: DNA
<213> ORGANISM: Artificial Sequence
<220> FEATURE:
<223> OTHER INFORMATION: Synthetic Alkaline Protease (CL00052720)

<400> SEQUENCE: 148
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300

```
gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgagg gccgcgcatc gctgggttac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acgtcgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacaagct tgcctacaat   1200

ggcaatgct                                                           1209
```

```
<210> SEQ ID NO 149
<211> LENGTH: 1209
<212> TYPE: DNA
<213> ORGANISM: Artificial Sequence
<220> FEATURE:
<223> OTHER INFORMATION: Synthetic Alkaline Protease (CL00052745)

<400> SEQUENCE: 149

atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgagg gtcgcgcatc gctggcatac    540

aacgccgctg gtggcagcca tgttgacagc atcggccacg gaacgcacgt tgctggaacc    600

attggcggca agacctacgg agtggccaag aaggctaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080
```

tacttgatgg gtcttgagaa cctctctggc cctgctgcag tgaccgctcg catcaaggag 1140
ctggccacca atggtgttgt taccaacgtt aagggcagcc ccaacaagct tgcctacaat 1200
ggcaatgct 1209

<210> SEQ ID NO 150
<211> LENGTH: 1209
<212> TYPE: DNA
<213> ORGANISM: Artificial Sequence
<220> FEATURE:
<223> OTHER INFORMATION: Synthetic Alkaline Protease (CL00052757)

<400> SEQUENCE: 150
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgaga gccgcgcatc gctgggttac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acgtcgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacttgct tgcctacaat 1200
ggcaatgct 1209

<210> SEQ ID NO 151
<211> LENGTH: 1209
<212> TYPE: DNA
<213> ORGANISM: Artificial Sequence
<220> FEATURE:
<223> OTHER INFORMATION: Synthetic Alkaline Protease (CL00052795)

<400> SEQUENCE: 151
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360

```
gacgccttga ccactcaaaa gggcgcccca tggggcctgg gcagcatttc ccacagagga    420

caagcaagca ccgactacat ctacgacacc agcgctggcg caggcaccta tgcctacgtt    480

gtcgacagtg gcatcaatgt caaccacgtc gagttcgaga gccgcgcatc gctggcatac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acgtcgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacttgct tgcctacaat   1200

ggcaatgct                                                           1209
```

<210> SEQ ID NO 152
<211> LENGTH: 1209
<212> TYPE: DNA
<213> ORGANISM: Artificial Sequence
<220> FEATURE:
<223> OTHER INFORMATION: Synthetic Alkaline Protease (CL00052806)

<400> SEQUENCE: 152

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacaaggga    420

caaggaagca ccgactacat ctacgacacc agcgctggcg caggcaccta tgcctacgtt    480

gtcgacagtg gcatcaatgt caaccacgtc gagttcgagg gtcgcgcatc gctggcatac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080

tacttgatgg gtcttgagaa cctctctggc cctgctgcag tgaccgctcg catcaaggag   1140
```

ctggccacca atggtgttgt taccaacgtt aagggcagcc ccaacttgct tgcctacaat 1200
ggcaatgct 1209

<210> SEQ ID NO 153
<211> LENGTH: 1209
<212> TYPE: DNA
<213> ORGANISM: Artificial Sequence
<220> FEATURE:
<223> OTHER INFORMATION: Synthetic Alkaline Protease (CL00052809)

<400> SEQUENCE: 153
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgaga gccgcgcatc gctgggttac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acattgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacttgct tgcctacaat 1200
ggcaatgct 1209

<210> SEQ ID NO 154
<211> LENGTH: 1209
<212> TYPE: DNA
<213> ORGANISM: Artificial Sequence
<220> FEATURE:
<223> OTHER INFORMATION: Synthetic Alkaline Protease (CL00052822)

<400> SEQUENCE: 154
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420

```
caaggtagca ccgactacat ctacgacacc agcgctggcg caggcaccta tgcctacgtt    480

gtcgacagtg gcatcaatgt caaccacgtc gagttcgaga gccgcgcatc gctgggttac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gcgatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacaagct tgcctacaat   1200

ggcaatgct                                                           1209
```

<210> SEQ ID NO 155
<211> LENGTH: 1209
<212> TYPE: DNA
<213> ORGANISM: Artificial Sequence
<220> FEATURE:
<223> OTHER INFORMATION: Synthetic Alkaline Protease (CL00052844)

<400> SEQUENCE: 155

```
atgctttcta tcaaacgcac tttgctgctc cttggagctg tcctgccagc cgtctttggc     60

gcgcctgtcc aggaaactcg tcgtgctgct cagaagattc ctggcaagta catcgtgacc    120

ttcaagccgg gcaccgatac agctaccatt gagtctcaca ctctttgggc cactgatctt    180

cacaaacgca atctggagcg tcgtgatacc actagcggcg aacctcccgt cggtatcgag    240

aagagctaca agatcaagga tttcgccgcc tacgctggct ccttcgatga cgccaccatc    300

gaggaaatcc gcaagagggg agacgttgcc catgttgagg aggaccaaat ctggtatctt    360

gacgccttga ccactcaaaa gggcgcccca tggggcctgg gcagcatttc ccacagagga    420

caagcaagca cccactacat ctacgacacc agcgctggcg caggcaccta tgcctacgtt    480

gtcgacagtg gcatcaatgt caaccacgtc gagttcgagg gtcgcgcatc gctgggttac    540

aacgccgctg gtggcagcca tgttgacagc atcggccacg gaacgcacgt tgctggaacc    600

attggcggca agacctacgg agtggccaag aagaccaacc ttctgtccgt caaggtcttc    660

cagggcgagt cctctagcac ctccatcatc cttgacggct tcaactgggc tgtcaatgac    720

attgtgagca agggtcgtac taagaaggct gtcatcaaca tgagccttgg tggtggttac    780

tcttatgcct tcaacaacgc tgttgagaac gctttcgatg aaggtgtcct ttctgtcgtc    840

gctgctggaa acgagaacag tgatgcctca aataccagcc ctgcttccgc tcctaacgct    900

ttgacggttg ctgcgatcaa caagagcaac gcccgcgcct ccttctccaa ctatggttcc    960

gttgtcgaca tcttcgctcc cggtcaggat atcctttcgg cctggattgg ctccaccact   1020

gccaccaaca ccatctccgg tacttccatg gccacccctc acattgttgg cctatccgtg   1080

tacttgatgg gtcttgagaa cctctctggc cctgctgcag tgaccgctcg catcaaggag   1140

ctggccacca atggtgttgt taccaacgtt aagggcagcc ccaacaagct tgcctacaat   1200
```

ggcaatgct 1209

<210> SEQ ID NO 156
<211> LENGTH: 1209
<212> TYPE: DNA
<213> ORGANISM: Artificial Sequence
<220> FEATURE:
<223> OTHER INFORMATION: Synthetic Alkaline Protease (CL00052861)

<400> SEQUENCE: 156
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgagg gtcgcgcatc gctggcatac 540
aacgccgctg gtggcagcca tgttgacagc atcggccacg gaacgcacgt tgctggaacc 600
attggcggca agacctacgg agtggccaag aagaccaacc ttctgtccgt caaggtcttc 660
cagggcgagt cctctagcac ctccatcatc cttgacggct tcaactgggc tgtcaatgac 720
attgtgagca agggtcgtac taagaaggct gtcatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acattgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacttgct tgcctacaat 1200
ggcaatgct 1209

<210> SEQ ID NO 157
<211> LENGTH: 1209
<212> TYPE: DNA
<213> ORGANISM: Artificial Sequence
<220> FEATURE:
<223> OTHER INFORMATION: Synthetic Alkaline Protease (CL00052875)

<400> SEQUENCE: 157
atgctttcta tcaaacgcac tttgctgctc cttggagctg tcctgccagc cgtctttggc 60
gcgcctgtcc aggaaactcg tcgtgctgct cagaagattc ctggcaagta catcgtgacc 120
ttcaagccgg gcaccgatac agctaccatt gagtctcaca ctctttgggc cactgatctt 180
cacaaacgca atctggagcg tcgtgatacc actagcggcg aacctcccgt cggtatcgag 240
aagagctaca agatcaagga tttcgccgcc tacgctggct ccttcgatga cgccaccatc 300
gaggaaatcc gcaagagggg agacgttgcc catgttgagg aggaccaaat ctggtatctt 360
gacgccttga ccactcaaaa gggcgcccca tggggcctgg gcagcatttc ccacagagga 420
caagcaagca ccgactacat ctacgacacc agcgctggcg caggcaccta tgcctacgtt 480
gtcgacagtg gcatcaatgt caaccacgtc gagttcgagg gtcgcgcatc gctggcatac 540
aacgccgctg gtggcagcca tgttgacagc atcggccacg gaacgcacgt tgctggaacc 600
attggcggca agacctacgg agtggccaag aaggctaacc ttctgtccgt caaggtcttc 660
cagggcgagt cctctagcac ctccatcatc cttgacggct tcaactgggc tgtcaatgac 720
attgtgagca agggtcgtac taagaaggct gcgatcaaca tgagccttgg tggtggttac 780
tcttatgcct tcaacaacgc tgttgagaac gctttcgatg aaggtgtcct ttctgtcgtc 840
gctgctggaa acgagaacag tgatgcctca aataccagcc ctgcttccgc tcctaacgct 900
ttgacggttg ctgcgatcaa caagagcaac gcccgcgcct ccttctccaa ctatggttcc 960
gttgtcgaca tcttcgctcc cggtcaggat atcctttcgg cctggattgg ctccaccact 1020
gccaccaaca ccatctccgg tacttccatg gccacccctc acgtcgttgg cctatccgtg 1080
tacttgatgg gtcttgagaa cctctctggc cctgctgcag tgaccgctcg catcaaggag 1140
ctggccacca atggtgttgt taccaacgtt aagggcagcc ccaacttgct tgcctacaat 1200
ggcaatgct 1209

<210> SEQ ID NO 158
<211> LENGTH: 1209
<212> TYPE: DNA
<213> ORGANISM: Artificial Sequence
<220> FEATURE:
<223> OTHER INFORMATION: Alkaline Protease (CL00037275 Ao.AP) (G1P)

<400> SEQUENCE: 158
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacaagggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt ttccggcacc 600
attgctggca agacttatgg tatcgccaag aaggccagca tcctttcggt caaagttttc 660
cagggtgaat cgagcagcac ttccgtcatt cttgacggct tcaactgggc tgccaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 159
<211> LENGTH: 1209
<212> TYPE: DNA
<213> ORGANISM: Artificial Sequence
<220> FEATURE:
<223> OTHER INFORMATION: Synthetic Alkaline Protease (CL00052050)

<400> SEQUENCE: 159

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacaagggc    420

cagggtagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt tgctggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgaca tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                          1209
```

<210> SEQ ID NO 160
<211> LENGTH: 1209
<212> TYPE: DNA
<213> ORGANISM: Artificial Sequence
<220> FEATURE:
<223> OTHER INFORMATION: Synthetic Alkaline Protease (CL00052064)

<400> SEQUENCE: 160

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacagaggc    420

cagcagagca ccgactacat ctacgacact agtgccggcg agggcaccta tgcctacgtg    480

gtggatagcg gtgtcaatgt cgaccatgag gagttcgagg gccgcgccag caaggcctac    540
```

```
aacgctgccg gtggtcagca tgtggacagc attggccatg gcacccacgt ttccggcacc    600
attgctggca agacttatgg tgtcgccaag aaggccagca tcctttcggt caaagttttc    660
cagggtgaat cgagcagcac ttccgtcatt cttgacggct tcaactgggc tgccaacgac    720
attgttagca agaagcgtac cagcaaggct gcaatcaaca tgagcttggg cggtggctac    780
tctaaggctt tcaacgatgc ggtcgagaac gcattcgagc agggtgttct ctcggttgtc    840
gctgccggta acgagaactc tgatgccggc caaaccagcc ctgcctctgc ccctgatgcc    900
atcactgttg ccgctatcca gaagagcaac aaccgcgcca gtttctccaa ctttggcaag    960
gtcgttgacg tcttcgctcc cggtcaagat atcctttctg cctggattgg ctcttcctct   1020
gccaccaaca ccatctctgg aacctccatg gctactcccc acattgtcgg cctgtccctc   1080
tacctcgctg cccttgagaa cctcgatggc cccgctgccg tgaccaagcg catcaaggag   1140
ttggccacca aggacgtcgt caaggatgtt aagggcagcc ctaacctgct tgcctacaac   1200
ggtaacgct                                                           1209
```

```
<210> SEQ ID NO 161
<211> LENGTH: 1209
<212> TYPE: DNA
<213> ORGANISM: Artificial Sequence
<220> FEATURE:
<223> OTHER INFORMATION: Synthetic Alkaline Protease (CL00052070)

<400> SEQUENCE: 161

atgcagtcca tcaagcgtac cttgctcctc ctcggagcta tcctttcccgc ggtcctcggt     60
gcccctgtgc aggaaacccg ccgggccgct gagaagcttc ctggaaagta cattgtcaca    120
ttcaagcccg gcattgacga ggcaaagatt caggagcata ccacctgggc taccaacatt    180
caccagcgca gtctggagcg tcgtggcgcc actggcggtg atcttcctgt cggtattgag    240
cgcaactaca agatcaacaa gttcgccgcc tatgcaggct ctttcgacga tgctaccatt    300
gaggagattc gcaagaacga agatgttgcc tacgtcgagg aggaccagat ctactacctc    360
gatggcctga ctacccagaa gagtgccccc tggggtctgg gcagcatttc ccacaagggc    420
cagcagagca ccgactacat ctacgacact agtgccggcg agggcaccta tgcctacgtg    480
gtggatagcg gtgtcaatgt cgaccatgag gagttcgagg gccgcgccag caaggcctac    540
aacgctgccg gtggtcagca tgtggacagc attggccatg gcacccacgt ttccggcacc    600
attgctggca agacttatgg tgtcgccaag aaggccagca tcctttcggt caaagttttc    660
cagggtgaat cgagcagcac ttccgtcatt cttgacggct tcaactgggc tgccaacgac    720
attgttagca agaagcgtac cagcaaggct gcaatcaaca tgagcttggg cggtggctac    780
tctaaggctt tcaacgatgc ggtcgagaac gcattcgagc agggtgttct ctcggttgtc    840
gctgccggta acgagaactc tgatgccggc caaaccagcc ctgcctctgc ccctgatgcc    900
atcactgttg ccgctatcca gaagagcaac aaccgcgcca gtttctccaa ctacggcaag    960
gtcgttgaca tcttcgctcc cggtcaagat atcctttctg cctggattgg ctcttcctct   1020
gccaccaaca ccatctctgg aacctccatg gctactcccc acgtcgtcgg cctgtccctc   1080
tacctcgctg cccttgagaa cctcgatggc cccgctgccg tgaccaagcg catcaaggag   1140
ttggccacca aggacgtcgt caaggatgtt aagggcagcc ctaacctgct tgcctacaac   1200
ggtaacgct                                                           1209

<210> SEQ ID NO 162
```

<211> LENGTH: 1209
<212> TYPE: DNA
<213> ORGANISM: Artificial Sequence
<220> FEATURE:
<223> OTHER INFORMATION: Synthetic Alkaline Protease (CL00052082)

<400> SEQUENCE: 162

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacaagggc    420

cagcagagca ccgactacat ctacgacact agtgccggcg agggcaccta tgcctacgtg    480

gtggatagcg gtgtcaatgt cgaccatgag gagttcgagg gccgcgccag caagggttac    540

aacgctgccg gtggtcagca tgtggacagc attggccatg gcacccacgt ttccggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgacg tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

<210> SEQ ID NO 163
<211> LENGTH: 1209
<212> TYPE: DNA
<213> ORGANISM: Artificial Sequence
<220> FEATURE:
<223> OTHER INFORMATION: Synthetic Alkaline Protease (CL00052174)

<400> SEQUENCE: 163

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacagaggc    420

cagggtagca ccgactacat ctacgacact agtgccggcg agggcaccta tgcctacgtg    480

gtggatagcg gtgtcaatgt cgaccatgag gagttcgagg gccgcgccag caagggttac    540

aacgctgccg gtggtcagca tgtggacagc attggccatg gcacccacgt ttccggcacc    600
```

attgctggca agacttatgg tgtcgccaag aaggccagca tcctttcggt caaagttttc 660
cagggtgaat cgagcagcac ttccgtcatt cttgacggct tcaactgggc tgccaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctacggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 164
<211> LENGTH: 1209
<212> TYPE: DNA
<213> ORGANISM: Artificial Sequence
<220> FEATURE:
<223> OTHER INFORMATION: Synthetic Alkaline Protease (CL00052220)

<400> SEQUENCE: 164
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacaagggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt tgctggcacc 600
attgctggca agacttatgg tatcgccaag aaggccagca tcctttcggt caaagttttc 660
cagggtgaat cgagcagcac ttccgtcatt cttgacggct tcaactgggc tgtcaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acgtcgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 165
<211> LENGTH: 1209
<212> TYPE: DNA

<213> ORGANISM: Artificial Sequence
<220> FEATURE:
<223> OTHER INFORMATION: Synthetic Alkaline Protease (CL00052236)

<400> SEQUENCE: 165

```
atgcagtcca tcaagcgtac cttgctcctc ctcggagcta tccttcccgc ggtcctcggt     60
gcccctgtgc aggaaacccg ccgggccgct gagaagcttc ctggaaagta cattgtcaca    120
ttcaagcccg gcattgacga ggcaaagatt caggagcata ccacctgggc taccaacatt    180
caccagcgca gtctggagcg tcgtggcgcc actggcggtg atcttcctgt cggtattgag    240
cgcaactaca agatcaacaa gttcgccgcc tatgcaggct ctttcgacga tgctaccatt    300
gaggagattc gcaagaacga agatgttgcc tacgtcgagg aggaccagat ctactacctc    360
gatggcctga ctacccagaa gagtgccccc tggggtctgg gcagcatttc ccacagaggc    420
cagcagagca ccgactacat ctacgacact agtgccggcg agggcaccta tgcctacgtg    480
gtggatagcg gtgtcaatgt cgaccatgag gagttcgagg gccgcgccag caaggcctac    540
aacgctgccg gtggtcagca tgtggacagc attggccatg gcacccacgt ttccggcacc    600
attgctggca agacttatgg tatcgccaag aaggccagca tcctttcggt caaagttttc    660
cagggtgaat cgagcagcac ttccgtcatt cttgacggct tcaactgggc tgtcaacgac    720
attgttagca agaagcgtac cagcaaggct gcaatcaaca tgagcttggg cggtggctac    780
tctaaggctt tcaacgatgc ggtcgagaac gcattcgagc agggtgttct ctcggttgtc    840
gctgccggta acgagaactc tgatgccggc caaaccagcc ctgcctctgc ccctgatgcc    900
atcactgttg ccgctatcca gaagagcaac aaccgcgcca gtttctccaa ctttggcaag    960
gtcgttgacg tcttcgctcc cggtcaagat atcctttctg cctggattgg ctcttcctct   1020
gccaccaaca ccatctctgg aacctccatg gctactcccc acattgtcgg cctgtccctc   1080
tacctcgctg cccttgagaa cctcgatggc cccgctgccg tgaccaagcg catcaaggag   1140
ttggccacca aggacgtcgt caaggatgtt aagggcagcc ctaacctgct tgcctacaac   1200
ggtaacgct                                                            1209
```

<210> SEQ ID NO 166
<211> LENGTH: 1209
<212> TYPE: DNA
<213> ORGANISM: Artificial Sequence
<220> FEATURE:
<223> OTHER INFORMATION: Synthetic Alkaline Protease (CL00052304)

<400> SEQUENCE: 166

```
atgcagtcca tcaagcgtac cttgctcctc ctcggagcta tccttcccgc ggtcctcggt     60
gcccctgtgc aggaaacccg ccgggccgct gagaagcttc ctggaaagta cattgtcaca    120
ttcaagcccg gcattgacga ggcaaagatt caggagcata ccacctgggc taccaacatt    180
caccagcgca gtctggagcg tcgtggcgcc actggcggtg atcttcctgt cggtattgag    240
cgcaactaca agatcaacaa gttcgccgcc tatgcaggct ctttcgacga tgctaccatt    300
gaggagattc gcaagaacga agatgttgcc tacgtcgagg aggaccagat ctactacctc    360
gatggcctga ctacccagaa gagtgccccc tggggtctgg gcagcatttc ccacaagggc    420
cagggtagca ccgactacat ctacgacact agtgccggcg agggcaccta tgcctacgtg    480
gtggatagcg gtgtcaatgt cgaccatgag gagttcgagg gccgcgccag caagggttac    540
aacgctgccg gtggtcagca tgtggacagc attggccatg gcacccacgt ttccggcacc    600
attgctggca agacttatgg tgtcgccaag aaggccagca tcctttcggt caaagttttc    660
```

```
cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgacg tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

<210> SEQ ID NO 167
<211> LENGTH: 1209
<212> TYPE: DNA
<213> ORGANISM: Artificial Sequence
<220> FEATURE:
<223> OTHER INFORMATION: Synthetic Alkaline Protease (CL00052312)

<400> SEQUENCE: 167

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacaagggc    420

cagcagagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt ttccggcacc    600

attgctggca agacttatgg tgtcgccaag aaggccagca tcctttcggt caaagttttc    660

cagggtgaat cgagcagcac ttccgtcatt cttgacggct tcaactgggc tgtcaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgacg tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

<210> SEQ ID NO 168
<211> LENGTH: 1209
<212> TYPE: DNA
<213> ORGANISM: Artificial Sequence
<220> FEATURE:

<223> OTHER INFORMATION: Synthetic Alkaline Protease (CL00052338)

<400> SEQUENCE: 168

```
atgcagtcca tcaagcgtac cttgctcctc ctcggagcta tccttcccgc ggtcctcggt      60
gcccctgtgc aggaaacccg ccgggccgct gagaagcttc ctggaaagta cattgtcaca     120
ttcaagcccg gcattgacga ggcaaagatt caggagcata ccacctgggc taccaacatt     180
caccagcgca gtctggagcg tcgtggcgcc actggcggtg atcttcctgt cggtattgag     240
cgcaactaca agatcaacaa gttcgccgcc tatgcaggct ctttcgacga tgctaccatt     300
gaggagattc gcaagaacga agatgttgcc tacgtcgagg aggaccagat ctactacctc     360
gatggcctga ctacccagaa gagtgccccc tggggtctgg gcagcatttc ccacaagggc     420
cagcagagca ccgactacat ctacgacact agtgccggcg agggcaccta tgcctacgtg     480
gtggatagcg gtgtcaatgt cgaccatgag gagttcgagg gccgcgccag caaggcctac     540
aacgctgccg gtggtcagca tgtggacagc attggccatg gcacccacgt ttccggcacc     600
attgctggca agacttatgg tgtcgccaag aaggccagca tcctttcggt caaagttttc     660
cagggtgaat cgagcagcac ttccgtcatt cttgacggct tcaactgggc tgccaacgac     720
attgttagca agaagcgtac cagcaaggct gcaatcaaca tgagcttggg cggtggctac     780
tctaaggctt tcaacgatgc ggtcgagaac gcattcgagc agggtgttct ctcggttgtc     840
gctgccggta acgagaactc tgatgccggc caaaccagcc ctgcctctgc ccctgatgcc     900
atcactgttg ccgctatcca gaagagcaac aaccgcgcca gtttctccaa ctacggcaag     960
gtcgttgacg tcttcgctcc cggtcaagat atcctttctg cctggattgg ctcttcctct    1020
gccaccaaca ccatctctgg aacctccatg gctactcccc acattgtcgg cctgtccctc    1080
tacctcgctg cccttgagaa cctcgatggc cccgctgccg tgaccaagcg catcaaggag    1140
ttggccacca aggacgtcgt caaggatgtt aagggcagcc ctaacctgct tgcctacaac    1200
ggtaacgct                                                            1209
```

<210> SEQ ID NO 169
<211> LENGTH: 1209
<212> TYPE: DNA
<213> ORGANISM: Artificial Sequence
<220> FEATURE:
<223> OTHER INFORMATION: Synthetic Alkaline Protease (CL00052357)

<400> SEQUENCE: 169

```
atgcagtcca tcaagcgtac cttgctcctc ctcggagcta tccttcccgc ggtcctcggt      60
gcccctgtgc aggaaacccg ccgggccgct gagaagcttc ctggaaagta cattgtcaca     120
ttcaagcccg gcattgacga ggcaaagatt caggagcata ccacctgggc taccaacatt     180
caccagcgca gtctggagcg tcgtggcgcc actggcggtg atcttcctgt cggtattgag     240
cgcaactaca agatcaacaa gttcgccgcc tatgcaggct ctttcgacga tgctaccatt     300
gaggagattc gcaagaacga agatgttgcc tacgtcgagg aggaccagat ctactacctc     360
gatggcctga ctacccagaa gagtgccccc tggggtctgg gcagcatttc ccacagaggc     420
cagggtagca ccgactacat ctacgacact agtgccggcg agggcaccta tgcctacgtg     480
gtggatagcg gtgtcaatgt cgaccatgag gagttcgagg gccgcgccag caaggcctac     540
aacgctgccg gtggtcagca tgtggacagc attggccatg gcacccacgt ttccggcacc     600
attgctggca agacttatgg tgtcgccaag aaggccagca tcctttcggt caaagttttc     660
cagggtgaat cgagcagcac ttccgtcatt cttgacggct tcaactgggc tgccaacgac     720
```

attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 170
<211> LENGTH: 1209
<212> TYPE: DNA
<213> ORGANISM: Artificial Sequence
<220> FEATURE:
<223> OTHER INFORMATION: Synthetic Alkaline Protease (CL00052358)

<400> SEQUENCE: 170
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacaagggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt ttccggcacc 600
attgctggca agacttatgg tgtcgccaag aaggccagca tcctttcggt caaagttttc 660
cagggtgaat cgagcagcac ttccgtcatt cttgacggct tcaactgggc tgccaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 171
<211> LENGTH: 1209
<212> TYPE: DNA
<213> ORGANISM: Artificial Sequence
<220> FEATURE:
<223> OTHER INFORMATION: Synthetic Alkaline Protease (CL00052373)

<400> SEQUENCE: 171
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacagaggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt ttccggcacc 600
attgctggca agacttatgg tatcgccaag aaggccagca tcctttcggt caaagttttc 660
cagggtgaat cgagcagcac ttccgtcatt cttgacggct tcaactgggc tgccaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acgtcgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 172
<211> LENGTH: 1209
<212> TYPE: DNA
<213> ORGANISM: Artificial Sequence
<220> FEATURE:
<223> OTHER INFORMATION: Synthetic Alkaline Protease (CL00052383)

<400> SEQUENCE: 172
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacaagggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt tgctggcacc 600
attgctggca agacttatgg tgtcgccaag aaggccagca tcctttcggt caaagttttc 660
cagggtgaat cgagcagcac ttccgtcatt cttgacggct tcaactgggc tgtcaacgac 720
attgttagca agaagcgtac cagcaaggct gcaatcaaca tgagcttggg cggtggctac 780

```
tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgacg tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

```
<210> SEQ ID NO 173
<211> LENGTH: 1209
<212> TYPE: DNA
<213> ORGANISM: Artificial Sequence
<220> FEATURE:
<223> OTHER INFORMATION: Synthetic Alkaline Protease (CL00052388)

<400> SEQUENCE: 173

atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacagaggc    420

cagggtagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt ttccggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgaca tcttcgctcc cggtcaagat atcctttctg cctggattgg ctcttcctct   1020

gccaccaaca ccatctctgg aacctccatg gctactcccc acgtcgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

```
<210> SEQ ID NO 174
<211> LENGTH: 1209
<212> TYPE: DNA
<213> ORGANISM: Artificial Sequence
<220> FEATURE:
<223> OTHER INFORMATION: Synthetic Alkaline Protease (CL00052412)

<400> SEQUENCE: 174
```

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacagaggc    420

cagcagagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt tgctggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg gtgctatcca gaagagcaac aaccgcgcca gtttctccaa ctttggcaag    960

gtcgttgacg tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

<210> SEQ ID NO 175
<211> LENGTH: 1209
<212> TYPE: DNA
<213> ORGANISM: Artificial Sequence
<220> FEATURE:
<223> OTHER INFORMATION: Synthetic Alkaline Protease (CL00052418)

<400> SEQUENCE: 175

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacaagggc    420

cagcagagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt tgctggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840
```

gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 176
<211> LENGTH: 1209
<212> TYPE: DNA
<213> ORGANISM: Artificial Sequence
<220> FEATURE:
<223> OTHER INFORMATION: Synthetic Alkaline Protease (CL00052440)

<400> SEQUENCE: 176
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacagaggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt ttccggcacc 600
attgctggca agacttatgg tatcgccaag aaggccagca tcctttcggt caaagttttc 660
cagggtgaat cgagcagcac ttccgtcatt cttgacggct tcaactgggc tgccaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctttggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 177
<211> LENGTH: 1209
<212> TYPE: DNA
<213> ORGANISM: Artificial Sequence
<220> FEATURE:
<223> OTHER INFORMATION: Synthetic Alkaline Protease (CL00052441)

<400> SEQUENCE: 177
atgcagtcca tcaagcgtac cttgctcctc ctcggagcta tccttcccgc ggtcctcggt 60

```
gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacaagggc    420

cagggtagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt ttccggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgaca tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                         1209
```

<210> SEQ ID NO 178
<211> LENGTH: 1209
<212> TYPE: DNA
<213> ORGANISM: Artificial Sequence
<220> FEATURE:
<223> OTHER INFORMATION: Synthetic Alkaline Protease (CL00052473)

<400> SEQUENCE: 178

```
atgcagtcca tcaagcgtac cttgctcctc ctcggagcta tccttcccgc ggtcctcggt     60

gcccctgtgc aggaaacccg ccgggccgct gagaagcttc ctggaaagta cattgtcaca    120

ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacagaggc    420

cagcagagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt ttccggcacc    600

attgctggca agacttatgg tatcgccaag aaggccagca tcctttcggt caaagttttc    660

cagggtgaat cgagcagcac ttccgtcatt cttgacggct tcaactgggc tgccaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900
```

atcactgttg ccgctatcca gaagagcaac aaccgcgcca gtttctccaa ctacggcaag 960
gtcgttgacg tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 179
<211> LENGTH: 1209
<212> TYPE: DNA
<213> ORGANISM: Artificial Sequence
<220> FEATURE:
<223> OTHER INFORMATION: Synthetic Alkaline Protease (CL00052515)

<400> SEQUENCE: 179
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120
ttcaagcccg gcattgacga ggcaaagatt caggagcata ccacctgggc taccaacatt 180
caccagcgca gtctggagcg tcgtggcgcc actggcggtg atcttcctgt cggtattgag 240
cgcaactaca agatcaacaa gttcgccgcc tatgcaggct ctttcgacga tgctaccatt 300
gaggagattc gcaagaacga agatgttgcc tacgtcgagg aggaccagat ctactacctc 360
gatggcctga ctacccagaa gagtgccccc tggggtctgg gcagcatttc ccacagaggc 420
cagcagagca ccgactacat ctacgacact agtgccggcg agggcaccta tgcctacgtg 480
gtggatagcg gtgtcaatgt cgaccatgag gagttcgagg gccgcgccag caaggcctac 540
aacgctgccg gtggtcagca tgtggacagc attggccatg gcacccacgt ttccggcacc 600
attgctggca agacttatgg tgtcgccaag aaggccagca tcctttcggt caaagttttc 660
cagggtgaat cgagcagcac ttccgtcatt cttgacggct tcaactgggc tgccaacgac 720
attgttagca agaagcgtac cagcaaggct gcaatcaaca tgagcttggg cggtggctac 780
tctaaggctt tcaacgatgc ggtcgagaac gcattcgagc agggtgttct ctcggttgtc 840
gctgccggta acgagaactc tgatgccggc caaaccagcc ctgcctctgc ccctgatgcc 900
atcactgttg ccgctatcca gaagagcaac aaccgcgcca gtttctccaa ctacggcaag 960
gtcgttgaca tcttcgctcc cggtcaagat atcctttctg cctggattgg ctcttcctct 1020
gccaccaaca ccatctctgg aacctccatg gctactcccc acattgtcgg cctgtccctc 1080
tacctcgctg cccttgagaa cctcgatggc cccgctgccg tgaccaagcg catcaaggag 1140
ttggccacca aggacgtcgt caaggatgtt aagggcagcc ctaacctgct tgcctacaac 1200
ggtaacgct 1209

<210> SEQ ID NO 180
<211> LENGTH: 1209
<212> TYPE: DNA
<213> ORGANISM: Artificial Sequence
<220> FEATURE:
<223> OTHER INFORMATION: Synthetic Alkaline Protease (CL00052530)

<400> SEQUENCE: 180
atgcagtcca tcaagcgtac cttgctcctc ctcggagcta tccttcccgc ggtcctcggt 60
gcccctgtgc aggaaacccg ccgggccgct gagaagcttc ctggaaagta cattgtcaca 120

-continued

```
ttcaagcccg gcattgacga ggcaaagatt caggagcata ccacctgggc taccaacatt    180

caccagcgca gtctggagcg tcgtggcgcc actggcggtg atcttcctgt cggtattgag    240

cgcaactaca agatcaacaa gttcgccgcc tatgcaggct ctttcgacga tgctaccatt    300

gaggagattc gcaagaacga agatgttgcc tacgtcgagg aggaccagat ctactacctc    360

gatggcctga ctacccagaa gagtgccccc tggggtctgg gcagcatttc ccacaagggc    420

cagcagagca ccgactacat ctacgacact agtgccggcg agggcaccta tgcctacgtg    480

gtggatagcg gtgtcaatgt cgaccatgag gagttcgagg gccgcgccag caaggcctac    540

aacgctgccg gtggtcagca tgtggacagc attggccatg gcacccacgt ttccggcacc    600

attgctggca agacttatgg tatcgccaag aaggccagca tcctttcggt caaagttttc    660

cagggtgaat cgagcagcac ttccgtcatt cttgacggct tcaactgggc tgtcaacgac    720

attgttagca agaagcgtac cagcaaggct gcaatcaaca tgagcttggg cggtggctac    780

tctaaggctt tcaacgatgc ggtcgagaac gcattcgagc agggtgttct ctcggttgtc    840

gctgccggta acgagaactc tgatgccggc caaaccagcc ctgcctctgc ccctgatgcc    900

atcactgttg ccgctatcca gaagagcaac aaccgcgcca gtttctccaa ctttggcaag    960

gtcgttgacg tcttcgctcc cggtcaagat atcctttctg cctggattgg ctcttcctct   1020

gccaccaaca ccatctctgg aacctccatg gctactcccc acattgtcgg cctgtccctc   1080

tacctcgctg cccttgagaa cctcgatggc cccgctgccg tgaccaagcg catcaaggag   1140

ttggccacca aggacgtcgt caaggatgtt aagggcagcc ctaacctgct tgcctacaac   1200

ggtaacgct                                                           1209
```

VARIANT ALKALINE PROTEASE ENZYME COMPOSITIONS AND METHODS

I. CROSS REFERNCE TO RELATED APPLICATIONS

This application claims priority to U.S. Provisional Patent Application No. 62/667,038, filed on May 4, 2018, which is expressly incorporated by reference in its entirety.

II. SEQUENCE LISTING

The instant application contains a Sequence Listing which has been submitted electronically in ASCII format and is hereby incorporated by reference in its entirety. Said ASCII copy, created on May 2, 2019, is named 114095-5006-US_ST25.txt and is 416 kilobytes in size.

III. FIELD OF THE INVENTION

This invention relates to variant alkaline proteases, polynucleotides encoding the variant alkaline proteases, methods of making the variant alkaline proteases, and methods of using the variant alkaline proteases. Also described are the use of alkaline proteases of the invention in various industries, such as leather processing, food processing, chemical industry, medicinal uses, detergent industry (e.g laundry, dishwasher and contact lens detergents), etc. The invention also relates to compositions comprising one or more variant alkaline proteases of the invention.

IV. BACKGROUND OF THE INVENTION

Alkaline protease is an enzyme capable of hydrolyzing a broad range of peptide bonds found in both native proteins and synthetic substrates, and are active in a neutral to alkaline pH range. These enzymes can be used in detergent, food, chemical, pharmaceutical, leather industries, etc. (Anissa Haddar, Rym Agrebi, et al. 2009, Bioresource Technology. 100(13):3366-3373; P Ellaiah, B Srinivasulu et al. 2002, Journal of Scientific & Industrial Research. 61:690-704). Alkaline proteases for industrial use can be obtained from different sources such as bacteria, fungi, yeast or certain insects (Adil Anwar, Mohammed Saleemuddin, 1998, Bioresource Technology. 64:175-183).

One important application of industrial enzymes is in the detergent industry, and alkaline proteases can be incorporated into detergents, for example, laundry, dishwasher and/or contact lens solutions for cleaning purpose. For an enzyme to be used as a detergent additive, it should be stable at pH 8-12 and a broad temperature range (e.g. 20-40° C. for low-temperature washing and 60-65° C. for high temperature washing), withstand oxidizing and chelating agents, be compatible with other ingredients in the detergents. Moreover, it should be stable for storage at room temperature and have broad substrate specificity.

Therefore, there remains a need in the art for variant alkaline proteases with increased activity, thermoactivity, thermostability, pH stability as well as optimal performance in different ionic strengths (e.g. both soft and hard water), the ability to withstand oxidizing and chelating agents and long shelf life at room temperature. The present invention meets this need and provides variant alkaline proteases with improved characteristics compared to a parent alkaline protease. Such improved alkaline proteases can also be used in other industries, such as leather processing, food processing, chemical industry, medicinal uses etc.

It is an object of the present invention to provide variant alkaline protease enzymes having alkaline protease activity with improved properties as compared to the parent alkaline protease(s) and polynucleotides encoding the variant alkaline protease enzymes as well as methods of making and using such variant alkaline protease enzymes in various processes.

V. BRIEF SUMMARY OF THE INVENTION

Accordingly, the present invention provides variant alkaline protease and methods of making and using them. In some embodiments, the invention provides compositions comprising a variant alkaline protease enzyme comprising at least one amino acid substitution as compared to SEQ ID NO:1, wherein the variant enzyme has alkaline protease activity, wherein the amino acid substitution is at a position number selected from the group consisting of 18, 21, 24, 53, 58, 91, 130, 234, 246 and 275, and wherein said variant alkaline protease enzyme exhibits at least 96% identity to SEQ ID NO:1.

In one aspect, the invention provides compositions comprising a variant alkaline protease enzyme comprising at least one amino acid substitution as compared to SEQ ID NO:1, wherein said variant alkaline protease enzyme has alkaline protease activity, wherein said amino acid substitution is selected from the group consisting of: K18R, A21G, D24H, S53G, A58G, T91A, A130V, I234V, N246G and K275L, and wherein said variant alkaline protease enzyme exhibits at least 96% identity to SEQ ID NO:1.

In an additional aspect, the invention provides compositions comprising a variant alkaline protease enzyme comprising at least one amino acid substitution as compared to SEQ ID NO:1, wherein said amino acid substitution is selected from the group consisting of: K18R, A21G, D24H, S53G, A58G, T91A, A130V, I234V, N246G and K275L, wherein said variant alkaline protease enzyme exhibits at least 96% identity to SEQ ID NO:1, and wherein said variant enzyme has at least 1.1 fold better alkaline protease activity as compared to SEQ ID NO:1 under a condition selected from the group consisting of thermostability at 37° C., thermostability at 40° C., thermostability at 45° C., thermostability at 50° C., thermostability at 52° C. and thermostability at 55° C.

In an additional aspect, the invention provides compositions comprising a variant alkaline protease enzyme comprising at least one amino acid substitution as compared to SEQ ID NO:1, wherein said amino acid substitution is selected from the group consisting of: K18R, A21G, D24H, S53G, A58G, T91A, A130V, I234V, N246G and K275L, wherein said variant alkaline protease enzyme exhibits at least 96% identity to SEQ ID NO:1, and wherein said variant enzyme has at least 1.1 fold better alkaline protease activity as compared to SEQ ID NO:1 under a condition selected from the group consisting of pH at 9, pH at 10, pH at 10.5, pH at 11 and pH at 11.3.

In an additional aspect, the invention provides compositions comprising a variant alkaline protease enzyme comprising at least one amino acid substitution as compared to SEQ ID NO:1 as described herein, wherein said variant alkaline protease enzymes exhibit at least at least 97%, 98%, or 99% identity to SEQ ID NO:1.

In a further aspect, the invention provides compositions comprising a variant alkaline protease enzyme comprising at least one amino acid substitution as compared to SEQ ID NO:1 as described herein, wherein said variant alkaline protease enzyme has one of said amino acid substitution, two of said amino acid substitutions, three of said amino acid substitutions, four of said amino acid substitutions, five of said amino acid substitutions, six of said amino acid substitutions, seven of said amino acid substitutions, eight of said amino acid substitutions, nine of said amino acid substitutions, or ten of said amino acid substitutions.

In an additional aspect, the invention provides compositions comprising a variant alkaline protease enzyme comprising at least one amino acid substitution as compared to SEQ ID NO:1 as described herein, wherein the amino acid substitution is selected from the group consisting of: K18R/A58G/N246G, K18R/I234V, K18R/A21G/S53G/A58G/K275L, K18R/S53G/A130V/I234V, K18R/A58G, K18R/T91A/I234V/N246G/K275L, K18R/A21G/A58G/I234V, K18R/S53G, K18R/A21G, K18R, K18R/A21G/I234V/N246G, K18R/S53G/A58G/I234V, K18R/S53G/T91A, K18R/A58G/I234V/K275L, K18R/I234V/K275L, A21G/S53G/K275L, K18R/A58G/K275L, K18R/A21G/A58G, K18R/D24H/S53G/A58G/A130V, K18R/S53G/A130V/K275L and K18R/S53G/T91A/I234V/K275L.

In a further aspect, the invention provides compositions comprising a variant alkaline protease enzyme comprising at least one amino acid substitution as compared to SEQ ID NO:1 as described herein, wherein the amino acid substitution is selected from the group consisting of: K18R/A58G/N246G, K18R/I234V, K18R/S53G/A130V/I234V and K18R/A58G.

In an additional aspect, the invention provides compositions comprising a variant alkaline protease enzyme comprising at least one amino acid substitution as compared to SEQ ID NO:1 as described herein, wherein said variant alkaline protease enzyme comprises amino acid substitutions K18R/I234V and exhibits at least 90% identity to SEQ ID NO:3.

In an additional aspect, the invention provides compositions comprising a variant alkaline protease enzyme having an amino acid sequence of SEQ ID NO:3.

In a further aspect, the invention provides compositions comprising a variant alkaline protease enzyme comprising at least one amino acid substitution as compared to SEQ ID NO:1 as described herein, wherein the composition is a detergent composition comprising said variant alkaline protease enzyme.

In some embodiments, the invention provides compositions comprising a variant alkaline protease enzyme comprising at least one amino acid substitution as compared to SEQ ID NO:2, wherein the variant enzyme has alkaline protease activity, wherein the amino acid substitution is at a position number selected from the group consisting of 18, 21, 58, 77, 87, 117, 183, 197, 203 and 234, and wherein said variant alkaline protease enzyme exhibits at least 98% identity to SEQ ID NO:2.

In one aspect, the invention provides compositions comprising a variant alkaline protease enzyme comprising at least one amino acid substitution as compared to SEQ ID NO:2, wherein the variant enzyme has alkaline protease activity, wherein the amino acid substitution is selected from the group consisting of: K18R, Q21G, A58G, S77A, I87V, A117V, A183G, F197Y, V203I, and I234V, and wherein said variant alkaline protease enzyme exhibits at least 98% identity to SEQ ID NO:2.

In an additional aspect, the invention provides compositions comprising a variant alkaline protease enzyme comprising at least one amino acid substitution as compared to SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzyme exhibits at least 98% identity to SEQ ID NO:2, and wherein said variant enzyme has at least 1.1 fold better alkaline protease activity as compared to SEQ ID NO:2 under a condition of thermostability at 37° C. or thermostability at 40° C.

In a further aspect, the invention provides compositions comprising a variant alkaline protease enzyme comprising at least one amino acid substitution as compared to SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzyme exhibits at least 98% identity to SEQ ID NO:2, and wherein said variant enzyme has at least 1.1 fold better alkaline protease activity as compared to SEQ ID NO:2 under a condition selected from the group consisting of pH at 10.5, pH at 11 or pH at 11.3.

In an additional aspect, the invention provides compositions comprising a variant alkaline protease enzyme comprising at least one amino acid substitution as compared to SEQ ID NO:2 as described herein, wherein said variant alkaline protease enzymes exhibit at least 99% identity to SEQ ID NO:2.

In a further aspect, the invention provides compositions comprising a variant alkaline protease enzyme comprising at least one amino acid substitution as compared to SEQ ID NO:2 as described herein, wherein said variant alkaline protease enzyme has one of said amino acid substitution, two of said amino acid substitutions, three of said amino acid substitutions, four of said amino acid substitutions, or five of said amino acid substitutions.

In a further aspect, the invention provides compositions comprising a variant alkaline protease enzyme comprising at least one amino acid substitution as compared to SEQ ID NO:2 as described herein, wherein said amino acid substitution(s) are selected from the group consisting of: Q21G/S77A/V203I, K18R/I87V, I87V/F197Y/V203I/I234V, A58G, K18R/Q21G/A58G/I87V/F197Y, S77A/A117V/I234V, K18R/A117V, Q21G/A58G/I87V, I87V/A117V, I87V/F197Y, K18R/Q21G/I87V, I87V, K18R/I234V, S77A/I87V/A117V, K18R/Q21G/V203I/I234V, K18R/S77A/A183G, S77A, K18R, Q21G/V203I, K18R/F197Y, K18R/I87V/F197Y/V203I and A117V.

In an additional aspect, the invention provides compositions comprising a variant alkaline protease enzyme comprising at least one amino acid substitution as compared to SEQ ID NO:2 as described herein, wherein said amino acid substitutions are K18R/Q21G/A58G/I87V/F197Y or K18R/S77A/A183G.

In a further aspect, the invention provides compositions comprising a variant alkaline protease enzyme comprising at least one amino acid substitution as compared to SEQ ID NO:2 as described herein, wherein said variant alkaline protease enzyme comprises amino acid substitutions K18R/Q21G/A58G/I87V/F197Y and exhibits at least 90% identity to SEQ ID NO:4.

In an additional aspect, the invention provides compositions comprising a variant alkaline protease enzyme comprising at least one amino acid substitution as compared to SEQ ID NO:2 as described herein, wherein said variant alkaline protease enzyme has an amino acid sequence of SEQ ID NO:4.

In a further aspect, the invention provides compositions comprising a variant alkaline protease enzyme comprising at least one amino acid substitution as compared to SEQ ID NO:2 as described herein, wherein the composition is a detergent composition comprising said variant alkaline protease enzyme.

In an additional aspect, the invention provides methods of making variant alkaline protease enzymes, comprising substituting one or more amino acids of a parent alkaline protease enzyme of SEQ ID NO:1, wherein said amino acid substitution is selected from the group consisting of: K18R, A21G, D24H, S53G, A58G, T91A, A130V, I234V, N246G and K275L, wherein said variant alkaline protease enzymes have alkaline protease activity, and wherein said variant alkaline protease enzymes exhibit at least 96% identity to SEQ ID NO:1.

In a further aspect, the invention provides methods of making variant alkaline protease enzymes, comprising substituting one or more amino acids of a parent alkaline protease enzyme of SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzymes have alkaline protease activity, and wherein said variant alkaline protease enzymes exhibit at least 98% identity to SEQ ID NO:2.

In a further aspect, the invention provides nucleic acids encoding said variant alkaline protease enzymes as described herein.

In an additional aspect, the invention provides nucleic acids encoding said variant alkaline protease enzymes as described herein, wherein the nucleic acid is codon optimized for a host organism for expression of the variant alkaline protease enzyme in said organism.

In a further aspect, the invention provides expression vectors comprising said nucleic acids as described herein.

In a further aspect, the invention provides host cells comprising the nucleic acids as described herein.

In an additional aspect, the invention provides host cells comprising the expression vectors as described herein.

In a further aspect, the invention provides host cells as described herein, wherein said host cell is selected from the group consisting of a bacterial cell, a fungal cell, or a yeast cell.

In an additional aspect, the invention provides methods of making variant alkaline protease enzymes comprising: a) culturing a host cell comprising a nucleic acid expressing said variant alkaline protease enzyme as described herein under conditions wherein the variant alkaline protease enzyme is expressed; and b) purifying the variant alkaline protease enzyme.

In further aspects, the invention provides methods of cleaning surface(s) of laundry, dishes and/or contact lens comprising contacting the surface(s) with variant alkaline protease enzyme(s) as described herein.

In further aspects, the invention provides methods of cleaning surface(s) of laundry, dishes and/or contact lens comprising contacting the surface(s) with a detergent composition as described herein.

In further aspects, the invention provides methods of using the variant alkaline protease enzymes as described herein in leather processing, food processing, chemical industry and/or medicinal uses.

VI. BRIEF DESCRIPTION OF THE DRAWINGS

FIG. 1A provides data regarding pH challenge of alkaline protease Nf.AP (SEQ ID NO:1). FIG. 1B provides data regarding pH challenge of alkaline protease Ao.AP (SEQ ID NO:2). The pH challenge was performed at 37° C. for 4 hours as discussed in Example 5.

FIG. 2A provides data regarding thermal challenge of alkaline protease Nf.AP (SEQ ID NO:1). FIG. 2B provides data regarding thermal challenge of alkaline protease Ao.AP (SEQ ID NO:2). The thermal challenge was performed at pH 10.5 for 3 hours, as discussed in Example 5.

FIG. 3 provides a schematic of the domains of alkaline proteases: Nf.AP, which corresponds to SEO ID NO:46 and Ao.AP, which corresponds to SEO ID NO:68. The Pre region (signal peptide), containing the first 21 amino acids, is bolded and underlined. The Pro region, containing the following 100 amino acids, is bolded and italic. The Pro region is followed by the Mature region, which is neither bolded nor underlined. Full length sequence alignment demonstrates that Nf.AP and Ao.AP are 82% identical at the full length (Pre-Pro-Mature) and 84% identical at the mature region.

FIG. 4 provides data regarding the high pH tolerance improvement and thermostability improvement of variant alkaline proteases as compared to Nf.AP (SEQ ID NO:1; Colony Tracking Number: CL00037296). Sequence numbering starts from the mature region.

FIG. 5 provides data regarding the activity improvement and thermostability improvement of variant alkaline proteases as compared to Ao.AP (SEQ ID NO:2; Colony Tracking Number: CL00037275). Result of 0.00 represents no activity detected. Sequence numbering starts from the mature region.

FIG. 6 depict a variant table showing beneficial mutations of Nf.AP and Ao.AP at various positions. Sequence numbering starts from the mature region. As described herein, these may be combined in any combination, and with variant sets as outlined herein.

FIG. 7 shows closest homologs to Nf.AP.

FIG. 8 shows closest homologs to Ao.AP.

Figure 1A:
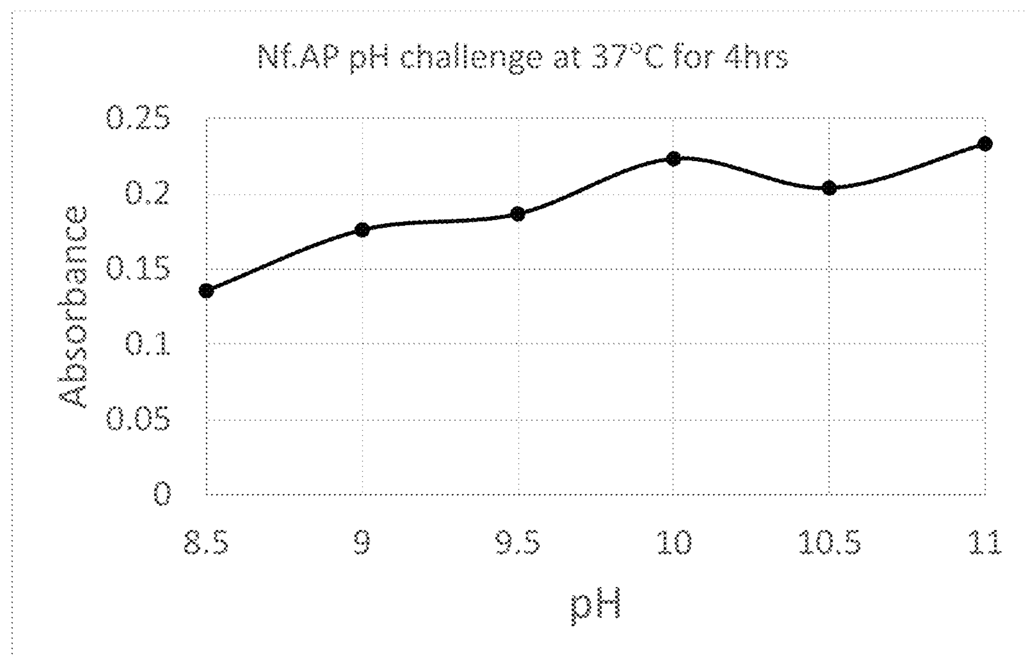

FIGS. 9A-9D show the amino acid sequences of the mature region of CL00037296 Nf.AP (G1P, SEQ ID NO:1) and variant alkaline proteases. FIG. 9A shows the amino acid sequences of the mature region of CL00037296 Nf.AP (G1P) and variant alkaline proteases: CL00052543, CL00052570 (SEQ ID NO:3), CL00052579, CL00052582, and CL00052631. FIG. 9B shows the amino acid sequences of the mature region of Nf.AP variant alkaline proteases: CL00052644, CL00052649, CL00052662, CL00052663, CL00052690, and CL00052706. FIG. 9C shows the amino acid sequences of the mature region of Nf.AP variant alkaline proteases: CL00052720, L00052745, CL00052757, CL00052795, CL00052806, and CL00052809. FIG. 9D shows the amino acid sequences of the mature region of Nf.AP variant alkaline proteases: CL00052822, CL00052844, CL00052861, and CL00052875.

FIGS. 10A-10D show the amino acid sequences of the mature region of CL00037275 Ao.AP (G1P, SEQ ID NO:2) and variant alkaline proteases. FIG. 10A shows the amino acid sequences of the mature region of CL00037275 Ao.AP (G1P) and variant alkaline proteases: CL00052050, CL00052064, CL00052070, CL00052082, and CL00052174 (SEQ ID NO:4). FIG. 10B shows the amino acid sequences of the mature region of Ao.AP variant alkaline proteases: CL00052220, CL00052236, CL00052304, CL00052312, CL00052338 and CL00052357. FIG. 10C shows the amino acid sequences of the mature region of Ao.AP variant alkaline proteases: CL00052358, CL00052373, CL00052383, CL00052388, CL00052412 and CL00052418. FIG. 10D shows the amino acid sequences of the mature region of Ao.AP variant alkaline proteases: CL00052440, CL00052441, CL00052473, CL00052515, and CL00052530.

FIGS. 11A-11E show the amino acid sequences of the full length of CL00037296 Nf.AP (G1P) and variant alkaline proteases. FIG. 11A shows the amino acid sequences of the full length of CL00037296 Nf.AP (G1P) and variant alkaline proteases: CL00052543, CL00052570, CL00052579, and CL00052582. FIG. 11B shows the amino acid sequences of the full length of Nf.AP variant alkaline proteases: CL00052631, CL00052644, CL00052649, CL00052662, and CL00052663. FIG. 11C shows the amino acid sequences of the full length of Nf.AP variant alkaline proteases: CL00052690, CL00052706, CL00052720, CL00052745, and CL00052757. FIG. 11D shows the amino acid sequences of the full length of Nf.AP variant alkaline proteases: CL00052795, CL00052806, CL00052809, CL00052822, and CL00052844. FIG. 11E shows the amino acid sequences of the full length of Nf.AP variant alkaline proteases: CL00052861, and CL00052875.

FIGS. 12A-12E show the amino acid sequences of the full length of CL00037275 Ao.AP (G1P) and variant alkaline proteases. FIG. 12A shows the amino acid sequences of the full length of CL00037275 Ao.AP (G1P) and variant alkaline proteases: CL00052050, CL00052064, CL00052070, and CL00052082. FIG. 12B shows the amino acid sequences of the full length of Ao.AP variant alkaline proteases: CL00052174, CL00052220, CL00052236, CL00052304, and CL00052312. FIG. 12C shows the amino acid sequences of the full length of Ao.AP variant alkaline proteases: CL00052338, CL00052357, CL00052358, CL00052373, and CL00052383. FIG. 12D shows the amino add sequences of the full length of Ao.AP variant alkaline proteases: CL00052388, CL00052412, CL00052418, CL00052440, and CL00052441. FIG. 12E shows the amino acid sequences of the full length of Ao.AP variant alkaline proteases: CL00052473, CL00052515, and CL00052530.

Figure 13:
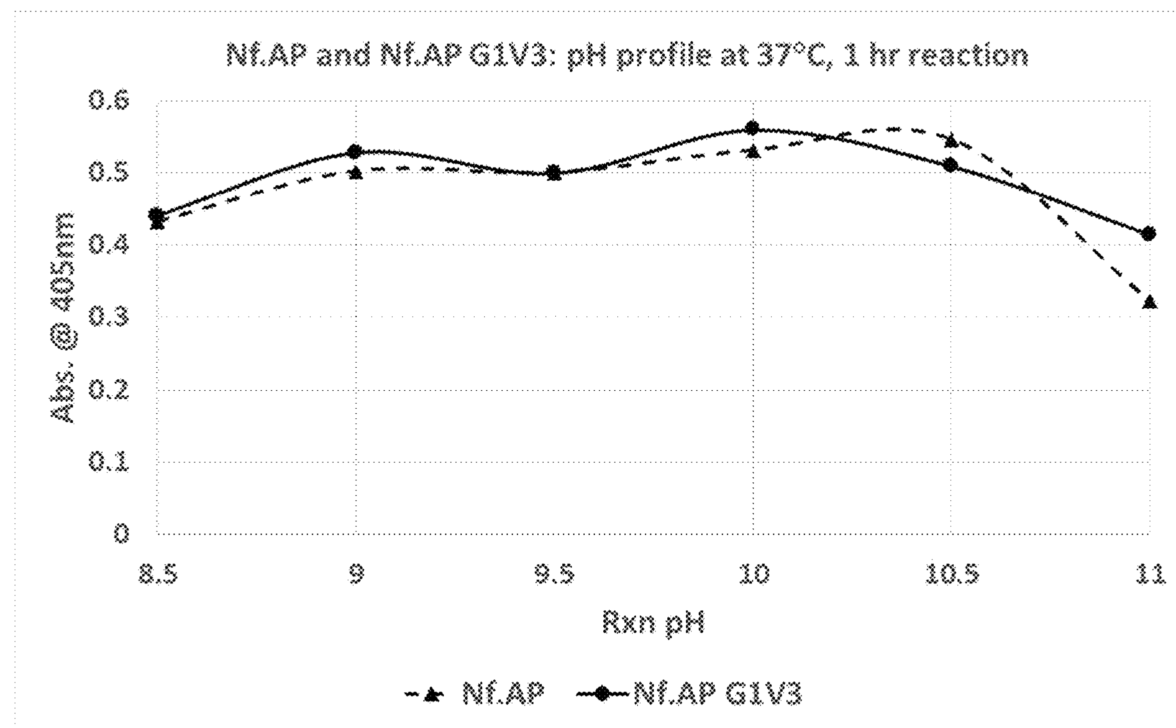

FIG. 13 provides data regarding pH profile of Nf.AP and Nf.AP G1V3 (colony tracking number: CL00052570) produced by *Pichia pastoris* at 37° C.

Figure 14:
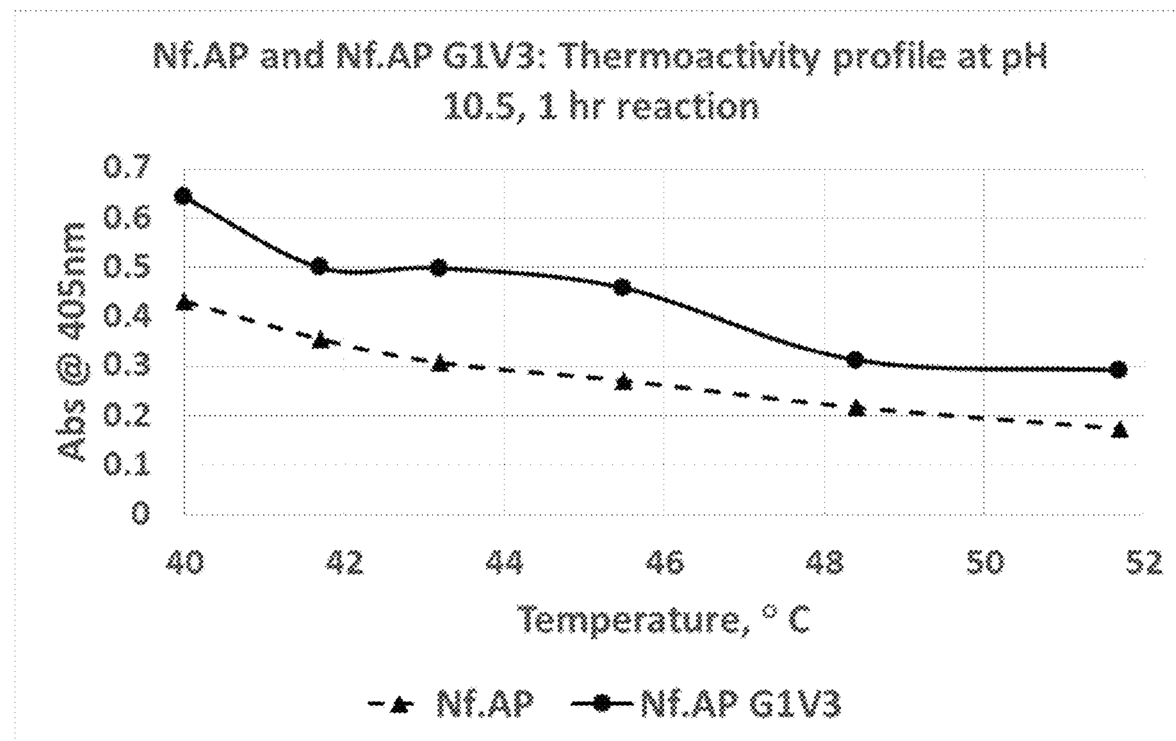

FIG. 14 provides data regarding thermoactivity profile of Nf.AP and Nf.AP G1V3 (colony tracking number: CL00052570) produced by *Pichia pastoris* at pH 10.5.

VII. DETAILED DESCRIPTION OF THE INVENTION

A. Introduction

Alkaline proteases are enzymes that catalyze the cleavage of peptide bonds in proteins. The optimum pH range of alkaline protease is generally between pH 9 and 11 with a few exceptions at higher pH (P Ellaiah, B Srinivasulu et al. 2002, Journal of Scientific & Industrial Research. 61:690-704). The optimum temperatures of alkaline proteases range between 50° C. and 70° C. with a few exceptions at even higher temperatures.

Alkaline proteases are robust enzymes with considerable industrial potential in various industrial fields, particularly in the production of detergents in the alkaline pH range, e.g. as additives to the laundry, dishwashing and contact tense solutions, because they can digest proteinaceous stains, such as keratin, blood, milk, and gravy etc. (Katsuhisa Saeki, Katsuya Ozaki, 2007, Journal of Bioscience and Bioengineering. 103(6): 501-508). For an enzyme to be used as a detergent additive, it should have at least two qualities: (1) An alkaline pH and (ii) it should also be compatible with detergents. For optimal performance, it should be stable at extreme temperatures, such as an elevated temperature during certain dishwashing or laundry process. In addition, it should also be stable for storage at room temperature and have broad substrate specificity (Adil Anwar, Mohammed Saleemuddin, 1998, Bioresource Technology. 64:175-183; Katsuhisa Saeki, Katsuya Ozaki, 2007, Journal of Bioscience and Bioengineering. 103(6): 501-508).

However, although alkaline proteases are active against many synthetic substrates as well as native proteins, reaction rates vary widely. Novel alkaline proteases are desired with increased activity, thermostability, pH stability as well as optimal performance in different ionic strengths (e.g. both soft and hard water), ability to withstand oxidizing and chelating agents and long shelf life at room temperature. The present invention meets this need and provides variant alkaline proteases with improved properties compared to parent alkaline proteases.

B. Definitions

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution A58G refers to a variant polypeptide, in this case an alkaline protease, in which the alanine at position 58 (sequence numbering starts from the mature position) is replaced with glycine. Multiple mutations are separated by forward slash marks ("/"), e.g., "K18R/A58G/N246G" representing substitutions at positions 18, 58 and 246, respectively. For clarity, a protein which has been engineered to change the nucleic acid coding sequence but not change the starting amino acid (for example, exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, −233E or 233E designates an insertion of glutamic acid after position 233 and before position 234. Additionally, −233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233− or E233#, E233( ) or E233del designates a deletion of glutamic acid at position 233. Additionally, EDA233− or EDA233# designates a deletion of the sequence GluAspAla that begins at position 233.

By "parent polypeptide/protein" or "parental polypeptide/protein" as used herein is meant a starting polypeptide/protein that is subsequently modified to generate a variant. The parent polypeptide/protein may be a naturally occurring polypeptide/protein, or a variant or engineered version of a naturally occurring polypeptide/protein. Parent polypeptide/protein may refer to the polypeptide/protein itself, compositions that comprise the parent polypeptide/protein, or the amino acid sequence that encodes it. In the present invention, some embodiments utilize the wild type enzymes, "Nf.AP" or "Ao.AP" as the parental enzyme. These are sometimes referred to herein as "G1P", as they are the first generation enzyme. Sometimes other enzymes, that contain amino acid substitutions, can be used as parent polypeptides/proteins.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about 15 amino acid modifications, and preferably from about one, two, three, five amino acid modifications compared to the parent. As described below, in some embodiments the parent polypeptide is a wild type sequence, designated "G1P" herein. As further discussed below, the protein variant sequence herein will preferably possess at least about 80% identity with a parent protein sequence, and most preferably at least about 90% identity, more preferably at least about 96-98-99% identity. Variant protein can refer to the variant protein itself, compositions comprising the protein variant, or the DNA sequence that encodes it. Thus, by "variant alkaline protease" herein is meant a novel alkaline protease that has at least one amino acid modification in the amino acid sequence as compared to a parent alkaline protease enzyme, and generally to the wild type parental enzyme, e.g. Nf.AP or Ao.AP. As discussed herein, in some cases the parent alkaline protease is a second or higher generation of variant. Unless otherwise noted or as will be obvious from the context, the variant alkaline proteases of the invention generally are compared to the wild type G1P sequence. Additionally, unless otherwise noted, the variant alkaline proteases of the invention are enzymatically active, that is, there is detectable alkaline proteases activity using an alkaline proteases assay (DMC-TNBS) described in the Examples section.

By "improved" (or "increased") herein is meant a desirable change of at least one biochemical property. "Improved function" or "improved activity" can be measured as a percentage increase or decrease of a particular activity, or as a "fold" change, with increases of desirable properties (e.g. pH stability, thermostability) or decreases of undesirable properties (e.g. protease sensitivity). That is, a variant may have a 10% increase in thermostability or a 10% decrease in protease sensitivity, as compared to G1P. Alternatively, a variant alkaline protease may have a 2-fold increase in pH stability or a 3-fold decrease in protease sensitivity. In general, percentage changes are used to describe changes in biochemical activity of less than 100%, and fold-changes are used to describe changes in biochemical activity of greater than 100% (as compared to the parental enzyme, in many cases G1P). In the present invention, percentage changes (usually increases) of biochemical activity of at least about 10%, 20%, 30%, 40%, 50%, 60%, 70%, 80%, 90%, 95%, 98% and 99% can be accomplished. In the present invention, a "fold increase" (or decrease) is measured as compared to the starting or parent enzyme. For example, as shown in the FIG. 4, G1V2 has a 7.00 fold increase in thermostability improvement as compared to G1P: this is calculated by [(activity of variant)/(activity of parent)]. In many embodiments, the improvement is at least one and a tenth fold (1.1), one and a half fold (1.5 fold), 2 fold, 3 fold, 4 fold, 5 fold, 6 fold, 7 fold, 8 fold, 9 fold, or 10 fold or higher.

As used herein, "protein" herein is meant at least two covalently attached amino acids, which includes proteins, polypeptides, oligopeptides and peptides. The peptidyl group generally comprise naturally occurring amino acids and peptide bonds. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Alanine 58 (also referred to as A58 or Ala58) is a residue at position 58 in the G1P parental enzyme of Ao AP (SEQ ID NO:2).

By "non-naturally occurring modification" as used herein is meant an amino acid modification that is not found in the wild type parent (e.g. G1P) enzyme.

By "amino acid" and "amino acid identity" as used herein is meant one of the 20 naturally occurring amino acids that are coded for by DNA and RNA.

By "position" as used herein is meant a location in the sequence of a protein. In general, the position number (which is more fully discussed below) is relative to the first amino acid of the mature alkaline protease sequence, e.g. excluding the signal peptide.

The term "alkaline protease(s)" (EC.3.4.21 24, 99) defined as protease enzyme(s) which are active in a neutral to alkaline pH range for catalyzing the cleavage of peptide bonds in both native proteins and synthetic substrates. They either have a serine center (serine protease) or are of metallo-type (metalloprotease). For purposes of the present invention, alkaline protease activity is determined according to the procedures described in the Examples herein, for example, the DMC-TNBS assay.

The term "coding sequence" refers to a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "expression" includes any step involved in the production of a variant alkaline protease described herein, including, but not limited to, transcription, post-transcriptional modification, translation, post-translational modification, and secretion.

The term "expression vector" refers to a linear or circular DNA molecule that comprises a polynucleotide encoding a variant and is operably linked to control sequences that provide for its expression.

The term "fragment" means a polypeptide having one or more (e.g., several) amino acids absent from the amino and/or carboxyl terminus of a mature polypeptide. A "alkaline protease fragment" herein means a portion of an amino acid sequence depicted herein that maintains alkaline protease activity. In one aspect, a fragment contains at least 50, at least 100, at least 150, at least 200, at least 250 or at least 280 amino acid residues. In some embodiments, the fragment is at least 200, at least 210, at least 220, at least 230, at least 240, at least 250, at least 260, at least 270 or at least 280 amino acid residues.

The term "host cell" refers to any cell type that is susceptible to transformation, transfection, transduction, or the like with a nucleic acid construct or expression vector comprising a polynucleotide of the present invention, and that allows for expression of the enzyme. The term "host cell" encompasses any progeny of a parent cell that is not identical to the parent cell due to mutations that occur during replication.

The term "improved property" refers to a characteristic associated with a variant alkaline protease enzyme described herein that is improved compared to the parent alkaline protease enzyme. Such improved properties include, but are not limited to, improved specific catalytic activity, substrate specificity, thermoactivity, thermostability (i.e., stability at higher temperature without change in the protein's chemical or physical structure), pH stability (e.g., increased stability at higher pH), as well as ability to withstand oxidizing and chelating agents. Further improved properties include, but are not limited to, improved stability at different ionic strengths (e.g. both soft and hard water), long shelf life at room temperature and broad substrate specificity.

The term "isolated" refers to a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance).

The term "mature polypeptide" means a polypeptide in its final form following translation and any post-translational modifications, such a N-terminal processing, C-terminal truncation, glycosylation, phosphorylation, etc.

The phrase "mature polypeptide coding sequence" refers to a polynucleotide that encodes a mature polypeptide having alkaline protease activity.

The term "nucleic acid construct" refers to a nucleic acd molecule, either single-stranded or double-stranded, which is isolated from a naturally occurring gene or is modified to contain segments of nucleic acids in a manner that would not otherwise exist in nature or which is synthetic, and which comprises one or more control sequences.

The term "operably linked" refers to a configuration in which a control sequence is placed at an appropriate position relative to the coding sequence of a polynucleotide such that the control sequence directs expression of the coding sequence.

The term "parent" or "parent alkaline protease" refers to an alkaline protease to which an alteration is made to produce the variant alkaline protease of the present invention. The parent may be a naturally occurring (wild-type) polypeptide or a variant or fragment thereof. The two exemplary parent polypeptides of the present invention are SEQ ID NO:1 and SEQ ID NO:2.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et at, 2000, Trends Genet. 16: 276-277), preferably version 6.1.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

This alignment for the purposes of determining percentage identity is done using the entire length of the sequence of the invention.

The term "variant" refers to a polypeptide having alkaline protease activity and which comprises an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

The term "wild-type" alkaline protease means an alkaline protease expressed by a naturally occurring microorganism, such as bacteria, fungi, yeast or certain insects found in nature. In general, the wild-type alkaline proteases of most interest herein are Nf.AP (SEQ ID NO:1) and Ao.AP (SEQ ID NO:2).

VIII. ALKALINE PROTEASE OF THE INVENTION

Accordingly, the present invention provides variant alkaline proteases with improved activity that can be used in detergent applications, for example, used as additives to laundry, dishwashing and/or contact lens detergent solutions for cleaning purposes.

In general, the variant alkaline proteases of the invention have modified, improved biochemical properties as compared to the wild type parent alkaline proteases, or "G1P" (e.g. "generation 1 parent"), for example Nf.AP (SEQ ID NO:1) or Ao.AP (SEQ ID NO:2) herein, as shown in FIG. 3. The biochemical properties of the variant alkaline proteases that can be improved herein include, but are not limited to, pH activity, pH stability, thermoactivity, thermostability, specific activity, formulation stability (including liquid, solid and pellets), ability to withstand oxidizing and chelating agents, activity at different ionic strengths (e.g. both soft and hard water), protease stability as well as long shelf life at room temperature.

The variant alkaline proteases of the invention have one or more improved properties as compared to G1P. The variant alkaline proteases of the invention can have an improvement in one or more of a number of biochemical properties, including, but not limited to, pH activity, pH stability, thermoactivity, thermostability, specific activity, formulation stability (including liquid, solid and pellets), ability to withstand oxidizing and chelating agents, activity at different ionic strengths (e.g. both soft and hard water), protease stability as well as long shelf life at room temperature. In general, improvements are measured as compared to the G1P enzyme using an alkaline protease activity assay, as outlined below, under conditions that challenge the variant alkaline proteases against the G1P enzyme.

A. Assays for the Determination of Improved Properties

As will be appreciated by those in the art, there are a number of different assays in the art that can be used to evaluate and quantify different improved properties, such as the Folin method, UV-vis method, DMC-TNBS Assay described below, etc.

1. DMC-TNBS Assay to Determine Alkaline Protease Activity

In some embodiments, a DMC-TNBS assay is employed to determine alkaline protease activity, such as the one described in the Examples section. First, the DMC substrate is prepared. Specifically, to 200 mL of boiling water, 3.20 g DMC is added and stirred. After heating the substrate for 20 minutes, it is cooled down at room temperature. In a separate beaker, 25.92 g sodium tetraborate decahydrate ($Na_2B_4O_7.10H_2O$) and 13.30 g sodium dihydrogen phosphate monohydrate ($NaH_2PO_4.H_2O$) is added to ~500 mL MQ water and stirred to dissolve. The DMC solution and the borate solution are mixed, and the volume bought up to 1 L. The pH is 8.00±0.05. The solution is filtered twice through filter paper and 600 μL of 30% Brij35 reagent is added. The final stock of DMC is 0.32% (w/v). The pH of substrate solution is adjusted between (8-11) using sodium hydroxide.

Then, 50 μl (final 0.21% w/v) N,N-dimethyl casein (DMC) solution (adjusted to pH 8-11 with sodium hydroxide) is added to each well of the reaction plate(s). 25 μL of the analyte solution is then added to each well. The plates are sealed and incubated at a specific temperature within a range of 35° C.-70° C. for 4 hrs. at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. DMC is used as a substrate. Alkaline protease reacts with DMC to release primary amine, and then the primary amine further reacts with TNBS. The absorbance change at 405 nm due to the reaction between formed primary amine and TNBS is monitored. The increase in absorbance is proportional to the reaction rate and thus to the enzyme activity.

Activity of an alkaline protease variant is compared to the parent alkaline protease enzyme under the same conditions to determine activity improvement. In some embodiments, the parent alkaline protease enzyme is a polypeptide of SEQ ID NO:1. In some embodiments, the parent alkaline protease enzyme is a polypeptide of SEQ ID NO:2.

As noted above, "improvement" in alkaline protease activity in this context is at least a 1.1 fold increase, with 1.5 fold, 2 fold, 2.5 fold, 3 fold, 3.5 fold, 4 fold, 4.5 fold, 5 fold, 5.5 fold or 6 fold increases all finding use in the present invention.

Alternatively, "improvement" can also be measured as a percentage increase, from 10%, 20%, 30%, 40%, 50%, 75%, 90%, 100%, 200%, 300%, 400%, 500% or 600% increases also finding use in the present invention.

2. Thermostability

In many embodiments, the variant alkaline proteases of the invention have improved thermostability, particularly under the washing or cleaning conditions used as detergent additives, such as under laundry-washing or dishwashing conditions, as is more fully outlined below. "Thermostability" in this context means that the variant enzymes are more stable than the parent alkaline protease (e.g. G1P) under the same thermal challenge conditions, that is, the activity of the variant is higher than that of the G1P under identical conditions (generally using the DMC-TNBS assay as outlined herein and as shown in Examples section but at different temperatures).

The variant alkaline proteases of the invention can exhibit improved thermostability as compared to SEQ ID NO:1 or a SEQ ID NO:2 at 20° C., 25° C., 30° C., 35° C., 40° C., 45° C., 50° C., 55° C., 60° C. and/or 65° C. for a period of time, generally ranging from about 2 minutes to 120 minutes or longer, depending on the use. For example, washing machine conditions (which may vary from country to country) may require stability for 10 minutes to 2 hours, depending on the cycle.

As discussed herein, "improved thermostability" in this context means retaining more activity over time than the corresponding wild type enzyme. As noted above, "improvement" in alkaline protease activity in this context is at least a 1.1 fold increase, with 1.5 fold, 2 fold, 2.5 fold, 3 fold, 3.5 fold, 4 fold, 4.5 fold, 5 fold, 5.5 fold or 6 fold increases all finding use in the present invention.

Alternatively, "improvement" can also be measured as a percentage increase, from 10%, 20%, 30%, 40%, 50%, 75%, 90%, 100%, 200%, 300%, 400%, 500% or 600% increases also finding use in the present invention.

Accordingly, as shown in the Figures, a number of variant alkaline proteases of the invention exhibit increased thermostability.

3. pH Stability

In many embodiments, the variant alkaline proteases of the invention have altered pH activity or stability as compared to the parent alkaline protease. "Improved pH stability" in this context means that the variant enzymes are more stable than the parent alkaline protease (e.g. G1P) under the same pH challenge conditions, that is, the activity of the variant is higher than that of the G1P under identical conditions (generally using the DMC-TNBS assay to determine the activity as outlined herein and as shown in Examples section). For example, DMC-TNBS assay can be done at a variety of pHs ranging from pH 8 to pH 12.

As discussed herein, "improved pH stability" in this context means retaining more activity over time than the corresponding wild type enzyme at a particular pH. As noted above, "improvement" in activity in this context is at least a 1.1 fold increase, with 1.5 fold, 2 fold, 2.5 fold, 3 fold, 3.5 fold, 4 fold, 4.5 fold, 5 fold, 5.5 fold or 6 fold increases all finding use in the present invention.

Alternatively, "improvement" can also be measured as a percentage increase, from 10%, 20%, 30%, 40%, 50%, 75%, 90%, 100%, 200%, 300%, 400%, 500% or 600% increases also finding use in the present invention.

4. Specific Activity Assays

In some embodiments, the variant alkaline proteases of the invention have increased specific activity as compared to a parent alkaline protease, particularly G1P. By "specific activity" herein is meant the activity per amount of enzyme, generally determined by dividing the enzymatic activity of a sample (sometimes measured in "alkaline protease units")

by the amount of alkaline protease enzyme, per unit time, generally determined as is known in the art.

In many embodiments, the variant alkaline proteases of the invention have improved specific activity as compared to the parent alkaline protease. "Improved specific activity" in this context means that the variant enzymes have more protease activity than the parent alkaline protease (e.g. G1P) under the same challenge conditions, that is, the activity of the variant is higher than that of the G1P under identical conditions (generally using the DMC-TNBS assay to determine the activity as outlined herein and as shown in Examples section.

As discussed herein, "improved specific activity" in this context means higher activity over time than the corresponding wild type enzyme at a particular challenge condition. As noted above, "improvement" in activity in this context is at least a 1.1 fold increase, with 1.5 fold, 2 fold, 2.5 fold, 3 fold, 3.5 fold, 4 fold, 4.5 fold, 5 fold, 5.5 fold or 6 fold increases all finding use in the present invention.

Alternatively, "improvement" can also be measured as a percentage increase, from 10%, 20%, 30%, 40%, 50%, 75%, 90%, 100%, 200%, 300%, 400%, 500% or 600% increases also finding use in the present invention.

5. Protease Susceptibility

In some embodiments, the variant alkaline proteases of the invention are less susceptible to protease degradation than the parent enzyme under identical conditions. In some cases, protease degradation during the production of variant alkaline proteases in a production host organism by protease enzymes produced by the host organism can be a problem, thus resulting in lower yield of active enzyme. Similarly, depending on the use of the variant enzymes, for example in detergent application, there may be other proteases present in the raw substrates or other enzymes for use in combination that can degrade the alkaline protease during the storage or cleaning process.

This is generally determined as is known in the art, for example by allowing proteolytic degradation and then doing N-terminal sequencing on the resulting fragments to determine the cleavage site(s). In some cases, depending on the variant and the host production organism, there may not be significant proteolytic degradation.

6. Assays to Determine Other Properties

Many assays in the art including but not being limited to those disclosed above (e.g. DMC-TNBS Assay) can be used to test and determine properties (e.g. activity, stability, specificity etc.) of the variant alkaline proteases of the invention as compared to the parent alkaline protease under various conditions, such as high/low ionic strength, in the presence of oxidizing and/or chelating agents, long duration at room temperature, washing conditions, in the presence of different substrates, etc.

In some embodiments, the variant alkaline proteases of the invention have improved alkaline protease activity and stability as compared to the parent alkaline protease under the same ionic strength condition (e.g. soft and/or hard water). "Improved alkaline protease activity and stability under the same ionic strength condition" in this context means that the variant enzymes are more stable than the parent alkaline protease (e.g. G1P) under the same ionic strength condition, that is, the activity of the variant is higher than that of the G1P under identical conditions.

In some embodiments, the variant alkaline proteases of the invention have higher ability or stability to withstand oxidizing and/or chelating agents (e.g. those in the formulated detergent) than the parent alkaline protease. "Higher ability or stability to withstand oxidizing and/or chelating agents" in this context means that the variant enzymes are more stable than the parent alkaline protease (e.g. G1P) under the same conditions, i.e. in the presence of oxidizing and/or chelating agents, that is, the activity of the variant is higher than that of the G1P under identical conditions.

In some embodiments, the variant alkaline proteases of the invention have longer shelf life at room temperature than the parent alkaline protease. "Longer shelf life at room temperature" in this context means that the variant enzymes are more stable than the parent alkaline protease (e.g. G1P) under the same room temperature, that is, the variant enzymes retain more activity over time than the corresponding wild type enzyme under identical conditions.

In some embodiments, the variant alkaline proteases of the invention have broader substrate specificity than the parent alkaline protease. "Broader substrate specificity" in this context means that the variant enzymes have higher number of specific substrates than the parent alkaline protease (e.g. G1P).

In some embodiments, the variant alkaline proteases of the invention have improved washing performance on stains as compared to the parent alkaline protease. "Improved washing performance on stains" in this context means that the variant enzymes have higher ability to clean the same stain than the parent alkaline protease (e.g. G1P) under the same washing conditions, that is, the activity of the variant is higher than that of the G1P under identical conditions.

The "improved properties" as discussed above (e.g. "improved alkaline protease activity and stability under the same ionic strength condition", "higher ability or stability to withstand oxidizing and/or chelating agents", "longer shelf life at room temperature", "broader substrate specificity", "improved washing performance on stains") is at least a 1.1 fold increase, with 1.5 fold, 2 fold, 2.5 fold, 3 fold, 3.5 fold, 4 fold, 4.5 fold, 5 fold, 5.5 fold or 6 fold increases as compared to a parent enzyme, which all find use in the present invention. Alternatively, these "improved properties" can also be measured as a percentage increase, from 10%, 20%, 30%, 40%, 50%, 75%, 90%, 100%, 200%, 300%, 400%, 500% or 600% increases as compared to a parent enzyme also finding use in the present invention.

IX. SPECIFIC VARIANT ALKALINE PROTEASES

The present invention provides variant alkaline protease enzymes comprising amino acid substitution(s) at one or more (e.g., several) positions as compared to the alkaline protease enzymes of either SEQ ID NO:1 or SEQ ID NO:2.

In some embodiments, the parent alkaline protease enzyme is SEQ ID NO:1. In some embodiments, the amino acid substitution (s) occur at one or more positions 18, 21, 24, 53, 58, 77, 87, 91, 117, 130, 183, 197, 203, 234, 246 and 275 as compared to a parent alkaline protease enzyme. In some embodiments, the variant has at least 75%, at least 80%, at least 85%, at least 90%, at least 95%, at least 96%, at least 97%, at least 98%, or at least 99%, but less than 100% sequence identity to the polypeptide of SEQ ID NO:1.

In some embodiments, the parent alkaline protease enzyme is SEQ ID NO:2. In some embodiments, the amino acid substitution (s) occur at one or more positions 18, 21, 58, 77, 87, 117, 183, 197, 203, and 234 as compared to a parent alkaline protease enzyme. In some embodiments, the variant has at least 75%, at least 80%, at least 85%, at least 90%, at least 95%, at least 96%, at least 97%, at least 98%, or at least 99%, but less than 100% sequence identity to the polypeptide of SEQ ID NO:2.

To be clear, the variant alkaline proteases of the invention neither have SEQ ID NO:1 nor SEQ ID NO:2. Additionally, specifically excluded from the definition of variant alkaline proteases are any of the homologs to Nf.AP and Ao.AP as shown in FIGS. 7 and 8 (i.e. those homologs with the Accession numbers of AAB07672.1, PRF:1905286A, XP_001266852.1, GAQ08309.1, CAA75804.1, PKX92603.1, GA083403.1, OX505387.1, CAA75806.1, AAT85626.1, OXN40493.1, AAT85627.1, OXN19152.1, PRF:1410167A, AAD47202.1, KJK65194.1, PIG88895.1, XP_022392829.1, and XP_015409892.1). Additionally, unless otherwise noted, the variant alkaline proteases of the present invention have alkaline protease activity.

In some embodiments, the variant alkaline protease enzyme exhibits at least 80%, at least 85%, at least 90%, at least 91%, at least 92%, at least 93%, at least 94%, at least 95%, at least 96%, at least 97%, at least 98%, or at least 99%, but less than 100%, sequence identity to the amino acid sequence of the parent alkaline protease, and the variant alkaline protease enzyme is not any one of the following homologs with the Accession numbers of AAB07672.1, PRF:1905286A, XP_001266852.1, GAQ08309.1, CAA75804.1, PKX92603.1, GA083403.1, OXS05387.1, CAA75806.1, AAT85626.1, OXN40493.1, AAT85627.1, OXN19152.1, PRF:1410167A, AAD47202.1, KJK65194.1, PIG88895.1, XP_022392829.1, and XP_015409892.1.

A. Specific Variants of SEQ ID NO:1

In some embodiments, the variant alkaline protease enzymes comprise amino acid substitution(s) at one or more (e.g., several) positions corresponding to positions 18, 21, 24, 53, 58, 91, 130, 234, 246 and 275 as compared to a parent alkaline protease enzyme of SEQ ID NO:1.

In some embodiments, the variant alkaline protease enzymes comprise one or more (e.g., several) substitutions selected from the group consisting of K18R, A21G, D24H, S53G, A58G, T91A, A130V, I234V, N246G and K275L as compared to a parent alkaline protease enzyme of SEQ ID NO:1.

In some embodiments, the variant alkaline protease enzymes comprise one or more variants selected from FIG. 4.

In some embodiments, the variant alkaline protease enzyme is an isolated variant alkaline protease enzyme.

In some embodiments, the variant alkaline protease enzyme exhibits at least 80%, at least 85%, at least 90%, at least 91%, at least 92%, at least 93%, at least 94%, at least 95%, at least 96%, at least 97%, at least 98%, or at least 99%, but less than 100%, sequence identity to the amino acid sequence of the parent alkaline protease of SEQ ID NO:1, and the variant alkaline protease enzyme is not any one of the following homologs with the Accession numbers of AAB07672.1, PRF:1905286A, XP_001266852.1, GAQ08309.1, CAA75804.1, PKX92603.1, GAO83403.1, OXS05387.1, CAA75806.1, AAT85626.1, OXN40493.1, AAT85627.1, and OXN19152.1. In some embodiments, the variant alkaline protease enzyme as described herein exhibits at least 96%, at least 97%, at least 98%, or at least 99%, but less than 100%, sequence identity to the amino acid sequence of the parent alkaline protease of SEQ ID NO:1.

In some embodiments, the variant alkaline protease enzyme comprises at least one amino acid substitution at position(s) selected from the group consisting of 18, 21, 24, 53, 58, 77, 87, 91, 117, 130, 183, 197, 203, 234, 246 and 275 as compared to a parent alkaline protease enzyme. In some cases, the variant enzyme can comprise 1, 2, 3, 4, 5, 6, 7, 8, 9, or 10 amino acid substitutions at these positions. In some cases, the variant enzyme can comprise 1, 2, 3, 4, or 5 amino acid substitutions at these positions.

In some embodiments, the variant alkaline protease enzyme comprises at least one amino acid substitution at position(s) selected from the group consisting of 18, 21, 24, 53, 58, 91, 130, 234, 246 and 275 as compared to a parent alkaline protease enzyme of SEQ ID NO:1. In some cases, the variant enzyme can comprise 1, 2, 3, 4, 5, 6, 7, 8, 9, or 10 amino acid substitutions at these positions. In some cases, the variant enzyme can comprise 1, 2, 3, 4, or 5 amino acid substitutions at these positions.

In some embodiments, the variant alkaline protease enzyme comprises at least one substitution at position(s) selected from the group consisting of K18R, A21G, D24H, S53G, A58G, T91A, A130V, I234V, N246G and K275L as compared to a parent alkaline protease enzyme of SEQ ID NO:1. In some cases, the variant enzyme can comprise 1, 2, 3, 4, 5, 6, 7, 8, 9, or 10 amino acid substitutions at these positions. In some cases, the variant enzyme can comprise 1, 2, 3, 4, or 5 amino acid substitutions at these positions.

In some embodiments, the variant alkaline protease comprises at least one amino acid substitution as compared to SEQ ID NO:2, wherein said variant alkaline protease enzyme has alkaline protease activity, and wherein said amino acid substitution is selected from the group consisting of: K18R, Q21G, A58G, S77A, I87V, A117V, A183G, F197Y, V203I, and I234V.

In some embodiments, the variant alkaline protease comprises at least one amino acid substitution as compared to SEQ ID NO:1, wherein said variant alkaline protease enzyme has alkaline protease activity, wherein said amino acid substitution is selected from the group consisting of: K18R, A21G, D24H, S53G, A58G, T91A, A130V, I234V, N246G and K275L, and wherein said variant alkaline protease enzyme exhibits at least 96% identity to SEQ ID NO:1.

In some embodiments, the variant alkaline protease comprises at least one amino acid substitution as compared to SEQ ID NO:1, wherein said amino acid substitution is selected from the group consisting of: K18R, A21G, D24H, S53G, A58G, T91A, A130V, I234V, N246G and K275L, wherein said variant alkaline protease enzyme exhibits at least 96% identity to SEQ ID NO:1, and wherein said variant enzyme has at least 1.1 fold better alkaline protease activity as compared to SEQ ID NO:1 under a condition selected from the group consisting of thermostability at 20° C., thermostability at 25° C., thermostability at 30° C., thermostability at 35° C., thermostability at 40° C., thermostability at 45° C., thermostability at 50° C., thermostability at 55° C., thermostability at 60° C. and thermostability at 65° C.

In some embodiments, the variant alkaline protease comprises at least one amino acid substitution as compared to SEQ ID NO:1, wherein said amino acid substitution is selected from the group consisting of: K18R, A21G, D24H, S53G, A58G, T91A, A130V, I234V, N246G and K275L, wherein said variant alkaline protease enzyme exhibits at least 96% identity to SEQ ID NO:1, and wherein said variant enzyme has at least 1.1 fold better alkaline protease activity as compared to SEQ ID NO:1 under a condition selected from the group consisting of thermostability at 37° C., thermostability at 40° C., thermostability at 45° C., thermostability at 50° C., thermostability at 52° C. and thermostability at 55° C.

In some embodiments, the variant alkaline protease comprises at least one amino acid substitution as compared to SEQ ID NO:1, wherein said amino acid substitution is selected from the group consisting of: K18R, A21G, D24H, S53G, A58G, T91A, A130V, I234V, N246G and K275L, wherein said variant alkaline protease enzyme exhibits at least 96% identity to SEQ ID NO:1, and wherein said variant enzyme has at least 1.1 fold better alkaline protease activity as compared to SEQ ID NO:1 under a condition selected from the group consisting of pH at 8, pH at 8.5, pH at 9, pH at 9.5, pH at 10, pH at 10.5, pH at 11, pH at 11.5 and pH at 12.

In some embodiments, the variant alkaline protease comprises at least one amino acid substitution as compared to SEQ ID NO:1, wherein said amino acid substitution is selected from the group consisting of: K18R, A21G, D24H, S53G, A58G, T91A, A130V, I234V, N246G and K275L, wherein said variant alkaline protease enzyme exhibits at least 96% identity to SEQ ID NO:1, and wherein said variant enzyme has at least 1.1 fold better alkaline protease activity as compared to SEQ ID NO:1 under a condition selected from the group consisting of pH at 9, pH at 10, pH 10.5, pH at 11 and pH at 11.3.

In some embodiments, the variant alkaline protease enzyme as described herein exhibits at least 97%, 98%, or 99% identity to SEQ ID NO:1.

In some embodiments, the variant alkaline protease enzyme as described herein has one of said amino acid substitution, two of said amino acid substitutions, three of said amino acid substitutions, four of said amino acid substitutions, five of said amino acid substitutions, six of said amino acid substitutions, seven of said amino acid substitutions, eight of said amino acid substitutions, nine of said amino acid substitutions, or ten of said amino acid substitutions.

In some embodiments, the variant alkaline protease enzyme comprises an amino acid substitution at position 18. In some embodiments, the substitution is with any other of the 19 naturally occurring amino acids, namely serine, threonine, asparagine, glutamine, aspartic acid, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 18 is substituted with arginine (R). In some embodiments, the lysine (K) at position 18 is substituted with arginine (R). In some embodiments, the variant alkaline protease enzyme comprises or consists of the substitution K18R of SEQ ID NO:1.

In some embodiments, the variant alkaline protease enzyme comprises an amino acid substitution at position 21. In some embodiments, the substitution is with any other of the 19 naturally occurring amino acids, namely serine, threonine, asparagine, glutamine, aspartic acid, lysine, arginine, histidine, glutamic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 21 is substituted with glycine (G). In some embodiments, the alanine (A) at position 21 is substituted with glycine (G). In some embodiments, the variant alkaline protease enzyme comprises or consists of the substitution A21G of SEQ ID NO:1.

In some embodiments, the variant alkaline protease enzyme comprises an amino acid substitution at position 24. In some embodiments, the substitution is with any other of the 19 naturally occurring amino acids, namely serine, threonine, asparagine, glutamine, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 24 is substituted with histidine (H). In some embodiments, the aspartic acid (D) at position 24 is substituted with histidine (H). In some embodiments, the variant alkaline protease enzyme comprises or consists of the substitution D24H of SEQ ID NO:1.

In some embodiments, the variant alkaline protease enzyme comprises an amino acid substitution at position 53. In some embodiments, the substitution is with any other of the 19 naturally occurring amino acids, namely threonine, asparagine, glutamine, aspartic acid, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 53 is substituted with glycine (G). In some embodiments, the serine (S) at position 53 is substituted with glycine (G). In some embodiments, the variant alkaline protease enzyme comprises or consists of the substitution S53G of SEQ ID NO:1.

In some embodiments, the variant alkaline protease enzyme comprises an amino acid substitution at position 58. In some embodiments, the substitution is with any other of the 19 naturally occurring amino acids, namely serine, threonine, asparagine, glutamine, aspartic acid, lysine, arginine, histidine, glutamic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 58 is substituted with glycine (G). In some embodiments, the alanine (A) at position 58 is substituted with glycine (G). In some embodiments, the variant alkaline protease enzyme comprises or consists of the substitution A58G of SEQ ID NO:1.

In some embodiments, the variant alkaline protease enzyme comprises an amino acid substitution at position 91. In some embodiments, the substitution is with any other of the 19 naturally occurring amino acids, namely serine, asparagine, glutamine, aspartic acid, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 91 is substituted with alanine (A). In some embodiments, the threonine (T) at position 91 is substituted with alanine (A). In some embodiments, the variant alkaline protease enzyme comprises or consists of the substitution T91A of SEQ ID NO:1.

In some embodiments, the variant alkaline protease enzyme comprises an amino acid substitution at position 130. In some embodiments, the substitution is with any other of the 19 naturally occurring amino acids, namely serine, threonine, asparagine, glutamine, aspartic acid, lysine, arginine, histidine, glutamic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 130 is substituted with valine (V). In some embodiments, the alanine (A) at position 130 is substituted with valine (V). In some embodiments, the variant alkaline protease enzyme comprises or consists of the substitution A130V of SEQ ID NO:1.

In some embodiments, the variant alkaline protease enzyme comprises an amino acid substitution at position 234. In some embodiments, the substitution is with any other of the 19 naturally occurring amino acids, namely serine, threonine, asparagine, glutamine, aspartic acid, lysine, arginine, histidine, glutamic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid at position 234 is substituted with valine (V). In some embodiments, the isoleucine (I) at position 234 is substituted with valine (V). In some embodiments, the variant alkaline protease enzyme comprises or consists of the substitution I234V of SEQ ID NO:1.

In some embodiments, the variant alkaline protease enzyme comprises an amino acid substitution at position 246. In some embodiments, the substitution is with any other of the 19 naturally occurring amino acids, namely serine, threonine, glutamine, aspartic acid, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 246 is substituted with glycine (G). In some embodiments, the asparagine (N) at position 246 is substituted with glycine (G). In some embodiments, the variant alkaline protease enzyme comprises or consists of the substitution N246G of SEQ ID NO:1.

In some embodiments, the variant alkaline protease enzyme comprises an amino acid substitution at position 275. In some embodiments, the substitution is with any other of the 19 naturally occurring amino acids, namely serine, threonine, asparagine, glutamine, aspartic acid, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 275 is substituted with leucine (L). In some embodiments, the lysine (K) at position 275 is substituted with leucine (L). In some embodiments, the variant alkaline protease enzyme comprises or consists of the substitution K275L of SEQ ID NO:1.

In some embodiments, the variant alkaline protease enzyme as described herein comprises the amino acid substitutions selected from the group consisting of: K18R/A58G/N246G, K18R/I234V, K18R/A21G/S53G/A58G/K275L, K18R/S53G/A130V/I234V, K18R/A58G, K18R/T91A/I234V/N246G/K275L, K18R/A21G/A58G/I234V, K18R/S53G, K18R/A21G, K18R, K18R/A21G/I234V/N246G, K18R/S53G/A58G/I234V, K18R/S53G/T91A, K18R/A58G/I234V/K275L, K18R/I234V/K275L, A21G/S53G/K275L, K18R/A58G/K275L, K18R/A21G/A58G, K18R/D24H/S53G/A58G/A130V, K18R/S53G/A130V/K275L and K18R/S53G/T91A/I234V/K275L as compared to SEQ ID NO:1.

In some embodiments, the variant alkaline protease enzyme as described herein comprises the amino acid substitutions selected from the group consisting of: K18R/A58G/N246G, K18R/I234V, K18R/A21G/S53G/A58G/K275L, K18R/S53G/A130V/I234V, K18R/A58G, K18R/T91A/I234V/N246G/K275L, K18R/A21G/A58G/I234V, K18R/S53G, K18R/A21G, K18R, K18R/A21G/I234V/N246G, K18R/S53G/A58G/I234V, K18R/S53G/T91A, K18R/A58G/I234V/K275L, K18R/I234V/K275L, A21G/S53G/K275L, K18R/A58G/K275L, K18R/A21G/A58G, K18R/D24H/S53G/A58G/A130V, K18R/S53G/A130V/K275L and K18R/S53G/T91A/I234V/K275L as compared to SEQ ID NO:1 and are at least 96%, 97%, 98% or 99% identical to SEQ ID NO:1.

In some embodiments, the variant alkaline protease enzyme as described herein comprises the amino acid substitutions selected from the group consisting of: K18R/A58G/N246G, K18R/I234V, K18R/S53G/A130V/I234V and K18R/A58G as compared to SEQ ID NO:1, and are at least 96%, 97%, 98% or 99% identical to SEQ ID NO:1.

In some embodiments, the variant alkaline protease enzyme as described herein comprises amino acid substitutions K18R/I234V as compared to SEQ ID NO:1, and exhibits at least 90% identity to SEQ ID NO:3.

In some embodiments, the variant alkaline protease enzyme as described herein has an amino acid sequence of SEQ ID NO:3.

In some embodiments, the variant alkaline protease enzyme as described herein comprises amino acid substitutions K18R/A58G/N246G as compared to SEQ ID NO:1, and exhibits at least 90% identity to SEQ ID NO:5.

In some embodiments, the variant alkaline protease enzyme as described herein has an amino acid sequence of SEQ ID NO:5.

In some embodiments, the variant alkaline protease enzyme as described herein comprises amino acid substitutions K18R/S53G/A130V/I234V, and exhibits at least 90% identity to SEQ ID NO:6.

In some embodiments, the variant alkaline protease enzyme as described herein has an amino acid sequence of SEQ ID NO:6.

In some embodiments, the variant alkaline protease enzyme as described herein comprises amino acid substitutions K18R/A58G, and exhibits at least 90% identity to SEQ ID NO:7.

In some embodiments, the variant alkaline protease enzyme as described herein has an amino acid sequence of SEQ ID NO:7.

In some embodiments, the variant alkaline protease enzyme comprises the amino acid substitutions of K18R/A58G/N246G as compared to SEQ ID NO:1. In some embodiments, the variant alkaline protease enzyme comprises the amino acid substitution of K18R/A58G/N246G, are at least 95%, 96%, 97%, 98% or 99% identical to SEQ ID NO:1.

In some embodiments, the variant alkaline protease enzyme comprises the amino acid substitution of K18R/I234V as compared to SEQ ID NO:1. In some embodiments, the variant alkaline protease enzyme comprises the amino acid substitution of K18R/I234V, and are at least 95%, 96%, 97%, 98% or 99% identical to SEQ ID NO:1.

In some embodiments, the variant alkaline protease enzyme comprises the amino acid substitution of K18R/A21G/S53G/A58G/K275L as compared to SEQ ID NO:1. In some embodiments, the variant alkaline protease enzyme comprises the amino acid substitution of K18R/A21G/S53G/A58G/K275L, and are at least 95%, 96%, 97%, 98% or 99% identical to SEQ ID NO:1.

In some embodiments, the variant alkaline protease enzyme comprises the amino acid substitution of K18R/S53G/A130V/I234V as compared to SEQ ID NO:1. In some embodiments, the variant alkaline protease enzyme comprises the amino acid substitution of K18R/S53G/A130V/I234V, and are at least 95%, 96%, 97%, 98% or 99% identical to SEQ ID NO:1.

In some embodiments, the variant alkaline protease enzyme comprises the amino acid substitution of K18R/A58G as compared to SEQ ID NO:1. In some embodiments, the variant alkaline protease enzyme comprises the amino acid substitution of K18R/A58G, and are at least 95%, 96%, 97%, 98% or 99% identical to SEQ ID NO:1.

In some embodiments, the variant alkaline protease enzyme comprises the amino acid substitution of K18R/T91A/I234V/N246G/K275L as compared to SEQ ID NO:1. In some embodiments, the variant alkaline protease enzyme comprises the amino acid substitution of K18R/T91A/I234V/N246G/K275L, and are at least 95%, 96%, 97%, 98% or 99% identical to SEQ ID NO:1.

In some embodiments, the variant alkaline protease enzyme comprises the amino acid substitution of K18R/A21G/A58G/I234V as compared to SEQ ID NO:1. In some embodiments, the variant alkaline protease enzyme comprises the amino acid substitution of K18R/A21G/A58G/I234V, and are at least 95%, 96%, 97%, 98% or 99% identical to SEQ ID NO:1.

In some embodiments, the variant alkaline protease enzyme comprises the amino acid substitution of K18R/S53G as compared to SEQ ID NO:1. In some embodiments, the variant alkaline protease enzyme comprises the amino acid substitution of K18R/S53G, and are at least 95%, 96%, 97%, 98% or 99% identical to SEQ ID NO:1.

In some embodiments, the variant alkaline protease enzyme comprises the amino acid substitution of K18R/A21G as compared to SEQ ID NO:1. In some embodiments, the variant alkaline protease enzyme comprises the amino acid substitution of K18R/A21G, and are at least 95%, 96%, 97%, 98% or 99% identical to SEQ ID NO:1.

In some embodiments, the variant alkaline protease enzyme comprises the amino acid substitution of K18R as compared to SEQ ID NO:1. In some embodiments, the variant alkaline protease enzyme comprises the amino acid substitution of K18R, and are at least 95%, 96%, 97%, 98% or 99% identical to SEQ ID NO:1.

In some embodiments, the variant alkaline protease enzyme comprises the amino acid substitution of K18R/A21G/I234V/N246G as compared to SEQ ID NO:1. In some embodiments, the variant alkaline protease enzyme comprises the amino acid substitution of K18R/A21G/I234V/N246G, and are at least 95%, 96%, 97%, 98% or 99% identical to SEQ ID NO:1.

In some embodiments, the variant alkaline protease enzyme comprises the amino acid substitution of K18R/S53G/A58G/I234V as compared to SEQ ID NO:1. In some embodiments, the variant alkaline protease enzyme comprises the amino acid substitution of K18R/S53G/A58G/I234V, and are at least 95%, 96%, 97%, 98% or 99% identical to SEQ ID NO:1.

In some embodiments, the variant alkaline protease enzyme comprises the amino acid substitution of K18R/S53G/T91A as compared to SEQ ID NO:1. In some embodiments, the variant alkaline protease enzyme comprises the amino acid substitution of K18R/S53G/T91A, and are at least 95%, 96%, 97%, 98% or 99% identical to SEQ ID NO:1.

In some embodiments, the variant alkaline protease enzyme comprises the amino acid substitution of K18R/A58G/I234V/K275L as compared to SEQ ID NO:1. In some embodiments, the variant alkaline protease enzyme comprises the amino acid substitution of K18R/A58G/I234V/K275L, and are at least 95%, 96%, 97%, 98% or 99% identical to SEQ ID NO:1.

In some embodiments, the variant alkaline protease enzyme comprises the amino acid substitution of K18R/I234V/K275L as compared to SEQ ID NO:1. In some embodiments, the variant alkaline protease enzyme comprises the amino acid substitution of K18R/I234V/K275L, and are at least 95%, 96%, 97%, 98% or 99% identical to SEQ ID NO:1.

In some embodiments, the variant alkaline protease enzyme comprises the amino acid substitution of A21G/S53G/K275L as compared to SEQ ID NO:1. In some embodiments, the variant alkaline protease enzyme comprises the amino acid substitution of A21G/S53G/K275L, and are at least 95%, 96%, 97%, 98% or 99% identical to SEQ ID NO:1.

In some embodiments, the variant alkaline protease enzyme comprises the amino acid substitution of K18R/A58G/K275L as compared to SEQ ID NO:1. In some embodiments, the variant alkaline protease enzyme comprises the amino acid substitution of K18R/A58G/K275L, and are at least 95%, 96%, 97%, 98% or 99% identical to SEQ ID NO:1.

In some embodiments, the variant alkaline protease enzyme comprises the amino acid substitution of K18R/A21G/A58G as compared to SEQ ID NO:1. In some embodiments, the variant alkaline protease enzyme comprises the amino acid substitution of K18R/A21G/A58G, and are at least 95%, 96%, 97%, 98% or 99% identical to SEQ ID NO:1.

In some embodiments, the variant alkaline protease enzyme comprises the amino acid substitution of K18R/D24H/S53G/A58G/A130V as compared to SEQ ID NO:1. In some embodiments, the variant alkaline protease enzyme comprises the amino acid substitution of K18R/D24H/S53G/A58G/A130V, and are at least 95%, 96%, 97%, 98% or 99% identical to SEQ ID NO:1.

In some embodiments, the variant alkaline protease enzyme comprises the amino acid substitution of K18R/S53G/A130V/K275L as compared to SEQ ID NO:1. In some embodiments, the variant alkaline protease enzyme comprises the amino acid substitution of K18R/S53G/A130V/K275L, and are at least 95%, 96%, 97%, 98% or 99% identical to SEQ ID NO:1.

In some embodiments, the variant alkaline protease enzyme comprises the amino acid substitution of K18R/S53G/T91A/I234V/K275L as compared to SEQ ID NO:1. In some embodiments, the variant alkaline protease enzyme comprises the amino acid substitution of K18R/S53G/T91A/I234V/K275L, and are at least 95%, 96%, 97%, 98% or 99% identical to SEQ ID NO:1.

B. Specific Variants of SEQ ID NO:2

In some embodiments, the variant alkaline protease enzymes comprise amino acid substitution(s) at one or more (e.g., several) positions corresponding to positions 18, 21, 58, 77, 87, 117, 183, 197, 203 and 234 as compared to a parent alkaline protease enzyme of SEQ ID NO:2.

In some embodiments, the variant alkaline protease enzymes comprise one or more (e.g., several) substitutions selected from the group consisting of K18R, Q21G, A58G, S77A, I87V, A117V, A183G, F197Y, V203I, and I234V as compared to a parent alkaline protease enzyme of SEQ ID NO:2.

In some embodiments, the variant alkaline protease enzymes comprise one or more variants selected from FIG. 5.

In some embodiments, the variant alkaline protease enzyme is an isolated variant alkaline protease enzyme.

In some embodiments, the variant alkaline protease enzyme exhibits at least 80%, at least 85%, at least 90%, at least 91%, at least 92%, at least 93%, at least 94%, at least 95%, at least 96%, at least 97%, at least 98%, or at least 99%, but less than 100%, sequence identity to the amino acid sequence of the parent alkaline protease of SEQ ID NO:2, and the variant alkaline protease enzyme is not any one of the following homologs with the Accession numbers of PRF:1410167A, AAD47202.1, KJK65194.1, PIG88895.1, XP_022392829.1, and XP_015409892.1.

In some embodiments, the variant alkaline protease enzyme comprises at least one amino acid substitution at positions selected from the group consisting of 18, 21, 58, 77, 87, 117, 183, 197, 203 and 234 as compared to a parent alkaline protease enzyme of SEQ ID NO:2. In some cases, the variant enzyme can comprise 1, 2, 3, 4, 5, 6, 7, 8, 9, or 10 amino acid substitutions at these positions. In some cases, the variant enzyme can comprise 1, 2, 3, 4, or 5 amino acid substitutions at these positions.

In some embodiments, the variant alkaline protease enzyme comprises at least one substitution at position(s) selected from the group consisting of K18R, Q21G, A58G, S77A, I87V, A117V, A183G, F197Y, V203I, and I234V as compared to a parent alkaline protease enzyme of SEQ ID NO:2. In some cases, the variant enzyme can comprise 1, 2, 3, 4, 5, 6, 7, 8, 9, or 10 amino acid substitutions at these positions. In some cases, the variant enzyme can comprise 1, 2, 3, 4, or 5 amino acid substitutions at these positions.

In some embodiments, the variant alkaline protease comprises at least one amino acid substitution as compared to SEQ ID NO:2, wherein said variant alkaline protease enzyme has alkaline protease activity, and wherein said amino acid substitution is selected from the group consisting of: K18R, Q21G, A58G, S77A, I87V, A117V, A183G, F197Y, V203I, and I234V.

In some embodiments, the variant alkaline protease comprises at least one amino acid substitution as compared to SEQ ID NO:2, wherein said variant alkaline protease enzyme has alkaline protease activity, wherein said amino acid substitution is selected from the group consisting of: K18R, Q21G, A58G, S77A, I87V, A117V, A183G, F197Y, V203I, and I234V, and wherein said variant alkaline protease enzyme exhibits at least 98% identity to SEQ ID NO:2.

In some embodiments, the variant alkaline protease comprises at least one amino acid substitution as compared to SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzyme exhibits at least 98% identity to SEQ ID NO:2, and wherein said variant enzyme has at least 1.1 fold better alkaline protease activity as compared to SEQ ID NO:2 under a condition selected from the group consisting of thermostability at 20° C., thermostability at 25° C., thermostability at 30° C., thermostability at 35° C., thermostability at 40° C., thermostability at 45° C., thermostability at 50° C., thermostability at 55° C., thermostability at 60° C. and thermostability at 65° C.

In some embodiments, the variant alkaline protease comprises at least one amino acid substitution as compared to SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzyme exhibits at least 98% identity to SEQ ID NO:2, and wherein said variant enzyme has at least 1.1 fold better alkaline protease activity as compared to SEQ ID NO:2 under a condition of thermostability at 37° C. or thermostability at 40° C.

In some embodiments, the variant alkaline protease comprises at least one amino acid substitution as compared to SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzyme exhibits at least 98% identity to SEQ ID NO:2, and wherein said variant enzyme has at least 1.1 fold better alkaline protease activity as compared to SEQ ID NO:2 under a condition selected from the group consisting of pH at 8.0, pH at 8.5, pH at 9, pH at 9.5, pH at 10, pH at 10.5, pH at 11, pH at 11.5 and pH at 12.

In some embodiments, the variant alkaline protease comprises at least one amino acid substitution as compared to SEQ ID NO:2, wherein said amino acid substitution is selected from the group consisting of: K18R, Q21G, A58G, S77A, I87V, A117V, A183G, F197Y, V203I, and I234V, wherein said variant alkaline protease enzyme exhibits at least 98% identity to SEQ ID NO:2, and wherein said variant enzyme has at least 1.1 fold better alkaline protease activity as compared to SEQ ID NO:2 under a condition selected from the group consisting of pH at 10.5, pH at 11 or pH at 11.3.

In some embodiments, the variant alkaline protease as described herein exhibits at least 99% identity to SEQ ID NO:2.

In some embodiments, the variant alkaline protease as described herein has one of said amino acid substitution, two of said amino acid substitutions, three of said amino acid substitutions, four of said amino acid substitutions, or five of said amino acid substitutions.

In some embodiments, the variant alkaline protease enzyme comprises an amino acid substitution at position 18. In some embodiments, the substitution is with any other of the 19 naturally occurring amino acids, namely serine, threonine, asparagine, glutamine, aspartic acid, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 18 is substituted with arginine (R). In some embodiments, the lysine (K) at position 18 is substituted with arginine (R). In some embodiments, the variant alkaline protease enzyme comprises or consists of the substitution K18R of SEQ ID NO:2.

In some embodiments, the variant alkaline protease enzyme comprises an amino acid substitution at position 21. In some embodiments, the substitution is with any other of the 19 naturally occurring amino acids, namely serine, threonine, asparagine, aspartic acid, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 21 is substituted with glycine (G). In some embodiments, the glutamine (Q) at position 21 is substituted with glycine (G). In some embodiments, the variant alkaline protease enzyme comprises or consists of the substitution Q21G of SEQ ID NO:2.

In some embodiments, the variant alkaline protease enzyme comprises an amino acid substitution at position 58. In some embodiments, the substitution is with any other of the 19 naturally occurring amino acids, namely serine, threonine, asparagine, glutamine, aspartic acid, lysine, arginine, histidine, glutamic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 58 is substituted with glycine (G). In some embodiments, the alanine (A) at position 58 is substituted with glycine (G). In some embodiments, the variant alkaline protease enzyme comprises or consists of the substitution A58G of SEQ ID NO:2.

In some embodiments, the variant alkaline protease enzyme comprises an amino acid substitution at position 77. In some embodiments, the substitution is with any other of the 19 naturally occurring amino acids, namely threonine, asparagine, glutamine, aspartic acid, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 77 is substituted with alanine (A). In some embodiments, the serine (S) at position 77 is substituted with alanine (A). In some embodiments, the variant alkaline protease enzyme comprises or consists of the substitution S77A of SEQ ID NO:2.

In some embodiments, the variant alkaline protease enzyme comprises an amino acid substitution at position 87. In some embodiments, the substitution is with any other of the 19 naturally occurring amino acids, namely serine, threonine, asparagine, glutamine, aspartic acid, lysine, arginine, histidine, glutamic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid at position 87 is substituted with valine (V). In some embodiments, the isoleucine (I) at position 87 is substituted with valine (V). In some embodiments, the variant alkaline protease enzyme comprises or consists of the substitution I87V of SEQ ID NO:2.

In some embodiments, the variant alkaline protease enzyme comprises an amino acid substitution at position 117. In some embodiments, the substitution is with any other of the 19 naturally occurring amino acids, namely serine, threonine, asparagine, glutamine, aspartic acid, lysine, arginine, histidine, glutamic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 117 is substituted with valine (V). In some embodiments, the alanine (A) at position 117 is substituted with valine (V). In some embodiments, the variant alkaline protease enzyme comprises or consists of the substitution A117V of SEQ ID NO:2.

In some embodiments, the variant alkaline protease enzyme comprises an amino acid substitution at position 183. In some embodiments, the substitution is with any other of the 19 naturally occurring amino acids, namely serine, threonine, asparagine, glutamine, aspartic acid, lysine, arginine, histidine, glutamic acid, cysteine, glycine, proline, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 183 is substituted with glycine (G). In some embodiments, the alanine (A) at position 183 is substituted with glycine (G). In some embodiments, the variant alkaline protease enzyme comprises or consists of the substitution A183G of SEQ ID NO:2.

In some embodiments, the variant alkaline protease enzyme comprises an amino acid substitution at position 197. In some embodiments, the substitution is with any other of the 19 naturally occurring amino acids, namely serine, threonine, asparagine, glutamine, aspartic acid, lysine, arginine, histidine, glutamic acid, cysteine, glycine, proline, alanine, isoleucine, leucine, methionine, phenylalanine, tryptophan, valine and tyrosine, with some embodiments not utilizing cysteine (due to possible disulfide formation) or proline (due to steric effects). In some embodiments, the amino acid at position 197 is substituted with tyrosine (Y). In some embodiments, the phenylalanine (F) at position 197 is substituted with tyrosine (Y). In some embodiments, the variant alkaline protease enzyme comprises or consists of the substitution F197Y of SEQ ID NO:2.

In some embodiments, the variant alkaline protease enzyme comprises an amino acid substitution at position 203. In some embodiments, the substitution is with any other of the 19 naturally occurring amino acids, namely serine, threonine, asparagine, glutamine, aspartic acid, lysine, arginine, histidine, glutamic acid, cysteine, glycine, proline, alanine, isoleucine, leucine, methionine, phenylalanine, tryptophan, and tyrosine, with some embodiments not utilizing cysteine (due to possible disulfide formation) or proline (due to steric effects). In some embodiments, the amino acid at position 203 is substituted with isoleucine (I). In some embodiments, the valine (V) at position 203 is substituted with isoleucine (I). In some embodiments, the variant alkaline protease enzyme comprises or consists of the substitution V203I of SEQ ID NO:2.

In some embodiments, the variant alkaline protease enzyme comprises an amino acid substitution at position 234. In some embodiments, the substitution is with any other of the 19 naturally occurring amino acids, namely serine, threonine, asparagine, glutamine, aspartic acid, lysine, arginine, histidine, glutamic acid, cysteine, glycine, proline, alanine, leucine, methionine, phenylalanine, tryptophan, valine and tyrosine, with some embodiments not utilizing cysteine (due to possible disulfide formation) or proline (due to steric effects). In some embodiments, the amino acid at position 234 is substituted with valine (V). In some embodiments, the isoleucine (I) at position 234 is substituted with valine (V). In some embodiments, the variant alkaline protease enzyme comprises or consists of the substitution I234V of SEQ ID NO:2.

In some embodiments, the variant alkaline protease enzyme as described herein comprises the animal acid substitutions selected from the group consisting of: Q21G/S77A/V203I, K18R/I87V, I87V/F197Y/V203I/I234V, A58G, K18R/Q21G/A58G/I87V/F197Y, S77A/A117V/I234V, K18R/A117V, Q21G/A58G/I87V, I87V/A117V, I87V/F197Y, K18R/Q21G/I87V, I87V, K18R/I234V, S77A/I87V/A117V, K18R/Q21G/V203I/I234V, K18R/S77A/A183G, S77A, K18R, Q21G/V203I, K18R/F197Y, K18R/I87V/F197Y/V203I and A117V as compared to SEQ ID NO:2.

In some embodiments, the variant alkaline protease enzyme as described herein comprises the animal acid substitutions selected from the group consisting of: Q21G/S77A/V203I, K18R/I87V, I187V/F197Y/V203I/I234V, A58G, K18R/Q21G/A58G/I87V/F197Y, S77A/A117V/I234V, K18R/A117V, Q21G/A58G/I87V, I87V/A117V, I87V/F197Y, K18R/Q21G/I87V, I87V, K18R/I234V, S77A/

I87V/A117V, K18R/Q21G/V203I/I234V, K18R/S77A/A183G, S77A, K18R, Q21G/V203I, K18R/F197Y, K18R/I87V/F197Y/V203I and A117V as compared to SEQ ID NO:2, and are at least 95%, 96%, 97%, 98% or 99% identical to SEQ ID NO:2.

In some embodiments, the variant alkaline protease enzyme as described herein comprises the animal acid substitutions of K18R/Q21G/A58G/I87V/F197Y or K18R/S77A/A183G as compared to SEQ ID NO:2.

In some embodiments, the variant alkaline protease enzyme as described herein comprises amino acid substitutions K18R/Q21G/A58G/I87V/F197Y, and exhibits at least 90% identity to SEQ ID NO:4.

In some embodiments, the variant alkaline protease enzyme as described herein has an amino acid sequence of SEQ ID NO:4.

In some embodiments, the variant alkaline protease enzyme as described herein comprises amino acid substitutions K18R/S77A/A183G, and exhibits at least 90% identity to SEQ ID NO:8.

In some embodiments, the variant alkaline protease enzyme as described herein has an amino acid sequence of SEQ ID NO:8.

In some embodiments, the variant alkaline protease enzyme comprises the amino acid substitution of K18R/I87V as compared to SEQ ID NO:2. In some embodiments, the variant alkaline protease enzyme comprises the amino acid substitution of K18R/I87V, and are at least 95%, 96%, 97%, 98% or 99% identical to SEQ ID NO:2.

In some embodiments, the variant alkaline protease enzyme comprises the amino acid substitution of I187V/F197Y/V203I/I234V as compared to SEQ ID NO:2. In some embodiments, the variant alkaline protease enzyme comprises the amino acid substitution of I87V/F197Y/V203I/I234V, and are at least 95%, 96%, 97%, 98% or 99% identical to SEQ ID NO:2.

In some embodiments, the variant alkaline protease enzyme comprises the amino acid substitution of A58G as compared to SEQ ID NO:2. In some embodiments, the variant alkaline protease enzyme comprises the amino acid substitution of A58G, and are at least 95%, 96%, 97%, 98% or 99% identical to SEQ ID NO:2.

In some embodiments, the variant alkaline protease enzyme comprises the amino acid substitution of K18R/Q21G/A58G/I87V/F197Y as compared to SEQ ID NO:2. In some embodiments, the variant alkaline protease enzyme comprises the amino acid substitution of K18R/Q21G/A58G/I87V/F197Y, and are at least 95%, 96%, 97%, 98% or 99% identical to SEQ ID NO:2.

In some embodiments, the variant alkaline protease enzyme comprises the amino acid substitution of Q21G/A58G/I87V as compared to SEQ ID NO:2. In some embodiments, the variant alkaline protease enzyme comprises the amino acid substitution of Q21G/A58G/I87V, and are at least 95%, 96%, 97%, 98% or 99% identical to SEQ ID NO:2.

In some embodiments, the variant alkaline protease enzyme comprises the amino acid substitution of I87V/F197Y as compared to SEQ ID NO:2. In some embodiments, the variant alkaline protease enzyme comprises the amino acid substitution of I87V/F197Y, and are at least 95%, 96%, 97%, 98% or 99% identical to SEQ ID NO:2.

In some embodiments, the variant alkaline protease enzyme comprises the amino acid substitution of K18R/Q21G/I87V as compared to SEQ ID NO:2. In some embodiments, the variant alkaline protease enzyme comprises the amino acid substitution of K18R/Q21G/I87V, and are at least 95%, 96%, 97%, 98% or 99% identical to SEQ ID NO:2.

In some embodiments, the variant alkaline protease enzyme comprises the amino acid substitution of K18R/Q21G/V203I/I234V as compared to SEQ ID NO:2. In some embodiments, the variant alkaline protease enzyme comprises the amino acid substitution of K18R/Q21G/V203I/I234V, and are at least 95%, 96%, 97%, 98% or 99% identical to SEQ ID NO:2.

In some embodiments, the variant alkaline protease enzyme comprises the amino acid substitution of K18R/S77A/A183G as compared to SEQ ID NO:2. In some embodiments, the variant alkaline protease enzyme comprises the amino acid substitution of K18R/S77A/A183G, and are at least 95%, 96%, 97%, 98% or 99% identical to SEQ ID NO:2.

In some embodiments, the variant alkaline protease enzyme comprises the amino acid substitution of S77A as compared to SEQ ID NO:2. In some embodiments, the variant alkaline protease enzyme comprises the amino acid substitution of S77A, and are at least 95%, 96%, 97%, 98% or 99% identical to SEQ ID NO:2.

In some embodiments, the variant alkaline protease enzyme comprises the amino acid substitution of K18R as compared to SEQ ID NO:2. In some embodiments, the variant alkaline protease enzyme comprises the amino acid substitution of K18R, and are at least 95%, 96%, 97%, 98% or 99% identical to SEQ ID NO:2.

In some embodiments, the variant alkaline protease enzyme comprises the amino acid substitution of K18R/F197Y as compared to SEQ ID NO:2. In some embodiments, the variant alkaline protease enzyme comprises the amino acid substitution of K18R/F197Y, and are at least 95%, 96%, 97%, 98% or 99% identical to SEQ ID NO:2.

In some embodiments, the variant alkaline protease enzyme comprises the amino acid substitution of A117V as compared to SEQ ID NO:2. In some embodiments, the variant alkaline protease enzyme comprises the amino acid substitution of A117V, and are at least 95%, 96%, 97%, 98% or 99% identical to SEQ ID NO:2.

The amino acid changes that may be present in addition to the specific substitutions described herein may be of a minor nature, that is conservative amino acid substitutions or insertions that do not significantly affect the folding and/or activity of the protein; small deletions, typically of 1 to about 30 amino acids; small amino- or carboxyl-terminal extensions, such as an amino-terminal methionine residue; a small linker peptide of up to about 20 to about 25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are e.g. Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuA al, Ala/Glu, and Asp/Gly.

C. Parent Alkaline Protease

The parent alkaline protease enzyme may be (a) a polypeptide having at least 80% sequence identity to the polypeptide of SEQ ID NO:1; (b) a polypeptide having at least 80% sequence identity to the polypeptide of SEQ ID NO:2; (c) a polypeptide encoded by a polynucleotide that hybridizes under medium-high stringency conditions with (i) the mature polypeptide coding sequence of SEQ ID NO:1 or SEQ ID NO:2, or (ii) the full-length complement of (i); or (d) a polypeptide encoded by a polynucleotide having at least 70% sequence identity to the mature polypeptide coding sequence of SEQ ID NO:1 or SEQ ID NO:2. For hybridization methods and conditions, see for example, Sambrook et al., 1989, Molecular Cloning, A Laboratory Manual, 2d edition, Cold Spring Harbor, New York.

In some embodiments, the parent alkaline protease enzyme has a sequence identity to the polypeptide of SEQ ID NO: 1 of at least 85%, at least 90%, at least 91%, at least 92%, at least 93%, at least 94%, at least 95%, at least 96%, at least 97%, at least 98%, at least 99%, or 100%, and have alkaline protease activity. In one aspect, the amino acid sequence of the parent differs by up to 10 amino acids, e.g., 1, 2, 3, 4, 5, 6, 7, 8, 9, or 10, from the mature polypeptide of SEQ ID NO: 1.

In some embodiments, the parent alkaline protease enzyme has a sequence identity to the polypeptide of SEQ ID NO: 2 of at least 85%, at least 90%, at least 91%, at least 92%, at least 93%, at least 94%, at least 95%, at least 96%, at least 97%, at least 98%, at least 99%, or 100%, and have alkaline protease activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In some embodiments, the parent alkaline protease enzyme is encoded by a polynucleotide having a sequence identity to the mature polypeptide coding sequence of SEQ ID NO:1 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In some embodiments, the parent alkaline protease enzyme is encoded by a polynucleotide having a sequence identity to the mature polypeptide coding sequence of SEQ ID NO:2 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

In some embodiments, the parent alkaline protease enzyme is from *Neosartorya fumigate* (P28296, noted as Nf.AP), e.g., the alkaline protease of SEQ ID NO:1.

In some embodiments, the parent alkaline protease enzyme is from *Aspergillus oryzae* (P12547, noted as Ao.AP), e.g., the alkaline protease of SEQ ID NO:2.

In one embodiment, the variant alkaline protease enzymes are more stable than the parent alkaline protease enzyme when exposed to temperatures of about 20° C., about 25° C., about 30° C., about 35° C., about 40° C., about 45° C., about 50° C., about 55° C., about 60° C., and/or about 65° C. for a period of time, generally ranging from about 1, 2, 3, 4, 5, 6, 7, 8, 9 or 10 minutes or longer, depending on the ultimate conditions for the use of the variant alkaline protease enzyme, with some embodiments utilizing thermal challenge times of 5 minutes to 10 minutes, 5 minutes to 15 minutes, 5 minutes to 60 minutes, 10 minutes to 60 minutes all finding use in the present invention.

In one embodiment, the variant alkaline protease enzymes are more stable than the parent alkaline protease enzyme when exposed to pH of 8.0, 8.5, 9, 9.5, 10, 10.5, 11, 11.5 and 12 for a period of time, generally ranging from about 1, 2, 3, 4, 5, 6, 7, 8, 9 or 10 minutes or longer, depending on the ultimate conditions for the use of the variant alkaline protease enzyme, with some embodiments utilizing pH challenge times of 5 minutes to 10 minutes, 5 minutes to 15 minutes, 5 minutes to 60 minutes, 10 minutes to 60 minutes all finding use in the present invention.

Accordingly, as shown in FIGS. 4 and 5, a number of variant alkaline protease enzymes of the invention exhibit increased thermostability and pH stability.

In some embodiments, the variant alkaline protease enzymes have improved alkaline protease activity and stability as compared to the parent alkaline protease enzyme(s) under the same ionic strength condition (e.g. soft and/or hard water).

In some embodiments, the variant alkaline protease enzymes have longer shelf life at room temperature than the parent alkaline protease enzyme(s).

In some embodiments, the variant alkaline protease enzymes have high stability to withstand the formulated detergent ingredients (e.g. oxidizing and chelating agents) as compared to the parent alkaline protease enzyme(s).

In some embodiments, the variant alkaline protease enzymes have broader substrate specificity than the parent alkaline protease enzyme(s).

In some embodiments, the variant alkaline protease enzymes have improved washing performance on stains as compared to the parent alkaline protease enzyme(s).

X. NUCLEIC ACID COMPOSITIONS

The present invention also provides compositions comprising a variant alkaline protease enzyme encoding nucleic acid of the present invention. Such variant alkaline protease polyepepide encoding nucleic acids can encode any of the variant alkaline protease enzymes recited in the present application, including under section "SPECIFIC VARIANT ALKALINE PROTEASES" above. In some embodiments, the composition comprises a nucleic acid selected from the sequences as shown in the Sequence listing.

In some embodiments, the nucleic acid encoding the variant alkaline protease enzyme comprises a codon optimized version or variant of any of the nucleic acid sequences. "Codon optimized" in this context is done in relation to a particular host organism and its generally preferred amino acid codons; that is, the host production organism, e.g. an *Aspergillus species*, may yield higher translation and/or secretion using *Aspergillus* preferred codons as compared to a yeast production organism.

In some embodiments, the compositions are enriched in such a variant alkaline protease enzyme encoding nucleic acid of the present invention. The term "enriched" indicates that the alkaline protease activity capable of being obtained from the composition has been increased, e.g., with an enrichment factor of at least 1. In some embodiments, the compositions are formulated to provide desirable characteristics such as low color, low odor and acceptable storage stability.

A. Preparation of Variants

The variants can be prepared generally by constructing genes encoding the protein sequence using well known techniques, including site-directed mutagenesis of a parental gene and synthetic gene construction.

As is known in the art, alkaline proteases are generally made using a signal sequence that directs the protein to be secreted from the cell, as well as a pro-sequence that keeps the protein inactive until it is removed. As is known in the art, secreted proteases such as the variant alkaline proteases of the invention include a signal sequence (also referred to as a "pre" sequence), in addition to a pro-sequence that is removed upon or during secretion. The pre and pro sequences of the wild type enzymes are shown in FIG. 3.

As will be appreciated by those in the art, the variant proteases of the invention can be made using either the endogenous signal and pro sequences, or exogeneous ones.

1. Regulatory Sequences

The present invention also relates to nucleic acid constructs comprising a polynucleotide encoding a variant of the present invention operably linked to one or more control sequences that direct the expression of the coding sequence in a suitable host cell under conditions compatible with the control sequences.

The control sequence may include a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from *Aspergillus* species genes, as is known in the art, including *A. nidulans, A. niger* and *A. oryzae*, as well as *Rhizomucor* species genes such as *R. miehei, Trichoderma* species genes including *T. reesei, Fusarium* species genes including *F. venenatum*. Yeast control sequences including promoters are also well known from *Saccharomyces cerevisiae.*

Suitable promoter sequences (as well as other control sequences) from these species include the promoters from amylases (α-amylase in particular), glucoamylases, proteases, phosphatases, endoglucanases, cellulases, etc. as are known in the art. In addition, as for codon-optimization, it may be desirable to use promoters (and other control sequences) that are endogeneous to the host production strain, operably linked to the nucleic acids encoding the variant alkaline protease.

The control sequence may also be a transcription terminator, which is recognized by a host cell to terminate transcription. The terminator sequence is operably linked to the 3'-terminus of the polynucleotide encoding the variant. Any terminator that is functional in the host cell can be used.

In some embodiments, terminators (and other control sequences such as promoters) for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

In some embodiments, terminators for yeast host cells are obtained from the genes for Saccharomyces cerevisiae enolase, Saccharomyces cerevisiae cytochrome C (CYC1), and Saccharomyces cerevisiae glyceraldehyde-3-phosphate dehydrogenase.

The control sequence can also be an mRNA stabilizer region downstream of a promoter and upstream of the coding sequence of a gene which increases expression of the gene.

Examples of suitable mRNA stabilizer regions are obtained from a *Bacillus thuringiensis* crylllA gene (WO 94/25612) and a *Bacillus subtilis* SP82 gene (Hue et al., 1995, *Journal of Bacteriology* 177: 3465-3471).

The control sequence can also be a leader, a nontranslated region of an mRNA that is important for translation by the host cell. The leader sequence is operably linked to the 5'-terminus of the polynucleotide encoding the variant. Any leader that is functional in the host cell may be used.

In some embodiments, leaders for filamentous fungal host cells are obtained from the genes for *Aspergillus oryzae* TAKA amylase and *Aspergillus nidulans* triose phosphate isomerase.

In some embodiments, suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence can also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

In some embodiments, polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

The control sequence may also be a signal peptide coding region that encodes a signal peptide linked to the N-terminus of a variant and directs the variant alkaline protease being expressed into the cell's secretory pathway. In many instances, the signal sequence is the endogeneous G1P signal sequence.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the Gpd (Glyceraldehyde-3-phosphate dehydrogenase) from *Ascomycota* such as *Aspergillus, Aspergillus niger* glucoamylase promoter, *Aspergillus oryzae* TAKA alpha-amylase promoter, and *Aspergillus oryzae* glucoamylase promoter can be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

2. Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector can be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used. Vectors contemplated for use with the methods of the invention include both integrating and non-integrating vectors.

In some embodiments, the vector contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

In some embodiments, the vector contains an element(s) that permits integration of the vector into the host cell's genome or autonomous replication of the vector in the cell independent of the genome.

For integration into the host cell genome, the vector can rely on the polynucleotide's sequence encoding the variant or any other element of the vector for integration into the genome by homologous or non-homologous recombination. Alternatively, the vector can contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector can further comprise an origin of replication enabling the vector to replicate autonomously in the host cell in question. The origin of replication can be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention can be inserted into a host cell to increase production of a variant, including the use of multiple genes encoding the variant alkaline protease in a vector, multiple vectors transformed into a cell, or multiple integrations of a vector into the genome. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

3. Particular Constructs

For expression in yeast, one embodiment utilizes *Saccharomyces cerevisiae* INSCV1 strain (ThermoFisher Scientific, USA: Catalogue # V8251-20) and pYES2/CT vector (ThermoFisher Scientific, USA: Catalogue # V8251-20). Both are commercially available and are also discussed in Example 1 below.

a. Codon Optimization

Codon optimization can be employed with any of the variant alkaline protease enzymes of the present invention, in order to optimize expression in the host cell employed. Such methods are well known in the art and described in, for example, WO 2007/142954. In heterologous expression systems, optimization steps can improve the ability of the host to produce the desired variant alkaline protease enzymes. Protein expression is governed by a host of factors including those that affect transcription, mRNA processing, and stability and initiation of translation. The polynucleotide optimization steps can include steps to improve the ability of the host to produce the foreign protein as well as steps to assist the researcher in efficiently designing expression constructs. Optimization strategies can include, for example, the modification of translation initiation regions, alteration of mRNA structural elements, and the use of different codon biases.

In some embodiments, reduced heterologous protein expression occurs through interfering secondary structures. Secondary structures can sequester the RBS sequence or initiation codon and have been correlated to a reduction in protein expression. Stemloop structures can also be involved in transcriptional pausing and attenuation. An optimized polynucleotide sequence can contain minimal secondary structures in the RBS and gene coding regions of the nucleotide sequence to allow for improved transcription and translation.

In some embodiments, restriction sites can effect heterologous protein expression. By modifying restriction sites that could interfere with subsequent sub-cloning of transcription units into host expression vectors a polynucleotide sequence can be optimized.

In some embodiments, the optimized nucleic acid sequence can express the variant alkaline protease enzyme of the invention, at a level which is at least 110%, 150%, 200%, 500%, 1,000%, 5,000% or even 10,000% of that expressed by nucleic acid sequence that has not been optimized.

4. Host Cells and Production Strains

As will be appreciated by those in the art, there are a wide variety of production host organisms for the recombinant production of the variant alkaline protease enzymes of the invention, including, but not limited to bacterial cells and fungal cells including yeast.

The present invention also relates to recombinant host cells, comprising a polynucleotide encoding a variant alkaline protease of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The choice of a host cell will to a large extent depend upon the gene encoding the variant and the ability of the host production organism to yield high protein titers of expressed and/or secreted proteins. In some embodiments, the host cell exhibits transitory expression of the variant alkaline protease. In some embodiments, the host cell is a stably transfected host or a host cell that stably (i.e., permanently) expresses the variant alkaline protease. In some embodiments, the host cell is a production host cell. The transformation and/or transfection of the host cells with the expression vectors comprising the coding region for the variant alkaline protease of the invention is done as is well known in the art (See Sambrook, id.).

The host cell can be any cell useful in the recombinant production of a variant, e.g., a prokaryote or a eukaryote. Such host cells include but are not limited to bacterial, fungal, and yeast cells. The host cell can also be a eukaryote, such as a mammalian, insect, plant, or fungal cell.

The host cell can be a fungal cell. "Fungi" as used herein includes the phyla *Ascomycota, Basidiomycota, Chytridiomycota*, and *Zygomycota* as well as the *Oomycota* and all mitosporic fungi (as defined by Hawksworth et al., In, Ainsworth and Bisby's Dictionary of The Fungi, 8th edition, 1995, CAB International, University Press, Cambridge, UK). In many cases, host cells include *Aspergillus* species including *A. nidulans, A. niger* and *A. oryzae*, as well as *Rhizomucor* species such as *R. miehei, Trichoderma* species including *T. reesei* and *Fusarium* species genes including *F. venenatum*. The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonaturn, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulaturn, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

In some embodiments, the fungal host cell can be a yeast cell. "Yeast" as used herein includes ascosporogenous yeast (*Endomycetales*), basidiosporogenous yeast, and yeast belonging to the *Fungi Imperfecti* (*Blastomycetes*). The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

XI. COMPOSITIONS OF THE INVENTION

The present invention also provides compositions comprising a variant alkaline protease enzyme of the present invention. In some embodiments, the composition comprises a carrier and/or an excipient. In some embodiments, the compositions are enriched in such a variant alkaline protease enzyme of the present invention. The term "enriched" indicates that the alkaline protease activity of the composition has been increased, e.g., with an enrichment factor of at least 1. In some embodiments, the compositions are formulated to provide desirable characteristics as detergent additives, such as high washing performance on stains, high washing performance in different ionic strengths (e.g. both soft and hard water), ability to withstand oxidizing and chelating agents in formulated detergents, low color, low odor and long shelf life at room temperature.

In some embodiments, the composition comprises a variant alkaline protease enzyme of the present invention as the major enzymatic component, e.g., a mono-component composition.

In some embodiments, the composition may comprise one or more additional enzymes, depending on the end use, including, but not limited to, aminopeptidase, alpha-amylase, beta-amylase, isoamylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, glucoamylase, polyphenoloxidase, pullulanase, proteolytic enzyme, ribonuclease, transglutaminase, and/or xylanase.

In some embodiments, the composition comprises an amylase and the variant alkaline protease enzyme according to the invention. In some embodiments, the composition comprises a lipase and the variant alkaline protease enzyme according to the invention. In another embodiment the composition comprises an amylase, a lipase and the variant alkaline protease according to the invention.

In some embodiments, the composition comprises the variant alkaline protease enzyme of the invention further comprises acid, neutral and/or alkaline proteases. In another embodiment the composition comprises the variant alkaline protease according to the invention and one or more enzymes including amylase, proteases, peptidase, lipase, cellulose, and/or others.

A. Formulations of Variant Alkaline Proteases

As will be appreciated by those in the art, the formulation of the variant alkaline protease of the invention depends on its end use and the associated conditions. Suitable formulations for the variant alkaline proteases of the invention include liquid formulations, dried formulations (including spray dried formulations), powdered formulations, granular formulations, microgranulate formulations and pelleted formulations. The variant alkaline proteases can be stabilized in accordance with methods known in the art.

In some embodiments, the enzyme composition (i.e., polypeptide compositions) of the present invention can be in any form suitable for use, such as, for example, a crude fermentation broth with or without cells removed, a cell lysate with or without cellular debris, a semi-purified or purified enzyme composition, or a host cell, as a source of the enzymes.

In some embodiments, the enzyme composition can be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

In some embodiments, the dosage of the polypeptide composition of the invention and other conditions under which the composition is used may be determined on the basis of methods known in the art.

XII. METHODS OF PRODUCTION

The present invention also relates to methods of producing a variant alkaline protease enzyme, comprising: (a) cultivating a host cell of the present invention under conditions suitable for expression of the variant alkaline protease polypeptide; and (b) optionally recovering the variant alkaline protease polypeptide.

The host cells are cultivated in a nutrient medium suitable for production of the variant alkaline protease polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the variant alkaline protease polypeptide is secreted into the nutrient medium, the variant alkaline protease polypeptide can be recovered directly from the medium. If the variant is not secreted, it can be recovered from cell lysates.

The variant alkaline protease polypeptide can be detected using methods known in the art that are specific for the variants. These detection methods include, but are not limited to, use of specific antibodies, formation of an enzyme product, or disappearance of an enzyme substrate. For example, an enzyme assay as outlined herein may be used to determine the activity of the variant alkaline protease polypeptide.

The variant alkaline protease polypeptide can be recovered using methods known in the art. For example, the variant alkaline protease polypeptide can be recovered from the nutrient medium by conventional procedures including, but not limited to, collection, centrifugation, filtration, extraction, spray-drying, evaporation, or precipitation.

The variant can be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

XIII. METHODS OF USING VARIANT ALKALINE PROTEASES

A. Industiral Applications of the Variant Alkaline Proteases

The variant alkaline proteases of the present invention possess important properties allowing for a variety of industrial applications, such as leather processing, food processing, medicinal uses, chemical industry, detergent industry etc.

1. Detergent Industry

The use of variant alkaline proteases in detergent industry has a number of benefits, including increased activity, thermoactivity, thermostability, pH stability, high washing performance on stains, high washing performance in different ionic strengths (e.g. both soft and hard water), ability to withstand oxidizing and chelating agents in formulated detergents and long shelf life at room temperature as compared to a parent alkaline protease.

In some embodiments, the variant alkaline proteases of the invention are formulated and added to a detergent or can be made as a component of a detergent. In some embodiments, the detergent is a laundry detergent. In some embodiments, the detergent is a dishwasher detergent. In some embodiments, the detergent is a contact lens detergent.

In one embodiment, the alkaline protease is added to a detergent as is known in the art, such that the detergent is formed with the alkaline protease in it. In other embodiments, the alkaline protease can be sprayed or dosed in a liquid form into detergents.

In some embodiments, the present invention includes methods for cleaning the surface(s) of laundry, dishes and/or contact lens comprising contacting the surface(s) with the variant alkaline protease enzyme(s) according to the present invention.

In some embodiments, the present invention includes methods for cleaning the surface(s) of laundry, dishes and/or contact lens comprising contacting the surface(s) with the detergent(s) according to the present invention.

2. Leather Industry

Traditionally, the dehairing process in the leather industry is carried out by treating animal hides with a saturated solution of lime and sodium sulphide, besides being expensive and particularly unpleasant to carry out, a strongly polluting effluent is produced. The alternative to this process is enzyme-assisted dehairing. Enzyme-assisted dehairing is preferentially possible if proteolytic enzymes can be found that are stable and active under the alkaline conditions (pH 12) of tanning (P Ellaiah, B Srinivasulu et al. 2002, Journal of Scientific & Industrial Research. 61:690-704).

In some embodiments, the invention provides methods of using the variant alkaline proteases as described above for dehairing of animal hides of skin in the leather industry.

In some embodiments, the invention provides methods of using the variant alkaline proteases as bating agents for producing high quality leathers with improved properites, such as increase in the tensile, bursting and tear strengths, and/or elongation at breaking of the leathers.

3. Food Industry

Alkaline proteases can hydrolyse proteins from plants, fish or animals to produce hydrolysates of well-defined peptide profile, and find wide use in food processing industry (P Ellaiah, B Srinivasulu et al. 2002, Journal of Scientific & Industrial Research. 61:690-704). The invention provides methods of using the variant alkaline proteases as described above in food processing industry.

In some embodiments, the invention provides methods of using the variant alkaline proteases as described above for producing fermented milk products such as cheese.

In some embodiments, the invention provides methods of using the variant alkaline proteases as described above for producing a less bitter hydrolysate and/or a debittered enzymatic whey protein hydrolysate.

In some embodiments, the invention provides methods of using the variant alkaline proteases as described above for fortification of fruit juices or soft drinks and/or manufacturing protein-rich therapeutic diets.

In some embodiments, the invention provides methods of using the variant alkaline proteases as described above for producing physiologically functional food (e.g. the food that play an important role in regulating blood pressure).

In some embodiments, the invention provides methods of using the variant alkaline proteases as described above for tenderizing meat.

In some embodiments, the invention provides methods of using the variant alkaline proteases as described above optionally in combination with other kinds of proteases (e.g. neutral proteases) for hydrolyzing raw meat. In further embodiments, the resulting meat hydrolysate exhibit superior organoleptic properties and can be used as meat flavoured additive to soup concentrations.

4. Chemical Industry

Variant alkaline proteases of the invention can be used in synthetic chemistry. In some embodiments, the invention provides methods of using the variant alkaline proteases as described above for catalyzing peptide synthesis in organic solvents. In some embodiments, the invention provides methods of using the variant alkaline proteases as described above for synthesizing peptides enzymatically, optionally with the proteases immobilized on insoluble supports.

B. Combinations

Depending on the applications, the variant enzymes of the invention can be combined with other enzymes, including but not limited to carboxypeptidases, alpha-amylases, lactases, sucrases, maltases, lipases, cellulases, mannanases, pectinases, etc.

XIV. EXAMPLES

Example 1

Gene Synthesis and Cloning

Two novel alkaline proteases have been identified: one is from *Neosartorya fumigate* (P28296, noted as Nf.AP), the other is from *Aspergillus oryzae* (P12547, noted as Ao.AP). The starting genes of them were synthesized by GenScript (http://www.genscript.com/). The synthesized genes were cloned into the pESC-URA vector (Agilent Technologies, Santa Clara, Calif., Catalogue #217454).

Example 2

Mutant Collection Design and Construction

One generation of improvement was completed for each gene. The starting alkaline protease gene was used as the parent (G1P). To improve the activity, thermostability and high pH tolerance of G1P, 1 mutant collection was designed based on G1P protein sequence. The design includes one to multiple specific mutations per variant. The mutant collections were constructed using standard site-directed mutagenesis methods and subsequently cloned into the pESC-URA vector (Agilent Technologies, Santa Clara, Calif., Catalogue #217454).

Example 3

Preparation of HTP Alkaline Protease-Containing Wet Cell Pellets

The *Saccharomyces cerevisiae* INSCV1 strain (ThermoFisher Scientific, USA: Catalogue # V8251-20) containing recombinant alkaline protease-encoding genes from single colonies were inoculated into individual wells of 96 well plates containing 300 μl synthetic minimal defined medium (SC) with 2% glucose and no uracil supplementation. The cultures were grown overnight at 30° C., 250 rpm and 85% humidity. Appropriate volume of overnight culture from each well needed to obtain an OD600 of 0.4 was added to corresponding wells of the new 96 well plates containing 350 μl of induction medium (SC selective medium containing 2% galactose). The plates were then incubated for 24 hrs. at 30° C., 250 rpm and 85% humidity. The cells were then pelleted using centrifugation at 4000 rpm for 10 min at 4° C. The supernatants were discarded, and the pellets frozen at −80° C. prior to lysis.

Example 4

Lysis of the HTP Alkaline Protease Plates

150 μL of Y-PER yeast protein extraction reagent (ThermoFisher Scientific, USA: Catalogue #78990) was added to the cell paste in each well as described above. The cells were lysed at room temperature for 1.5 hrs. lysis method was used with shaking on a bench top shaker. The plate was then centrifuged for 10 min at 4000 rpm and 4° C. The clear supernatants were used to perform biochemical assays to determine activity.

Example 5

Evaluate the pH and Temperature Profiles of G1P a. pH Profile

To each well of the reaction plate(s), 50 μl (final 0.21% w/v) N,N-dimethyl casein (DMC) solution (adjusted to pH 8-11 with sodium hydroxide) is added. 25 μL of the lysate from example 4 is then added to each well. The plates are sealed and incubated at 37° C. for 4 hrs. at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm.

Figure 1B:
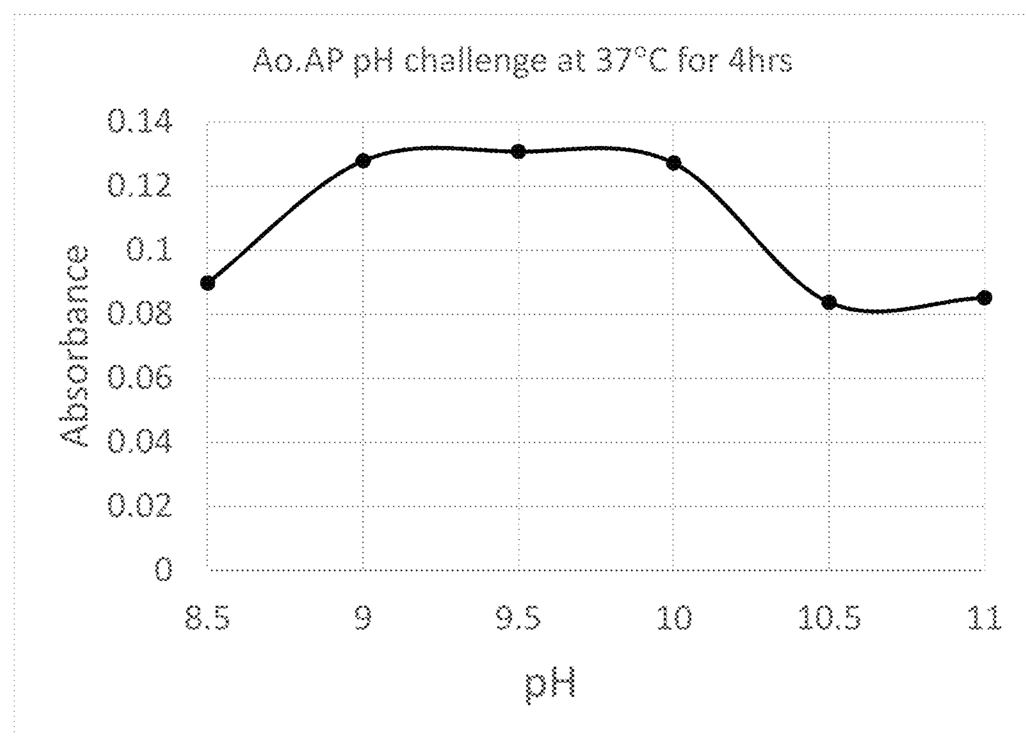

Preparation of DMC substrate: To 200 mL of boiling water 3.20 g DMC is added and stirred. After heating the substrate for 20 minutes it is cooled down at room temperature. In a separate beaker, 25.92 g sodium tetraborate decahydrate ($Na_2B_4O_7.10H_2O$) and 13.30 g sodium dihydrogen phosphate monohydrate ($NaH_2PO_4.H_2O$) is added to ~500 mL MQ water and stirred to dissolve. The DMC solution and the borate solution are mixed, and the volume bought up to 1 L. The pH is 8.00±0.05. The solution is filtered twice through filter paper and 600 μL of 30% Brij35 reagent is added. The final stock of DMC is 0.32% (w/v). The pH of substrate solution is adjusted between (8-11) using sodium hydroxide. The results are shown in FIG. 1.

b. Temperature Profile

Figure 2A:
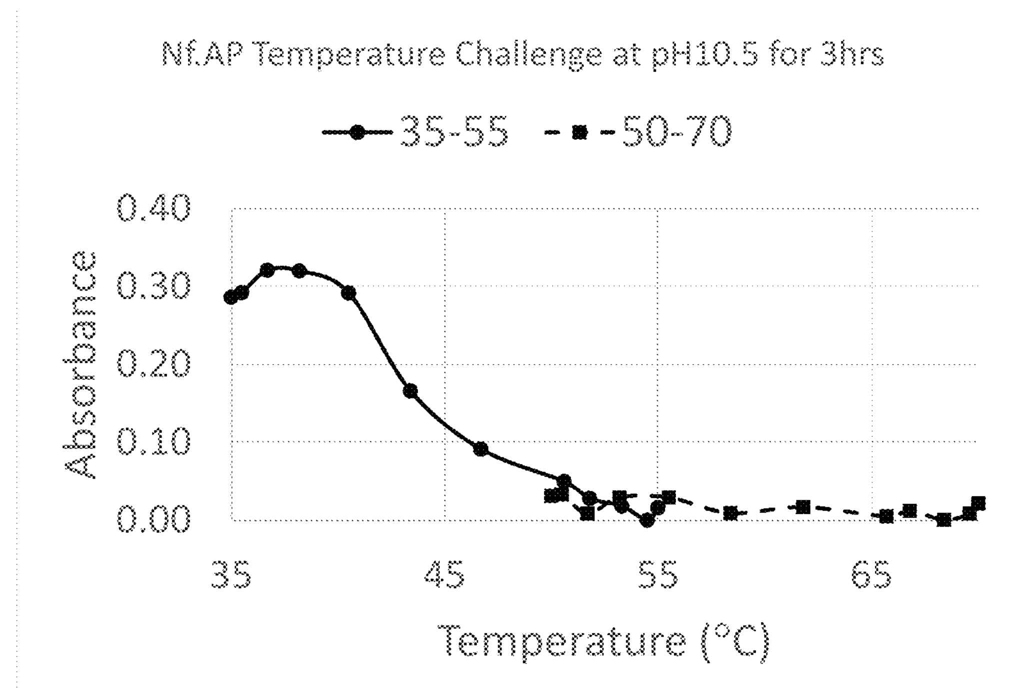
Figure 2B:
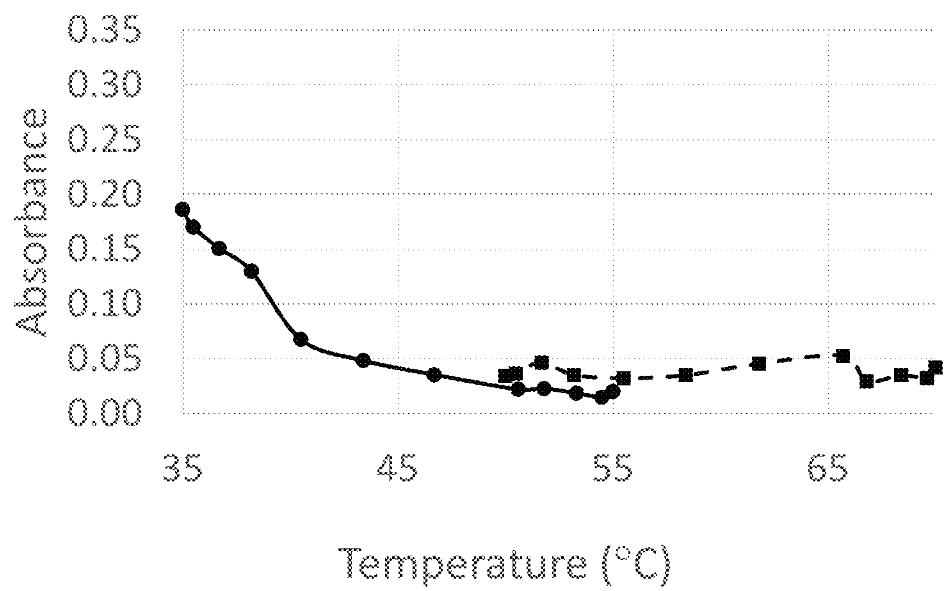

To each well of the reaction plate(s), 50 μl (final 0.21% w/v) N,N-dimethyl casein (DMC) solution (adjusted to pH 10.5 with sodium hydroxide) is added. 25 μL of the lysate from example 4 is then added to each well. The plates are sealed and incubated in a temperature range of 35-70° C. for 3 hrs in a thermocycler. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. The results are shown in FIG. 2.

Example 6

Screening of Nf.AP Mutants for Improved High pH Tolerance

To each well of the reaction plate(s), 50 μL N,N-dimethyl casein (DMC) solution (adjusted to pH 11.3 with sodium hydroxide) is added. 25 μL of the lysate from example 4 is then added to each well. The plates are sealed and incubated at 37° C. for 3 hrs at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. The results are shown in FIG. 4.

Example 7

Screening of Nf.AP Mutants for Improved Thermostability

To each well of the reaction plate(s), 50 μL N,N-dimethyl casein (DMC) solution (adjusted to pH 11.0 with sodium hydroxide) is added. 25 μL of the lysate from example 4 is then added to each well. The plates are sealed and incubated at 40° C. for 3 hrs at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. The results are shown in FIG. 4.

Example 8

Screening of Ao.AP Mutants for Improved Activity

To each well of the reaction plate(s), 50 μL N,N-dimethyl casein (DMC) solution (adjusted to pH 10.5 with sodium hydroxide) is added. 25 μL of the lysate from example 4 is then added to each well. The plates are sealed and incubated at 37° C. for 3 hrs at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. The results are shown in FIG. 5.

Example 9

Screening of Ao.AP Mutants for Improved Thermostability

To each well of the reaction plate(s), 50 μL N,N-dimethyl casein (DMC) solution (adjusted to pH 10.5 with sodium hydroxide) is added. 25 μL of the lysate from example 4 is then added to each well. The plates are sealed and incubated at 42° C. for 3 hrs at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. The results are shown in FIG. 5.

Example 10

Construct Making in *Pichia*

Pro-mature domain of Nf.AP and Nf.AP G1V3 was amplified by PCR using Nf.AP_Fwd_del pre primer (tcagtctcgagaaaagagaggctgaagctCCTGTCCAGGAAACTC, the lower-case letters are linker sequence and the underlined letters are a restriction enzyme site) and Nf.AP_Rvr (tcgttagcggccgcctattaAGCATTGCCATTGTA). The amplified fragment (22 aa to 403 aa) was digested with XhoI and NotI and then integrated in pPICZa with the corresponding sites. The constructed plasmid (pPICZa-Pro-Nf.AP/Nf.AP G1V1)

had the “Pro-gene” of either Nf.AP or Nf.AP G1V1 fused to alpha-factor with a Kex2 cleavage site.

Example 11

Preparation of Protease Variants Produced by *Pichia pastoris* in HTP

Protease-encoding genes from single colonies were inoculated into individual wells of 24 well plates containing 2000 μl of BMGY medium according to ThermoFisher Scientific recipe. The cultures were grown for 18 hrs at 30° C., 200 rpm and 85% humidity. After 18 hrs, centrifuge 24 wells plate and decant the liquid media. Into the pellet, add 2000 μl of BMMY medium according to ThermoFisher Scientific receipe. Add 200 μl of 10% methanol to each plate. The plates were incubated at 30° C., 200 rpm and 85% humidity incubator. At every 24 hrs, add 200 μl of 10% methanol to each plate. Harvest plate at 72 hrs by centrifuging plates at 4,000 rpm at 4° C. for 10 minutes. The supernatants were transferred to costar deep wells plates and stored at −20° C. prior to activity assay.

Example 12 pH Profile of Nf.AP and Nf.AP G1V3 in *Pichia pastoris*

To each well of the reaction plate(s), 50 μl (final 0.21% w/v) N,N-dimethyl casein (DMC) solution (adjusted to pH 8-11 with sodium hydroxide) is added. 25 μL of the supernatant (32× dilution with appropriate buffer) from example 11 is then added to each well. The plates are sealed and incubated at 37° C. for 1 hrs. at 200 rpm. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm.

Preparation of DMC substrate: To 200 mL of boiling water 3.20 g DMC is added and stirred. After heating the substrate for 20 minutes it is cooled down at room temperature. In a separate beaker, 25.92 g sodium tetraborate decahydrate (Na¬2B4O7.10H2O) and 13.30 g sodium dihydrogen phosphate monohydrate (NaH2PO4.H2O) is added to ~500 mL MQ water and stirred to dissolve. The DMC solution and the borate solution are mixed, and the volume bought up to 1 L. The pH is 8.00±0.05. The solution is filtered twice through filter paper and 600 μL of 30% Brij35 reagent is added. The final stock of DMC is 0.32% (w/v). The pH of substrate solution is adjusted between (8-11) using sodium hydroxide. The pH profile determined is shown in FIG. 13.

Example 13

Thermoactivity Profile of Nf.AP and Nf.AP G1V3 in *Pichia pastoris*

To each well of the reaction plate(s), 50 μl (final 0.21% w/v) N,N-dimethyl casein (DMC) solution (adjusted to pH 10.5 with sodium hydroxide) is added. 25 μL of the supernatant (16× dilution) from example 11 is then added to each well. The plates are sealed and incubated in a temperature range of 40-52° C. for lhrs in a thermocycler. After incubation, the plates are centrifuged and 25 μL of 1 mol/L 2,4,6-trinitrobenzenesulfonic acid (TNBS) coloring solution is added to each well. The plates are sealed and placed in dark for 30 minutes. The absorbance is recorded at 405 nm. The thermoactivity profile determined is shown in FIG. 14.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only.

What is claimed is:

1. A composition comprising a variant alkaline protease enzyme comprising at least one amino acid substitution as compared to SEQ ID NO:1, wherein said variant alkaline protease enzyme has alkaline protease activity, wherein said amino acid substitution is selected from the group consisting of: K18R, A21G, D24H, S53G, A58G, T91A, A130V, I234V, N246G and K275L, wherein said variant alkaline protease enzyme exhibits at least 96% sequence identity to SEQ ID NO:1, and wherein said variant alkaline protease enzyme has eleven or less amino acid substitutions as compared to SEQ ID NO:1.

2. The composition according to claim 1, wherein said variant alkaline protease enzyme exhibits at least 97%, 98%, or 99% sequence identity to SEQ ID NO:1.

3. The composition according to claim 1, wherein said variant alkaline protease enzyme has one of said amino acid substitution, two of said amino acid substitutions, three of said amino acid substitutions, four of said amino acid substitutions, five of said amino acid substitutions, six of said amino acid substitutions, seven of said amino acid substitutions, eight of said amino acid substitutions, nine of said amino acid substitutions, or ten of said amino acid substitutions.

4. The composition according to claim 1, wherein said amino acid substitution(s) are selected from the group consisting of: K18R/A58G/N246G, K18R/I234V, K18R/A21G/S53G/A58G/K275L, K18R/S53G/A130V/I234V, K18R/A58G, K18R/T91A/I234V/N246G/K275L, K18R/A21G/A58G/I234V, K18R/S53G, K18R/A21G, K18R, K18R/A21G/I234V/N246G, K18R/S53G/A58G/I234V, K18R/S53G/T91A, K18R/A58G/I234V/K275L, K18R/I234V/K275L, K18R/A58G/K275L, K18R/A21G/A58G, K18R/D24H/S53G/A58G/A130V, K18R/S53G/A130V/K275L and K18R/S53G/T91A/I234V/K275L.

5. The composition according to claim 1, wherein said amino acid substitutions are selected from the group consisting of: K18R/A58G/N246G, K18R/I234V, K18R/S53G/A130V/I234V and K18R/A58G.

6. The composition according to claim 1, wherein said variant alkaline protease enzyme comprises amino acid substitutions K18R/I234V, and exhibits at least 97% sequence identity to SEQ ID NO:3.

7. The composition according to claim 1, wherein said variant alkaline protease enzyme has the amino acid sequence of SEQ ID NO:3.

8. The composition according to claim 1, wherein the composition is a detergent composition comprising said variant alkaline protease enzyme.

9. A method of cleaning surface(s) of laundry, dishes and/or contact lens comprising contacting said surface(s) with the composition comprising said variant alkaline protease enzyme according to claim 1.

* * * * *